(12) United States Patent
Dominique et al.

(10) Patent No.: US 8,093,253 B2
(45) Date of Patent: Jan. 10, 2012

(54) LEUKOTRIENE B$_4$ INHIBITORS

(75) Inventors: Romyr Dominique, Wayne, NJ (US);
Robert Alan Goodnow, Jr., Gillette, NJ (US); Agnieszka Kowalczyk, Mine Hill, NJ (US); Jianping Lou, Hillsborough, NJ (US); Qi Qiao, Bloomfield, NJ (US); Achyutharao Sidduri, Livingston, NJ (US); Jefferson Wright Tilley, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 455 days.

(21) Appl. No.: 12/390,725

(22) Filed: Feb. 23, 2009

(65) Prior Publication Data

US 2009/0227603 A1 Sep. 10, 2009

Related U.S. Application Data

(60) Provisional application No. 61/034,307, filed on Mar. 6, 2008.

(51) Int. Cl.
*A01N 43/54* (2006.01)

(52) U.S. Cl. ........ 514/256; 514/406; 514/419; 514/438; 514/571; 544/335; 548/204; 548/469; 549/79; 562/429

(58) Field of Classification Search ................... 514/256, 514/406, 419, 438, 571; 544/335; 548/204, 548/469; 549/79; 562/429
See application file for complete search history.

(56) References Cited

U.S. PATENT DOCUMENTS

| | | | |
|---|---|---|---|
| 4,281,008 A | 7/1981 | Chamberlain et al. | |
| 4,499,299 A | 2/1985 | Bernstein et al. | |
| 4,546,194 A | 10/1985 | Mijano et al. | |
| 4,565,882 A | 1/1986 | Mijano et al. | |
| 4,665,203 A | 5/1987 | Mijano et al. | |
| 4,683,325 A | 7/1987 | Frenette et al. | |
| 4,686,235 A | 8/1987 | Chang et al. | |
| 4,841,076 A | 6/1989 | Kitagawa et al. | |
| 4,889,871 A | 12/1989 | Djuric et al. | |
| 4,935,529 A | 6/1990 | Gerwick | |
| 4,950,684 A | 8/1990 | Koszyk et al. | |
| 4,952,705 A | 8/1990 | Mijano et al. | |
| 4,959,361 A | 9/1990 | Walser | |
| 5,001,140 A | 3/1991 | Field et al. | |
| 5,219,883 A | 6/1993 | Koszyk et al. | |
| 5,273,999 A | 12/1993 | Cohen et al. | |
| 5,310,952 A | 5/1994 | Heveling et al. | |
| 5,457,124 A | 10/1995 | Cohen et al. | |
| 5,910,505 A | 6/1999 | Fleisch et al. | |
| 6,224,907 B1 | 5/2001 | Davar et al. | |
| 6,229,011 B1 | 5/2001 | Chen et al. | |

FOREIGN PATENT DOCUMENTS

| | | |
|---|---|---|
| WO | WO9118880 | 12/1991 |
| WO | WO9201675 | 2/1992 |
| WO | WO 95/15956 | 6/1995 |

OTHER PUBLICATIONS

Prostaglandins, Leukotrienes and Essential Fatty Acids 69, 2003, 123-134.
*Bioorganic & Medicinal Chemistry Letters* (1994), 4(24), 2883-8.
*Modern Arene Chemistry* 2002, 53-106.
J.Org.Chem.1997, 62,8215-8217.
Knochel, Chem. Rev. 1993, 93, 2117.
Klement, I., Tetrahedron 1996, 52, 7201.
Knochel, Tetrahedron 1998, 54, 8275.
Siegfried, J. Med. Chem. 2000, 43, 1670.
J. Org. Chem. 1970, 35, 244.
J. Org.Chem. 2003, 68, 8750.
Org. Lett. 2004, 6, 4587.
J. Am. Chem. Soc. 2006, 128, 2180.
J.Org.Chem. 1962, 27, 93.
Tetrahedron 2006, 62, 2357.
Labaudiniere, et al., J. Med. Chem. 35, pp. 4315-4324 (1992).
Valacer, D.J., Journal of the National Medical Association, vol. 91, No. 8, pp. 26S-39S (1999).
Marder, P. et al, *British Journal of Clinical Pharmacology*, 42:4, 457-464 (1996).

*Primary Examiner* — Deborah D Carr
(74) *Attorney, Agent, or Firm* — George W. Johnston; Dennis P. Tramaloni; Samuel H. Megerditchian

(57) ABSTRACT

Provided herein are compounds of the formula (I):

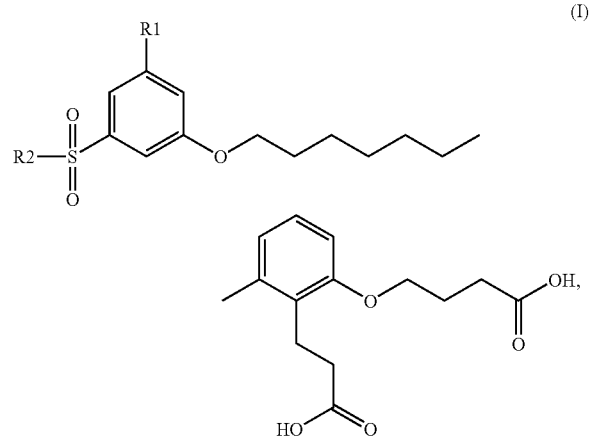

as well as pharmaceutically acceptable salts thereof, wherein the substituents are as those disclosed in the specification. These compounds, and the pharmaceutical compositions containing them, are useful for the treatment of diseases such as, for example, COPD.

12 Claims, No Drawings

LEUKOTRIENE B₄ INHIBITORS

PRIORITY TO RELATED APPLICATION(S)

This application claims the benefit of U.S. Provisional Application No. 61/034,307, filed Mar. 6, 2008, which is hereby incorporated by reference in its entirety.

FIELD OF THE INVENTION

The invention is directed to compounds of formula I:

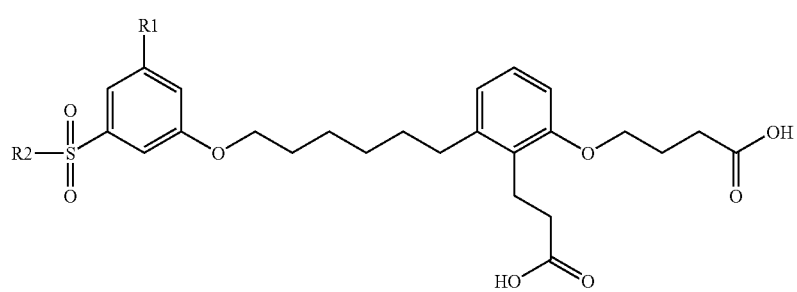

(1)

or pharmaceutically acceptable salts thereof. These compounds inhibit the interaction of leukotriene $B_4$ ($LTB_4$) pro-inflammatory lipid mediator binding to BLT-1 and BLT-2 receptors resulting in amelioration of disease states resulting from excessive inflammatory response, such as, for example, severe asthma and chronic obstructive pulmonary disease (COPD).

All documents cited or relied upon below are expressly incorporated herein by reference.

BACKGROUND OF THE INVENTION $LTB_4$ is a potent pro-inflammatory lipid mediator derived from arachidonic acid through the 5-lipoxygenase signaling pathway. $LTB_4$ is produced by multiple cell types such as neutrophils, monocytes, macrophages, keratinocytes, lymphocytes and mast cells. It functions as a chemoattractant and as an activator of neutrophil cells. It has been shown that $LTB_4$ effects its action through the agonism of G-protein coupled receptors BLT-1 and BLT-2. (Prostaglandins, Leukotrienes and Essential Fatty Acids 69, 2003, 123-134.)

$LTB_4$ is considered to be an important mediator of acute and chronic inflammatory diseases. Increased levels of $LTB_4$ have been detected in the lungs of patients with severe asthma and COPD. Thus, it is anticipated that an effective inhibitor of the action of $LTB_4$ and BLT-1 and -2 would provide effective therapy for the treatment of inflammatory conditions such as asthma and COPD.

A need exists in the art for $LTB_4$ inhibitors that have efficacy for the treatment of diseases such as COPD.

SUMMARY OF THE INVENTION

The present invention pertains to inhibitors of $LTB_4$. In a preferred embodiment, the invention provides for pharmaceutical compounds of the formula I:

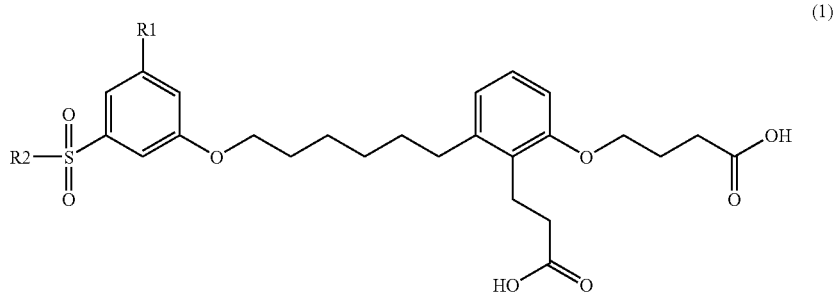

(1)

as well as pharmaceutically acceptable salts thereof, that are useful as inhibitors of $LTB_4$.

DETAILED DESCRIPTION

In an embodiment of the present invention, provided is a compound of formula (I):

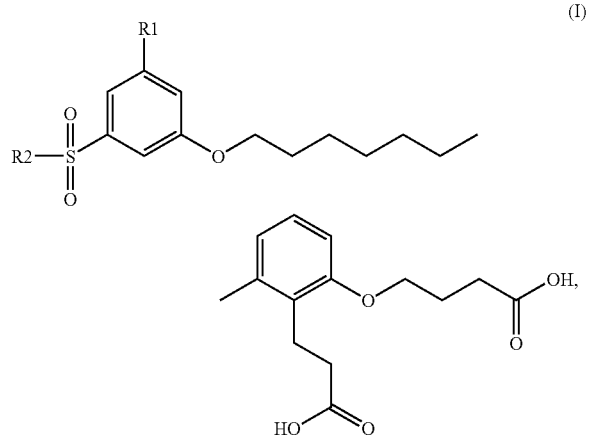

wherein:
R1 is
  -benzo[1,3]dioxol,
  -benzo[1,4]dioxin,
  -difluoro-benzo[1,3]dioxole,
  -indole, unsubstituted or substituted with lower alkyl,
  -cycloalkyl,
  -aryl, unsubstituted or mono-, di- or tri-substituted with halogen, hydroxy, alkoxy, lower alkyl, —CF3, —OCF3 or methanesulfonyl,
  -heteroaryl, unsubstituted or mono-, di- or tri-substituted with lower alkyl or hydroxy, and
  —N-aryl; and
R2 is -lower alkyl,
and pharmaceutically acceptable salts thereof.

In another embodiment of the present invention, provided is a pharmaceutical composition, comprising a therapeutically effective amount of a compound according to claim 1 or a pharmaceutically acceptable salt thereof and a pharmaceutically acceptable carrier.

In a further embodiment of the present invention, provided is a method of treating an inflammatory disease or disorder, comprising the step of administering a therapeutically effective amount of a compound according to claim 1 to a patient in need thereof.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "cycloalkyl" refers to a monovalent carbocyclic radical of three to seven, preferably three to six carbon atoms. This term is further exemplified by radicals such as cyclopropyl, cyclobutyl, cyclopentyl and cyclohexyl. In a preferred embodiment, the "cycloalkyl" moieties can optionally be substituted with one, two, three or four substituents, wherein each substituent is independently, for example, hydroxy, alkyl, alkoxy, halogen or amino, unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a cyclic alkyl ring, wherein one, two or three of the carbon ring atoms is replaced by a heteroatom such as N, O or S. Examples of heterocycloalkyl groups include, but are not limited to, morpholine, thiomorpholine, piperazine, piperidine and the like. The heterocycloalkyl groups may be unsubstituted or substituted.

The term "lower alkyl", alone or in combination with other groups, refers to a branched or straight-chain monovalent alkyl radical of one to six carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic monovalent mono- or polycarbocyclic radical, such as phenyl or naphthyl, preferably phenyl.

The term "heteroaryl," alone or in combination with other groups, means a monocyclic or bicyclic radical of 5 to 12 ring atoms having at least one aromatic ring containing one, two, or three ring heteroatoms selected from N, O, and S, the remaining ring atoms being C. One or two ring carbon atoms of the heteroaryl group may be replaced with a carbonyl group. The heteroaryl group described above may be substituted independently with one, two, or three substituents, preferably one or two substituents such as, for example, halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, amino $C_{1-6}$ alkyl, mono- or di-substituted amino-$C_{1-6}$ alkyl, nitro, cyano, acyl, carbamoyl, mono- or di-substituted amino, aminocarbonyl, mono- or di-substituted amino-carbonyl, aminocarbonyl $C_{1-6}$ alkoxy, mono- or di-substituted amino-carbonyl-$C_{1-6}$ alkoxy, hydroxy-$C_{1-6}$ alkyl, carboxyl, $C_{1-6}$ alkoxy carbonyl, aryl $C_{1-6}$ alkoxy, heteroaryl $C_{1-6}$ alkoxy, heterocyclyl $C_{1-6}$ alkoxy, $C_{1-6}$ alkoxycarbonyl $C_{1-6}$ alkoxy, carbamoyl $C_{1-6}$ alkoxy and carboxyl $C_{1-6}$ alkoxy, preferably halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, mono-$C_{1-6}$ alkyl substituted amino, di-$C_{1-6}$ alkyl substituted amino, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, nitro, carbamoyl, mono- or di-substituted amino-carbonyl, hydroxy-$C_{1-6}$ alkyl, carboxyl, $C_{1-6}$ alkoxy carbonyl and cyano.

The alkyl and aryl groups may be substituted or unsubstituted. Where substituted, there will generally be, for example, 1 to 3 substituents present, preferably 1 substituent. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, arloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The lower alkyl groups may be substituted or unsubstituted, preferably unsubstituted. Where substituted, there will generally be, for example, 1 to 3 substitutents present, preferably 1 substituent.

As used herein, the term "alkoxy" means alkyl-O—; and "alkoyl" means alkyl-CO—. Alkoxy substituent groups or alkoxy-containing substituent groups may be substituted by, for example, one or more alkyl groups.

As used herein, the term "halogen" means a fluorine, chlorine, bromine or iodine radical, preferably a fluorine, chlorine or bromine radical, and more preferably a fluorine or chlorine radical.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminium salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

The compounds of the present invention can be prepared by any conventional means. Suitable processes for synthesizing these compounds are provided in the Examples. Generally, compounds of formula I can be prepared according to the Schemes described below. The sources of the starting materials for these reactions are also described.

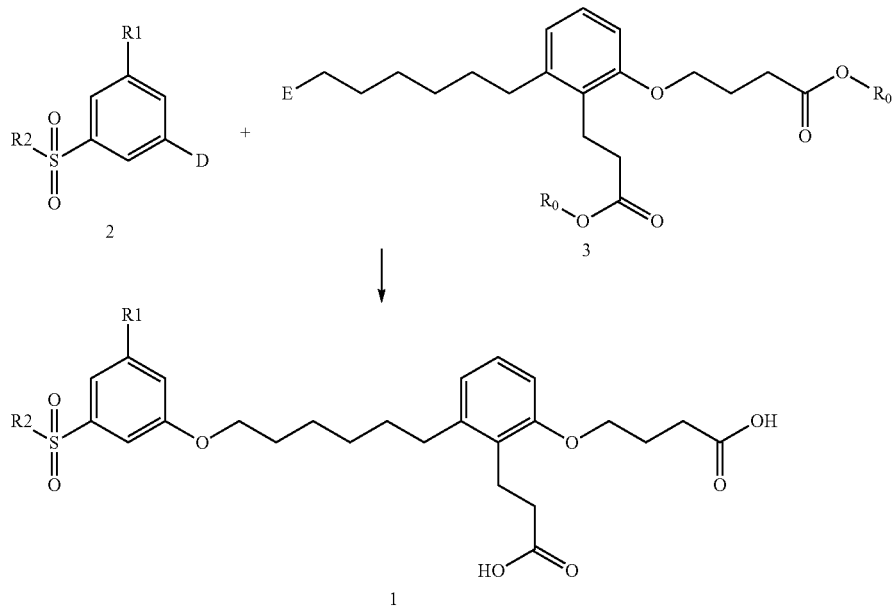

The compounds contained within this invention can be synthesized according to the following general synthetic strategies as shown below in Scheme 1. The synthesis of 1 may be effected by condensation of 3,4-[2-(2-carboxy-ethyl)-3-(6-E-hexyl)-phenoxy]-butyric acid, protected as a di-ester for R0=lower alkyl, preferably as a di-ethyl ester (R0=ethyl), and E is a leaving group, such as a halogen or mesylate with the fragment 2 wherein D is a nucleophile such as a hydroxyl group under standard conditions employed for the alkylation of phenols with primary halides or mesylates. Functional groups represented by symbol R1 being halogen, nitro, and amino group and can be transformed to an aryl, aryl ether, or amine moiety before or after coupling to 3 according to chemistry described in this invention.

A synthesis of 3 for E=Br and $R_0$=Et has been described in *Bioorganic & Medicinal Chemistry Letters* (1994), 4(24), 2883-8. A synthesis of 3 for E=Br and $R_0$=Et is also shown below in Schemes 2 and 3.

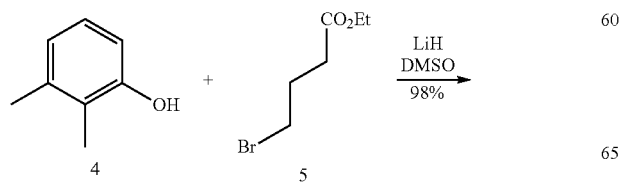

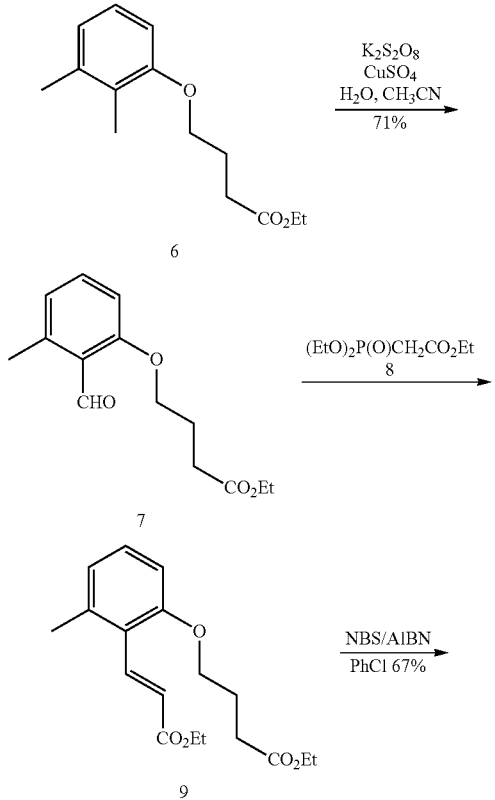

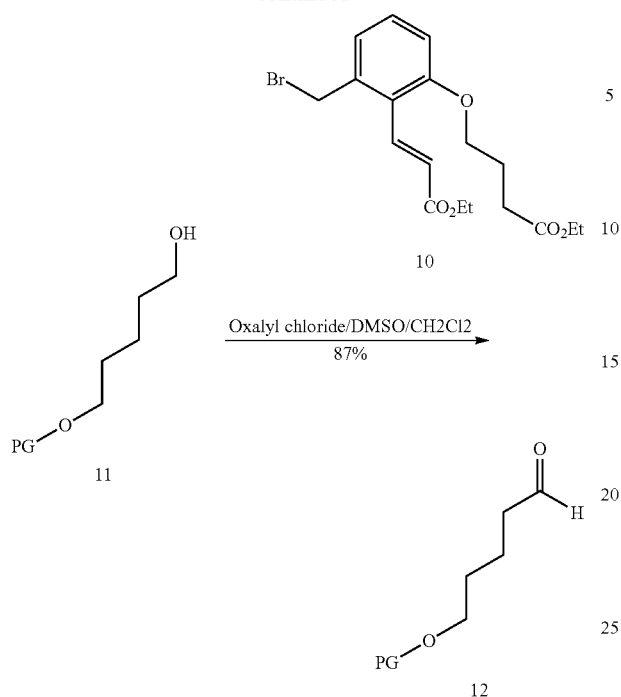

In Scheme 2, 2,3-dimethylphenol 4 is reacted with 4-bromo butyric acid ester 5 in presence of a base, preferably lithium hydride in aprotic solvent, preferably dimethylsulfoxide to obtain the dimethyl intermediate, 6. Then, the more reactive methyl group at 2-position of 6 is selectively oxidized to the corresponding aldehyde 7 using a oxidizing conditions, such as copper(II) sulfate pentahydrate and potassium persulfate in a mixed solvent systems, preferably water and acetonitrile. The two carbon chain ester moiety can be selectively introduced by a modified Horner-Emmons condensation conditions from aldehyde 7 and triethylphosphonoacetate 8 in the presence of a base such as sodium ethoxide in a protic solvents, preferably ethanol. Then, the benzylic bromination of 9 is effected with N-bromosuccinimide in the presence of 2,2'-azobisisobutyronitrile (AIBN) in an aprotic solvents such as carbon tetrachloride or chlorobenzene or benzene. The hydroxy protected 5-carbon chain aldehyde 12 can be obtained by oxidation of a mono protected pentane-1, 5-diol with any suitable oxidation conditions such as Swern oxidation or TEMPO oxidation, reactions well known to those skilled in the art. The protecting group on 11 and 12 can be any suitable protecting group for primary alcohols, for example t-butyldimethylsilyl group. Use and removal of protecting groups is well presented in the literature. For a leading reference, see P. G. M. Wuts and T. W. Greene in Green's Protective Groups in Organic Synthesis, Wiley and Sons, 2007.

Scheme 3

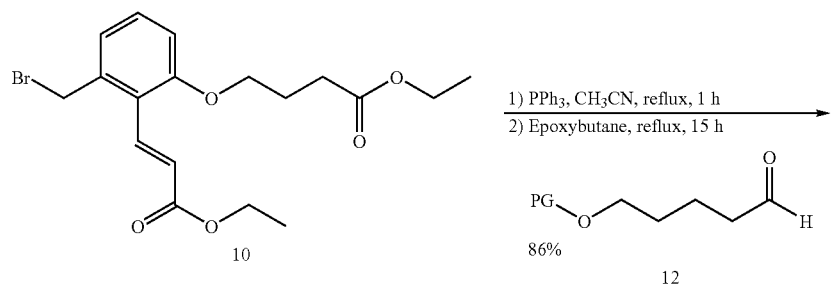

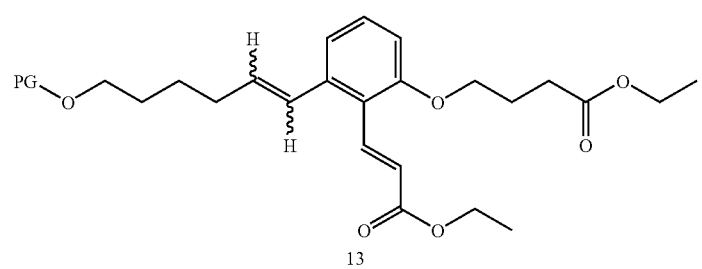

-continued

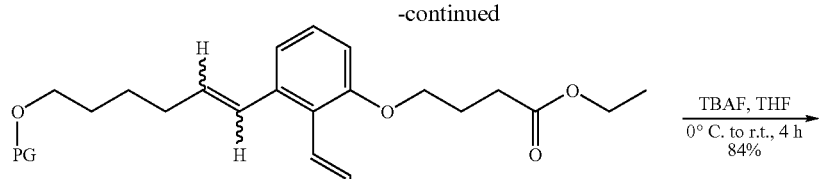
13

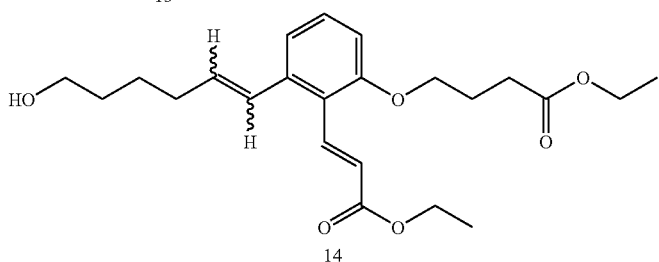
14

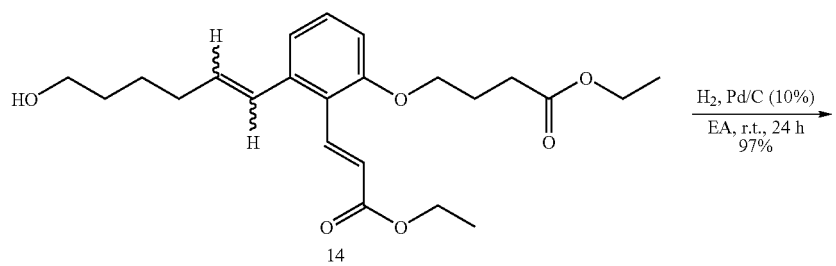
14

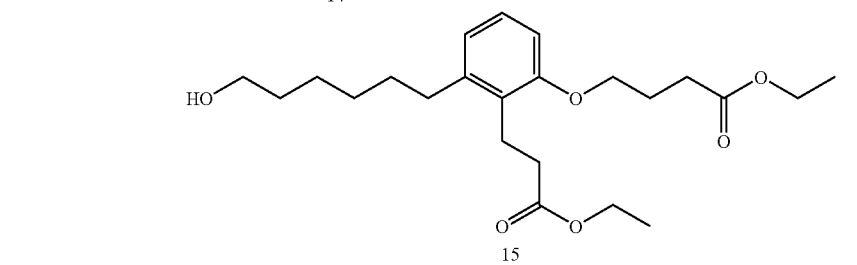
15

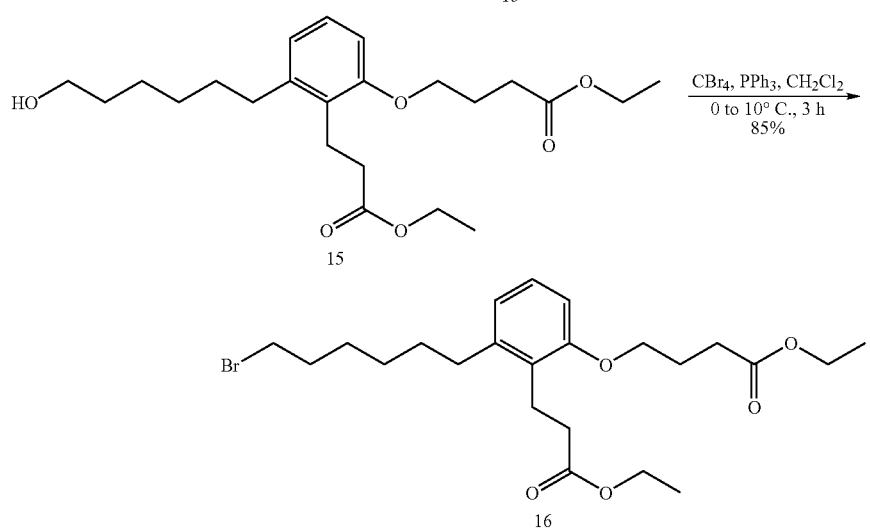
15

16

As shown in Scheme 3, a one-pot Wittig condensation reaction is conducted first by making an in situ Wittig salt from the benzylic bromide 10 and triphenylphosphine in acetonitrile and then the reaction of the resulting Wittig salt with the protected aldehyde 12 in 1,2-epoxybutane to obtain the olefinic intermediate 13 in a cis to trans ratio of ~1:3. The mixture of cis and trans compounds can be converted to the corresponding alkyl bromide intermediate 16 by removal of the protecting group, using for example tetrabutyl ammonium fluoride for the case wherein the protecting group is a t-butyldimethylsilyl group, hydrogenation of the double bonds, and conversion of the hydroxyl group to the bromide. These transformation are routine and well known to those skilled in the art.
Scheme 4: Method A
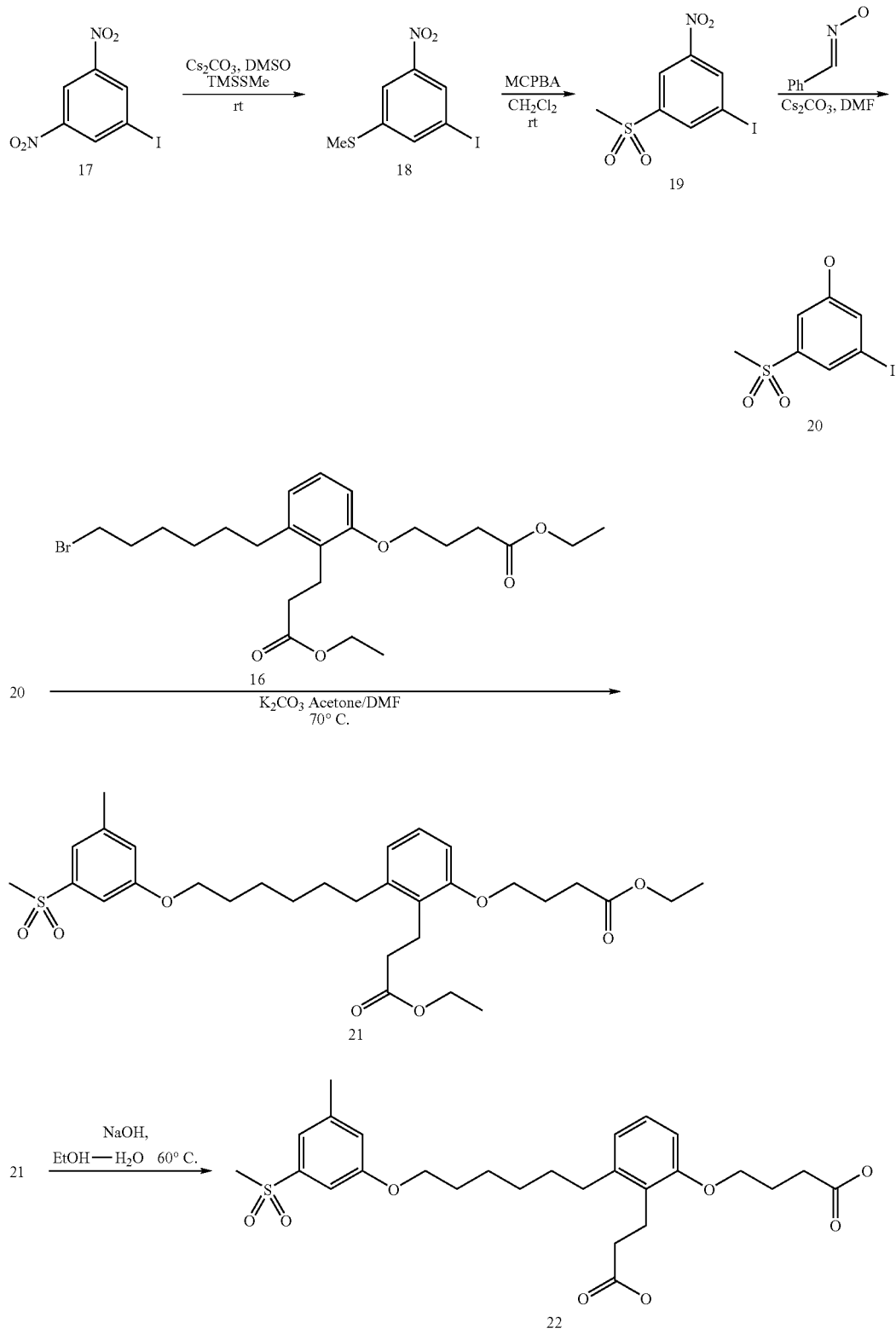

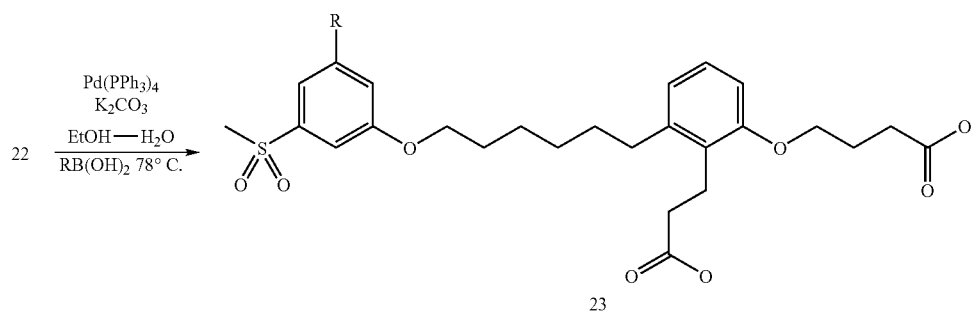

Target molecules 1 wherein R1 is an Aryl or heteroaryl group and R2=methyl can be synthesized as shown in Scheme 4. Starting with commercially available 1-iodo-3,5-dinitrobenzene 17, the thioanisole derivative 18 could be prepared using a combination of (methylthio)trimethylsilane (TMSSMe) and $Cs_2CO_3$ in DMSO. Nucleophilic aromatic substitution reactions ($S_NAr$) of nitroarenes with electron-withdrawing groups are well-known processes (*Tetrahedron* 1978, 34, 2057-2068.). The reaction proceeds in high yields using 1.2 equivalent of TMSSMe, 1.4 equivalent of $Cs_2CO_3$ and stirred at room temperature for overnight. There are several other methods available in the literature to prepare thioanisole derivatives. One method involves the nucleophilic aromatic substitution of electron-deficient aromatics using sodium thiomethoxide to introduce the methylthio moiety (*Org. Proc. Res. Dev.* 2003, 7, 385-392). Alternatively, an aryl bromide could also be treated with dimethyl disulfide and n-butyl lithium to generate the desired thioanisole derivative. (*Chem. Pharm. Bull.* 2005, 53, 965-973). The thiomethyl functionality in 18 can be converted to methyl sulfone 19. This transformation can be achieved using methods well known to one of ordinary skill in the art. Generally, meta-chloroperbenzoic acid in methylene chloride or 30% hydrogen peroxide and acetic acid as solvent are the preferred conditions for this reaction. A more direct route giving access to methyl sulfone derivatives consist of a nucleophilic substitution of aromatic nitro group with sodium methanesulfinate (*Helv. Chim. Acta* 1985, 68, 854-859). The required phenol 20 is produced by reaction of substituted nitrobenzene with benzaldoxime and cesium carbonate in DMF via a nucleophilic aromatic substitution. (*J. Org. Chem.* 1974, 39, 3343-3346). The O-arylaldoxime generated during the reaction is cleaved under basic conditions, yielding the phenol and benzonitrile. Potassium carbonate could also be used for this reaction. Coupling reaction between phenol 20 and alkyl bromide 16 can be accomplished in refluxing acetone or a mixture of acetone and N,N-dimethylformamide at a temperature about 75° C. in the presence of excess base such as potassium carbonate or cesium carbonate. The compound of structure 22 can therefore be prepared by hydrolyzing the diester 21. The saponification of ethyl ester can be conveniently accomplished using an excess of an alkali metal hydroxide, such as sodium hydroxide, potassium hydroxide or lithium hydroxide, in a suitable solvent such as a mixture of alcohol and water or tetrahydrofuran and water. The reaction can be carried out at a temperature ranging from 0° C. to 70° C. Finally, compounds of structure 23 can be obtained via the Suzuki coupling reaction. For a recent review, see *Tetrahedron* 2002, 58, 9633-9695.

Scheme 5: Method B

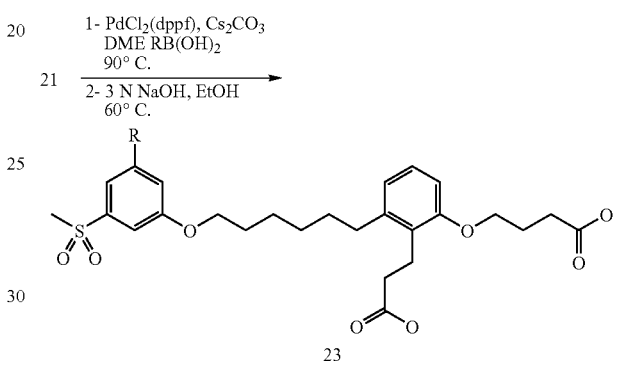

Alternatively, compounds of structure 23 can also be obtained from 21, as shown in scheme 5, method B. The Suzuki coupling reaction is performed under anhydrous conditions using [1,1'bis(diphenylphosphino) ferrocene] dichloropalladium(II) as catalyst prior to the saponification of the diethyl ester.

Scheme 6: Method C

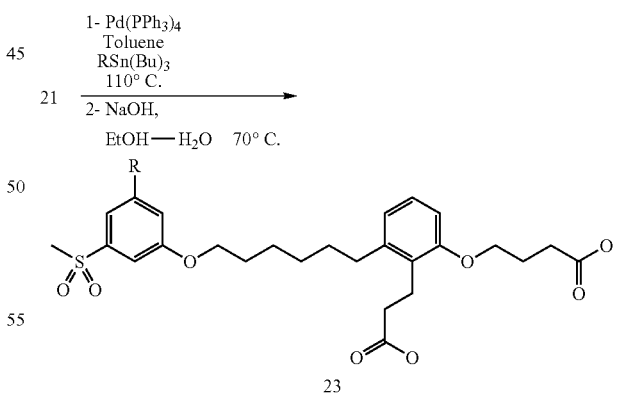

The method C is similar to method B except for the use of a Stille coupling reaction instead of the conditions and reagents necessary for a Suzuki coupling reaction. This reaction differs in part from the Suzuki reaction by the use of organostannanes in place of boronic acids and by the absence of base in the reaction mixture. For a recent review, see *Angew. Chem. Int. Ed.* 2004, 43, 4704-4734. In some instances, in this invention, further modifications can be applied to the Stille reaction product, such as desulfurization reaction using Raney nickel to remove a thiomethyl moiety. For the reduction of carbon-sulfur bonds of sulfides, Raney nickel is one of the most common reagent among others such as nickel(0) catalyst, nickel boride, dissolving metal, amalgam, and tin hydride. For reviews, see in "*Comprehensive Organic synthesis*", Vol. 8, p 853-870, Ed. By Trost, B. M; Fleming, I., Pergamon Press, Oxford, 1991. The saponification of ethyl ester is accomplished using standard conditions as described above.

Scheme 7: Method D

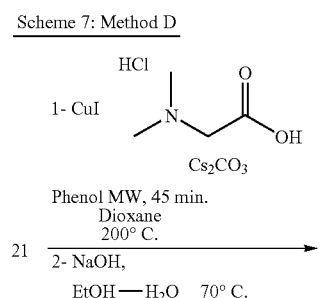

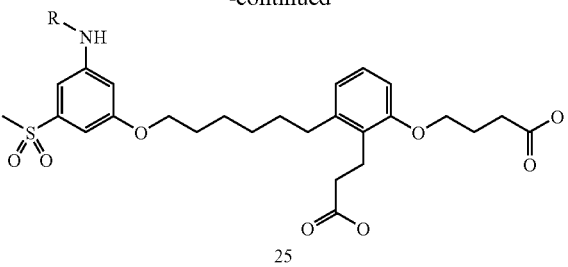

Target molecules 1 wherein R1 is an amine and R2=methyl can be synthesized according to method E as shown in Scheme 8. The Ullmann-type aryl amination reaction between iodide 21 and amines such as cyclopropyl amine and aniline was achieved using a procedure described in *Org. Lett.* 2003, 5, 2453-2455. Alternatively, Pd-catalyzed aromatic C—N bond formation can also be accomplished using procedures developed by Buchwald and Hartwig. For a review, see *Aldrichimica Acta*, 2006, 39,17-24. Thus, after saponification of the diethyl ester under standard conditions, compounds of structure 25 could be obtained.

Scheme 9: Method F

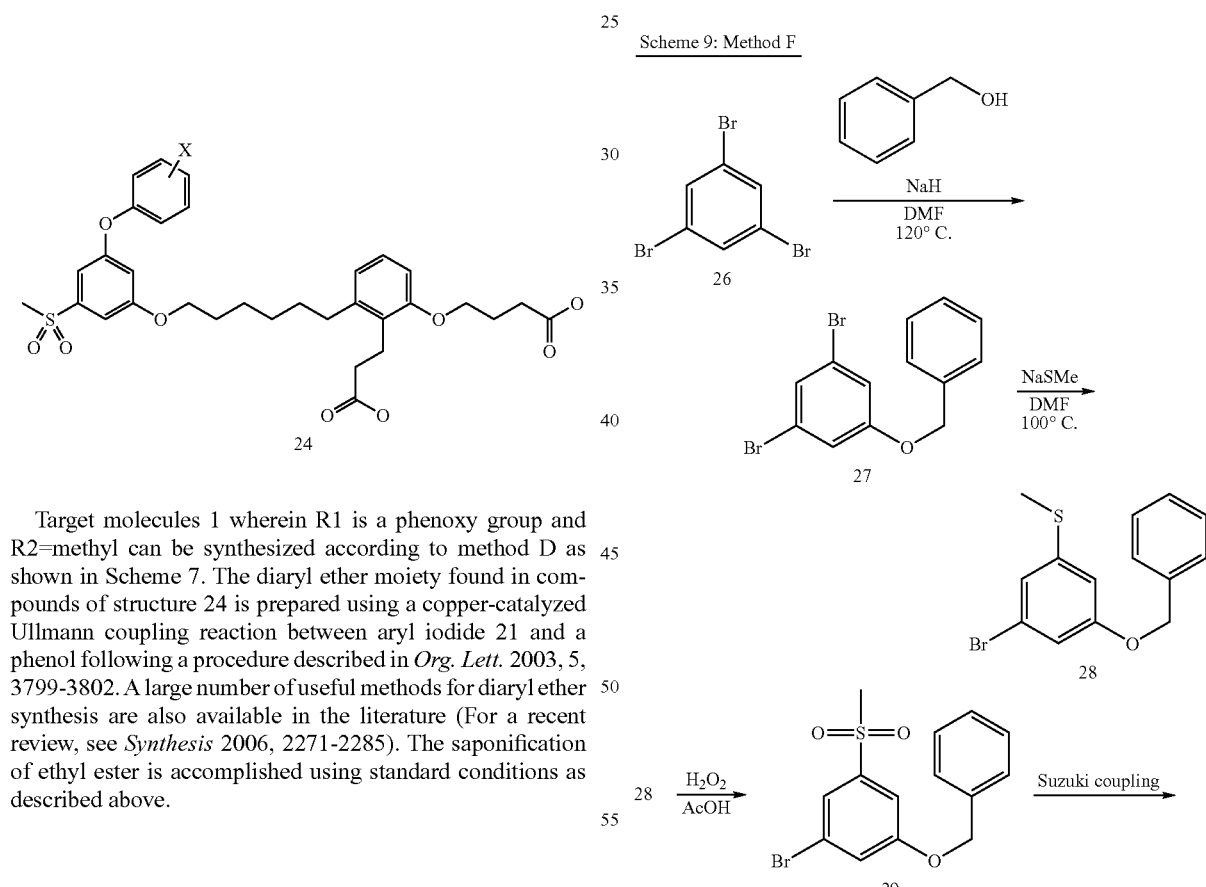

Target molecules 1 wherein R1 is a phenoxy group and R2=methyl can be synthesized according to method D as shown in Scheme 7. The diaryl ether moiety found in compounds of structure 24 is prepared using a copper-catalyzed Ullmann coupling reaction between aryl iodide 21 and a phenol following a procedure described in *Org. Lett.* 2003, 5, 3799-3802. A large number of useful methods for diaryl ether synthesis are also available in the literature (For a recent review, see *Synthesis* 2006, 2271-2285). The saponification of ethyl ester is accomplished using standard conditions as described above.

Scheme 8: Method E

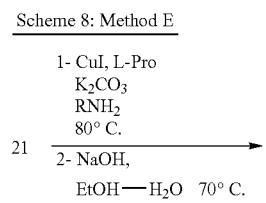

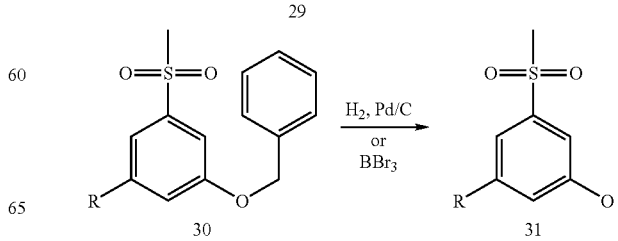

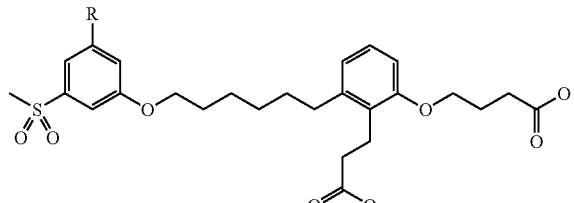

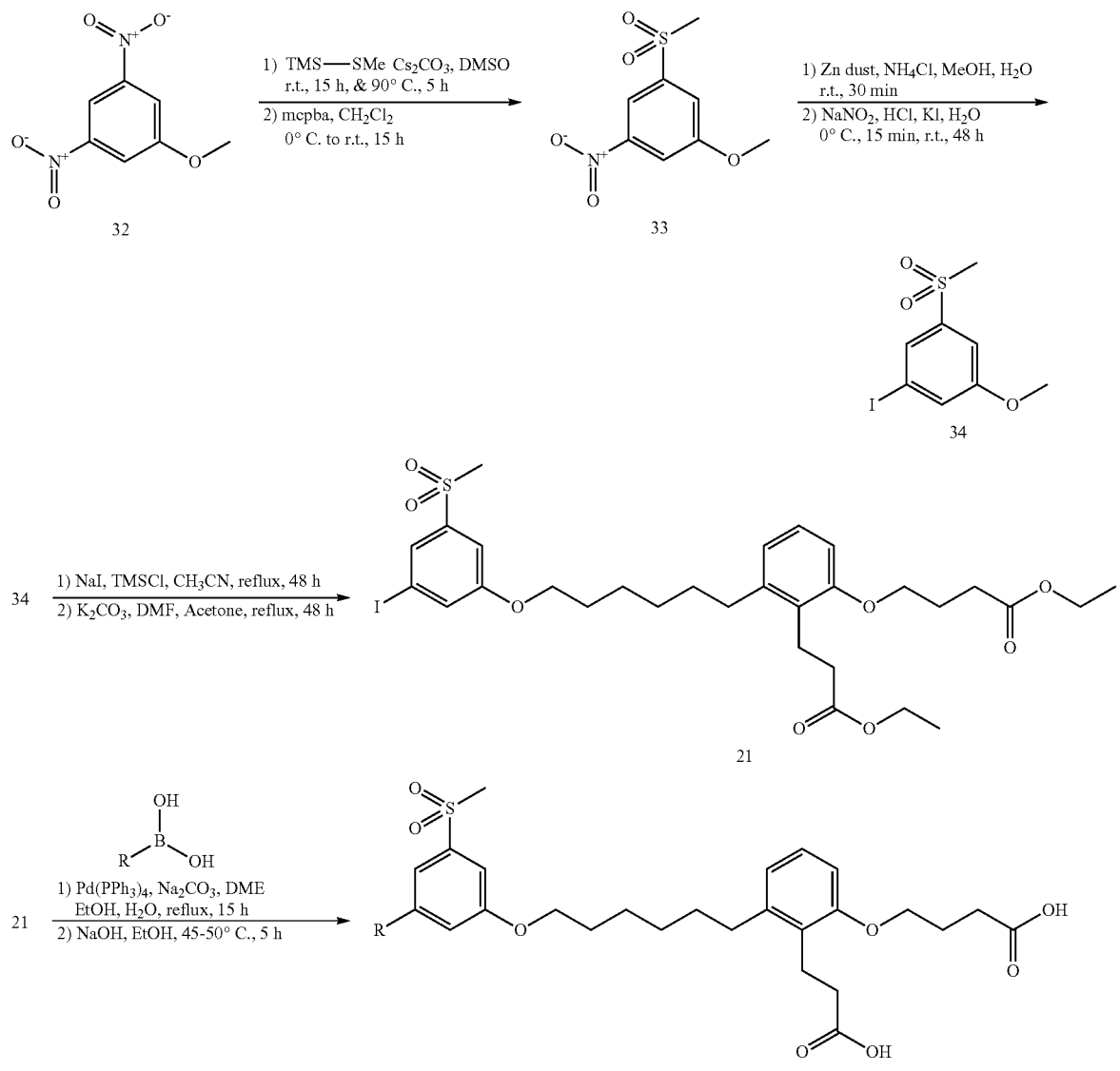

Compounds of structure 23 where R=Aryl, heteroaryl can be synthesized according to method F as described in scheme 9. In this method, a benzyloxy group is used as protecting group to mask the required phenol moiety for the coupling with alkyl bromide 16. After introduction of the sulfone moiety and aryl group, debenzylation is accomplished by catalytic hydrogenation using hydrogen gas over palladium catalyst absorbed on carbon in solvent such as methanol, ethyl acetate or tetrahydrofuran. Alternatively, boron tribromide can be used to cleave the carbon-oxygen bonds to release the phenol. Other methods for removal of the benzyl group are available as described in "Protective Groups in Organic Synthesis" by T. Greene and P. Wuts, third edition, John Wiley & Sons, Inc. pp. 266-269. Then the remaining two steps to prepare of compounds of formula 23 have been described in the previous methods.

As shown in scheme 10, compounds having a structure such as 23 can also be obtained using Method G. Starting from commercially available 3,5-dinitroanisole 32, one of the nitro group is selectively converted to the 3-nitro-5-methyl-sulfanylanisole using methylthiotrimethylsilane in the presence of a base, preferable cesium carbonate in a polar solvents like DMSO. The conversion of the 5-methylsulfanyl group to the corresponding 5-methylsulfonyl of compound 33 can be carried out using any oxidation conditions such as mcpba, hydrogen peroxide, or oxone, preferable mcpba in dichloromethane. Then, the other nitro group of compound 33 can be converted to the corresponding iodide derivative 34 in two steps using a milder reduction conditions such as zinc dust and ammonium chloride in a mixture of protic solvents such as methanol and water followed by diazotization conditions such as sodium nitrite and hydrochloric acid in water in the presence of a potassium iodide (see for example Lucas, H. J.; Kennedy, E. R. *Org. Synth. Coll. Vol, II* 1943, 351). Finally, the cleavage of methyl ether bond can be effectively performed using sodium iodide and chlorotrimethylsilane in acetonitrile to obtain the desired phenol which can be coupled to intermediate 16 using the same procedure described in previous methods. The remaining two steps to prepare of compounds of formula 23 have been already described.

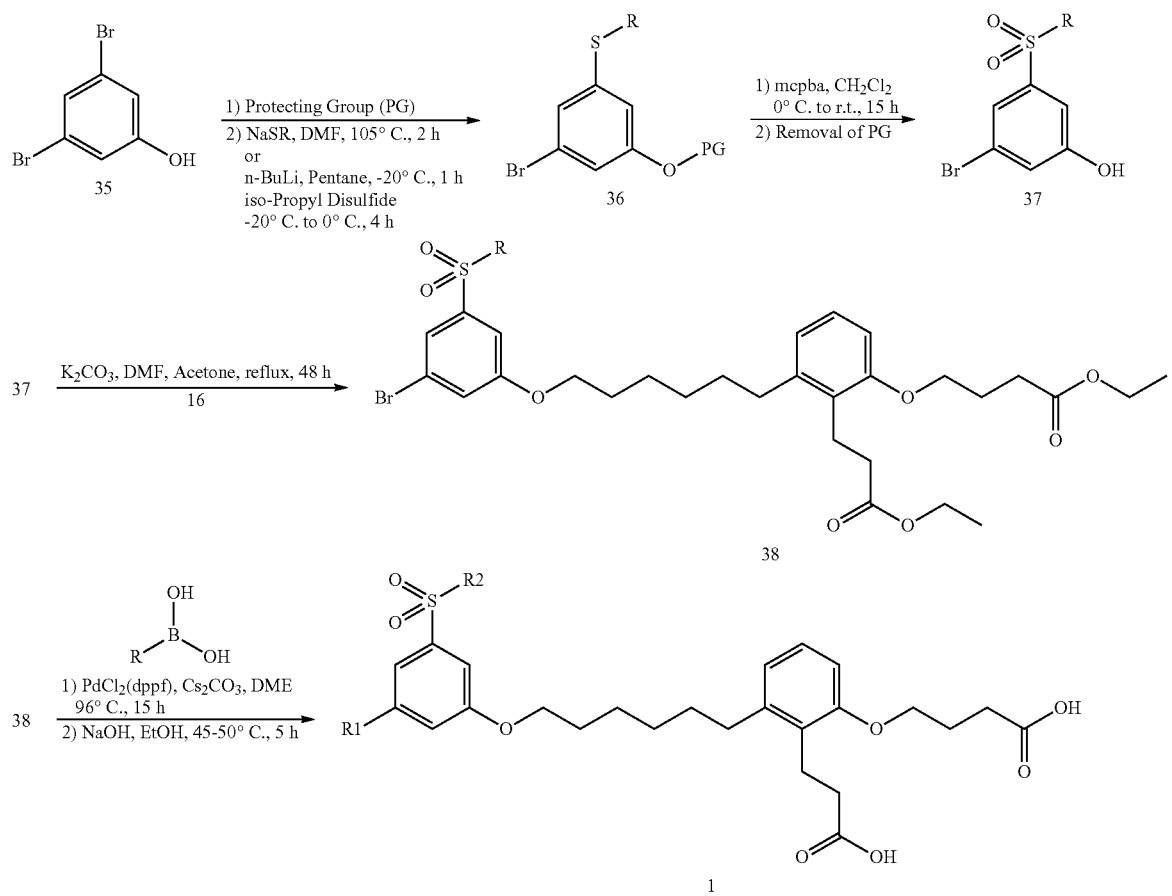

Target molecules 1 wherein R1 is an aryl or heteroaryl group and R2=lower alkyl can be synthesized according to method H as shown in Scheme 11. Starting from commercially available 3,5-dibromophenol 35, addition of protecting groups on the phenol moiety as well as their removal can be accomplished following procedures as described in "Protective Groups in Organic Synthesis" by T. Greene and P. Wuts, third edition, John Wiley & Sons, Inc. Protecting groups such as methyl, para-methoxybenzyl and methoxymethyl groups can be used. The alkylsulfanyl analogue 36 can be obtained using a sodium thioalkoxide in a polar solvents such as DMF at higher temperatures, preferable at 105° C. following a literature report (Michael, F. L. et al *Organic Process Research & Development* 2003, 7, 385-392) or an alkyl sulfide moiety is added following literature reported method (Morita, Y., Kashiwagi, A., Nakasuji, K. *J. Org. Chem.*, 1997, 62, 7464-7468). The remaining steps to prepare compounds of formula 1 have been already described.

Scheme 12

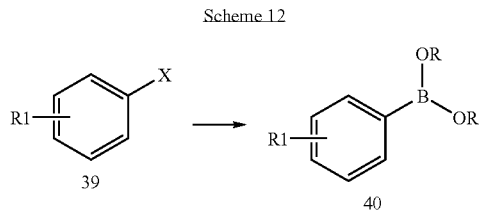

Substituted phenyl boronic acids (40, R=H) and boronic esters such as 4,4,5,5-tetramethyl-[1,3,2]dioxaborolane (40, R=—(C(CH$_3$)$_2$)$_2$—) useful in the preparation of compounds of this invention may be commercially available or they can be made by reactions that are well known in the field of organic synthesis. Aryl boronic acids and aryl boronic esters are formed by treatment of aryl halides 39 with an organometallic reagent such as n-butyl lithium followed by treatment with boron triisopropoxide or 4,4,4',4',5,5,5',5'-octamethyl-2,2'-bi-1,3,2-dioxaborolane followed by acidic work-up as is well known to those skilled in the art. (For an example in the literature, see Org. Process Res. Dev. 2004, 8, 201).

Commercially available boronic acids used in this procedure are listed below. The Available Chemicals Database (ACD) indicates the availability of greater than seven hundred commercially available aryl boronic acids. Some boronic acids useful for the preparation of compounds of the invention are listed below.

TABLE 1

Commercially available boronic acids
Boronic acid

3-CHLORO-PHENYLBORONIC ACID
PHENYLBORONIC ACID
2-CHLOROPHENYLBORONIC ACID
3-CHLORO-4-FLUOROPHENYLBORONIC ACID
3-METHYLPHENYLBORONIC ACID
1,4-BENZODIOXANEBORONIC ACID
3,4-DIFLUOROPHENYLBORONIC ACID
4-CHLOROPHENYLBORONIC ACID
4-CHLORO-3-FLUOROPHENYLBORONIC ACID
THIOPHENE-2-BORONIC ACID
2-FLUOROPHENYLBORONIC ACID
4-FLUORO-3-METHYLPHENYLBORONIC ACID
3-FLUOROPHENYLBORONIC ACID
THIOPHENE-3-BORONIC ACID
4-METHYL-3-THIOPHENEBORONIC ACID
4-METHOXYPHENYLBORONIC ACID
4-ETHOXYPHENYLBORONIC ACID
3-FLUORO-4-METHYLPHENYLBORONIC ACID
4-ETHYLPHENYLBORONIC ACID
2,3-DIHYDROBENZOFURAN-5-BORONIC ACID
3-METHOXYPHENYLBORONIC ACID
2-TRIFLUOROMETHOXYPHENYLBORONIC ACID
4-TRIFLUOROMETHOXYPHENYLBORONIC ACID
4-FLUOROPHENYLBORONIC ACID
3-FLUORO-4-METHOXYPHENYLBORONIC ACID
3,5-DIFLUOROPHENYLBORONIC ACID
1-CYCLOHEXEN-1-YL-BORONIC ACID
5-BENZO[1,3]DIOXOLEBORONIC ACID
1H-PYRAZOLE-4-BORONICACID
1H-INDOLE-5-BORONIC ACID
4-PYRIDYL-BORONIC ACID
3-PYRIDYL-BORONIC ACID
4-METHANESULFONYLPHENYLBORONIC ACID ACID
1-H-PYRAZOL-3-YLBORONIC ACID
4-FLUORO-3-HYDROXYPHENYLBORONIC ACID

TABLE 2

These boronic acids are also available from other suppliers that may not necessarily be listed in the ACD.

| | | |
|---|---|---|
| 3-Fluoro-6-(4,4,5,5-tetramethyl-[1,3,2]dioxaborolan-2-yl)pyridine | ATLANTIC SCIENTIFIC CO., INC., JERSEY CITY, NJ, | 791819-04-0 |
| Quinoline-2-boronic acid | LANCASTER | 745784-12-7 |
| 3-Chloro-6-(4,4,5,5-tetramethyl-[1,3,2]dioxaborolan-2-yl)pyridine | ATLANTIC SCIENTIFIC CO., INC., JERSEY CITY, NJ, | 652148-93-1 |
| 6-Chloropyridine-2-boronic acid pinacol ester | INTERCHIM, MONTLUCON, FRANCE | 652148-92-0 |
| Boronic acid, (2-methyl-4-pyrimidinyl)- | CHEMSTEP, TALENCE, FRANCE | 647853-31-4 |
| Boronic acid, (3-methoxy-2-pyridinyl)- | CHEMSTEP, TALENCE, FRANCE | 500707-34-6 |
| Boronic acid, (6-methoxy-2-pyridinyl)- | CHEMSTEP, TALENCE, FRANCE | 372963-51-4 |
| Boronic acid, (6-methyl-2-pyridinyl)- | CHEMSTEP, TALENCE, FRANCE | 372963-50-3 |
| Boronic acid, (5-methyl-2-pyridinyl)- | CHEMSTEP, TALENCE, FRANCE | 372963-49-0 |
| Boronic acid, (4-methyl-2-pyridinyl)- | CHEMSTEP, TALENCE, FRANCE | 372963-48-9 |
| Boronic acid, 2-pyridinyl- | CHEMSTEP, TALENCE, FRANCE | 197958-29-5 |

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad lithium. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as an "effective amount". For example, the dose of a compound of the present invention is typically in the range of about 1 to about 1000 mg per day.

The invention will now be further described in the Examples below, which are intended as an illustration only and do not limit the scope of the invention.

EXAMPLES

Reagents were purchased from Aldrich, Sigma, Maybridge, Advanced ChemTech, and Lancaster or other suppliers as indicated below and used without further purification. Reactions using microwave irradiation for heating were conducted using either a Personal Chemistry Emrys Optimizer System or a CEM Discovery System. The purification of multi-milligram to multi-gram scale was conducted by methods known know to those skilled in the art such as elution of silica gel flash column; preparative flash column purifications were also effected in some cases by use of disposal pre-packed multigram silica gel columns (RediSep) eluted with a CombiFlash system. Biotage™ and ISCO™ are also flash column instruments that may have been used in this invention for purification of intermediates.

For the purpose of judging compound identity and purity, LC/MS (liquid chromatography/mass spectroscopy) spectra were recorded using the following system. For measurement of mass spectra, the system consists of a Micromass Platform II spectrometer: ES Ionization in positive mode (mass range: 150-1200 amu). The simultaneous chromatographic separation was achieved with the following HPLC system: ES Industries Chromegabond WR C-18 3u 120 Å (3.2×30 mm) column cartridge; Mobile Phase A: Water (0.02% TFA) and Phase B: Acetonitrile (0.02% TFA); gradient 10% B to 90% B in 3 minutes; equilibration time of 1 minute; flow rate of 2 mL/minute. In some cases, ammonium acetate at 20 millimolar concentration was used as a modifier for effective ionization during preparative HPLC. In such cases, the ammonium salt was isolated.

For some separations, the use of super critical fluid chromatography may also be useful. Super critical fluid chromatography separations were performed using a Mettler-Toledo Minigram system with the following typical conditions: 100 bar, 30° C., 2.0 mL/min eluting a 12 mm AD column with 40% MeOH in super critical fluid $CO_2$. In the case of analytes with basic amino groups, 0.2% isopropyl amine was added to the methanol modifier.

Many compounds of Formula 1 were also purified by reversed phased HPLC, using methods well known to those skilled in the art. In some cases, preparative HPLC purification was conducted using PE Sciex 150 EX Mass Spec controlling a Gilson 215 collector attached to a Shimadzu preparative HPLC system and a Leap autoinjector. Compounds were collected from the elution stream using LC/MS detection in the positive ion detection: The elution of compounds from C-18 columns (2.0×10 cm eluting at 20 ml/min) was effected using appropriate linear gradation mode over 10 minutes of Solvent (A) 0.05% TFA/H2O and Solvent (B) 0.035% TFA/acetonitrile. For injection on to HPLC systems, the crude samples were dissolved in mixtures of methanol, acetonitrile and DMSO H-Cube™ (produced by Thales Nanotechnology) is a a continuous-flow hydrogenation reactor equipped with in situ hydrogen generation and a disposable catalyst cartridge CatCart™. The reaction mixture can be heated and pressurized up to 100° C. and 100 bar (1450 psi) respectively. Reaction scale can be varied from 10 mg to 100 g.

Compounds were characterized either by $^1$H-NMR using a Varian Inova 400 MHz NMR Spectrometer or a Varian Mercury 300 MHz NMR Spectrometer as well as by high resolution mass spectrometry using a Bruker Apex-II high-resolution 4.7T FT-Mass Spectrometer.

| LIST OF ABBREVIATIONS | |
|---|---|
| AIBN | 2,2'-azobisisobutyronitrile |
| Bu | butyl |
| DCE | 1,2-dichloroethane |
| DCM | dichloromethane |
| DIPEA | diisopropylethylamine |
| DMF | N,N-dimethylformamide |
| DMSO | dimethylsulfoxide |
| EtOAc | ethyl acetate |
| EtOH | ethyl alcohol |
| FCC | flash column chromatography |
| h | hour |
| HPLC | high pressure liquid chromatography |
| HRMS | high resolution mass spectra |
| LRMS | low resolutiom mass spectra |
| LC | liquid chromatography |
| L-Pro | L-proline |
| MCPBA | meta-chloroperoxybenzoic acid |
| MeOH | methyl alcohol |
| MW | microwave |
| NIS | N-iodosuccinimide |
| NBS | N-bromosuccinimide |
| NMP | 1-methyl-2-pyrrolidinone |
| PdCl$_2$(dppf) | [1,1'-Bis(diphenylphosphino)ferrocene]dichloropalladium(II) |
| PG | protecting group |
| PyBroP | bromo-tris-pyrrolidino-phosphonium hexafluorophosphate |
| rt | room temperature |
| TBAF | tetrabutylammonium fluoride |
| TBDMS | tert-butyl-dimethylsilyl |
| TBTU | 2-(1H-benzotriazole-1-yl)-1,1,3,3-tetramethyluronium tetrafluoroborate |
| TMS | trimethylsilyl |
| TMSSMe | (methylthio)trimethylsilane |
| TEA | triethylamine |
| TEMPO | 2,2,6,6-tetramethylpiperidine-1-oxyl |
| TFA | trifluoroacetic acid |
| THF | tetrahydrofuran |

I. Preparation of Preferred Intermediates

Preparation of 4-[3-(6-bromo-hexyl)-2-(2-ethoxycarbonyl-ethyl)-phenoxy]-butyric Acid Ethyl Ester

1) Preparation of 4-(2,3-dimethyl-phenoxy)-butyric Acid Ethyl Ester

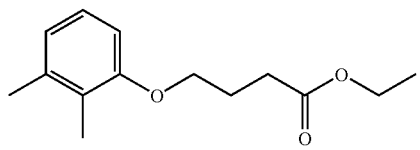

To a solution of 2,3-dimethylphenol (25 g, 204 mmol) in DMSO (205 mL) was added 4-bromo-butyric acid ethyl ester (40.96 g, 210 mmol) and lithium hydride (2.0 g, 250 mmol) at room temperature. The resulting light brown solution was stirred for 2 days. Then, the reaction mixture was cooled to 0° C. and water (200 mL) was added slowly. The organic compound was extracted into hexanes (2×200 mL). The combined organic extracts were washed with brine solution (150 mL) and the organic solution was dried over anhydrous magnesium sulfate. Filtration of the drying agent and the removal of the solvent gave light brown oil. The crude mixture was purified by using a Biotage™ (40 L) column chromatography eluting with 5% ethyl acetate in hexanes to isolate 4-(2,3-dimethyl-phenoxy)-butyric acid ethyl ester (45.32 g, 94%) as a colorless oil: ES(+)-HRMS m/e calculated for $C_{14}H_{20}O_3$ (M+)$^+$ 236.1412, found 236.1419.

2) Preparation of 4-(2-formyl-3-methyl-phenoxy)-butyric Acid Ethyl Ester

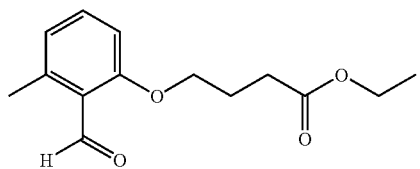

A mixture of copper(II) sulfate pentahydrate (21.98 g, 88.06 mmol) and potassium persulfate (71.42 g, 264 mmol) in water (396 mL) was heated to 63-65° C. to obtain a blue colored solution. Then, a solution of 4-(2,3-dimethyl-phenoxy)-butyric acid ethyl ester (20.81 g, 88.06 mmol) in acetonitrile (220 mL) was added at the above temperature. The resulting light green solution was refluxed for 40 minutes. Then, the reaction mixture was cooled to ~5° C. in order to precipitate most of the inorganic solids. The resulting solids were collected by filtration and the solid cake was washed with dichloromethane (1.0 L). The two layers of filtrate were separated and the aqueous layer was extracted with dichloromethane (200 mL). The combined organic extracts were washed with brine solution (150 mL) and the organic solution was dried over anhydrous magnesium sulfate. Filtration of the drying agent and the removal of the solvent gave a brown oil. The crude mixture was purified by using a Biotage™ (40 L) column chromatography eluting with 5-10% ethyl acetate in hexanes to obtain 4-(2-formyl-3-methyl-phenoxy)-butyric acid ethyl ester (45.32 g, 94%) as a colorless oil: EI(+)-HRMS m/e calculated for $C_{14}H_{18}O_4$ (M+)$^+$ 250.1205, found 250.1202.

3) Preparation of 4-[2-((E)-2-ethoxycarbonyl-vinyl)-3-methyl-phenoxy]-butyric Acid Ethyl Ester

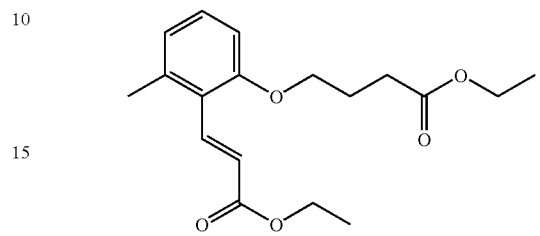

Sodium metal spheres (1.6 g, 69.6 mmol) were added to ethanol (100 mL) with stirring at room temperature under nitrogen atmosphere over 15 min. An exothermic reaction occurred and the mixture was stirred for another 15 min to form sodium ethoxide. After cooling to room temperature, triethylphosphonoacetate (14.7 mL, 73.4 mmol) and 4-(2-formyl-3-methyl-phenoxy)-butyric acid ethyl ester (13.25 g, 52.9 mmol) were added sequentially. During the addition of 4-(2-formyl-3-methyl-phenoxy)-butyric acid ethyl ester, the color of the solution turned brown and the temperature increased to ~55° C. The resulting brown solution was stirred for 2 days at room temperature. Then, the reaction mixture was diluted with water (150 mL) and stirred for 1 h. Then, the organic compound was extracted into hexanes (3×100 mL). The combined organic extracts were washed with brine solution (150 mL) and the organic solution was dried over anhydrous magnesium sulfate. Filtration of the drying agent and the removal of the solvent gave a light yellow oil. The crude oil was dissolved in hexanes (~50 mL) and treated with charcoal and heated gently with a heat gun. After cooling to room temperature, the charcoal was filtered-off and the filtrate was removed under vacuum to give 4-[2-((E)-2-ethoxycarbonyl-vinyl)-3-methyl-phenoxy]-butyric acid ethyl ester (13.25 g, 78%) as colorless oil: EI(+)-HRMS m/e calculated for $C_{18}H_{24}O_5$ (M+)$^+$ 320.1624, found 320.1626.

4) Preparation of 4-[3-bromomethyl-2-((E)-2-ethoxycarbonyl-vinyl)-phenoxy]-butyric Acid Ethyl Ester

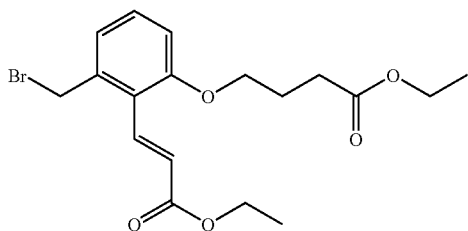

To a solution of 4-[2-((E)-2-ethoxycarbonyl-vinyl)-3-methyl-phenoxy]-butyric acid ethyl ester (8.0 g, 25.0 mmol) in chlorobenzene (190 mL) were added N-bromosuccinimide (6.67 g, 37.5 mmol) and 2,2'-azobisisobutyronitrile (AIBN) (591 mg, 3.6 mmol) at room temperature. Then, the solution was heated to 85° C. and stirred for 1 h. Then, the reaction mixture was cooled to room temperature and diluted with water (100 mL). Then, the organic compound was extracted into hexanes (3×100 mL). The combined organic extracts were washed with brine solution (150 mL) and the organic solution was dried over anhydrous magnesium sulfate. Filtration of the drying agent and the removal of the solvent gave a crude oil. The crude oil was purified by using a Biotage (40 L) column eluting with 15-25% ethyl acetate in hexanes to isolate 4-[3-bromomethyl-2-((E)-2-ethoxycarbonyl-vinyl)-phenoxy]-butyric acid ethyl ester (7.11 g, 71%) as a low melting solid: ES(+)-HRMS m/e calculated for $C_{18}H_{23}BrO_5$ (M+Na)$^+$ 421.0621, found 421.0621.

5) Preparation of 5-(tert-butyl-dimethyl-silanyloxy)-pentanal

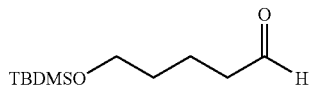

To a solution of 5-(tert-butyl-dimethyl-silanyloxy)-pentanol (16.8 mmol, 3.66 g) in dichloromethane (30 mL) were added water (5.6 mL), potassium bromide (1.7 mmol, 202 mg), n-tetrabutylammonium hydrogensulfate (0.84 mmol, 290 mg), and TEMPO (30 mg) at room temperature. The resulting light brown solution was cooled to ~5° C. and a solution of sodium hypochlorite (19.3 mmol, 30 mL, 5%) was added dropwise at this temperature. After addition of half of the sodium hypochlorite solution, solid potassium carbonate (300 mg) was added to maintain the reaction mixture basic. Then, the remaining sodium hypochlorite solution was added at 5-10° C. By this point, a precipitate had formed and the reaction mixture was stirred for another 1 h at ~10-15° C. Then, water (100 mL) was added and the resulting solution was extracted into diethyl ether (2×100 mL). The combined organic extracts were washed with brine solution (150 mL) and the organic layer was dried over anhydrous magnesium sulfate. Filtration of the drying agent and the removal of the solvent gave 5-(tert-butyl-dimethyl-silanyloxy)-pentanal (3.32 g, 91%) as a light brown oil: ES(+)-HRMS m/e calculated for $C_{11}H_{24}O_2Si$ (M+H)$^+$ 217.1619, found 217.1619.

6) Preparation of 4-[3-[6-(tert-butyl-dimethyl-silanyloxy)-hex-1-enyl]-2-((E)-2-ethoxycarbonyl-vinyl)-phenoxy]-butyric Acid Ethyl Ester

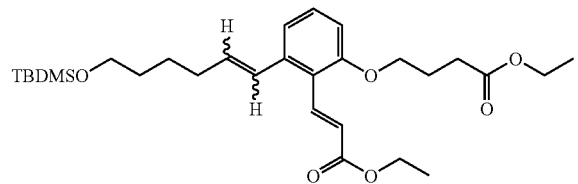

A solution of 4-[3-bromomethyl-2-((E)-2-ethoxycarbonyl-vinyl)-phenoxy]-butyric acid ethyl ester (2.0 mmol, 798 mg) and triphenylphosphine (2.2 mmol, 577 mg) in acetonitrile (12 mL) was heated to reflux for 1 h under nitrogen atmosphere. Then, it was cooled to room temperature and a solution of 5-(tert-butyl-dimethyl-silanyloxy)-pentanal (2.8 mmol, 606 mg) in 1,2-epoxybutane (22 mL) was added at room temperature and the mixture was again heated to reflux for 15 h. During this period, the mixture first turned to a brick red color and at the end of the reaction it had become a pale yellow solution. Then, the reaction mixture was cooled to room temperature and the solvent was removed under vacuum. The residue was dissolved in a solution of ethyl acetate and hexanes (1:3, 150 mL) and the resulting cloudy solution was washed with a mixture of methanol and water (2:1, 225 mL). The aqueous layer was extracted one more time with ethyl acetate and hexanes (1:3, 50 mL). The combined organic extracts were washed with brine solution (150 mL) and the organic solution was dried over anhydrous magnesium sulfate. Filtration of the drying agent and the removal of the solvent gave light brown oil. The crude mixture was purified by using a Biotage™ (40 L) column chromatograph eluting with 5 and 15% ethyl acetate in hexanes to obtain the desired 4-[3-[6-(tert-butyl-dimethyl-silanyloxy)-hex-1-enyl]-2-((E)-2-ethoxycarbonyl-vinyl)-phenoxy]-butyric acid ethyl ester (760 mg, 74%) as a colorless oil: ES(+)-HRMS m/e calculated for $C_{29}H_{46}O_6Si$ (M+Na)$^+$ 541.2956, found 541.2953.

7) Preparation of 4-[3-[6-(tert-butyl-dimethyl-silanyloxy)-hexyl]-2-(2-ethoxycarbonyl-ethyl)-phenoxy]-butyric Acid Ethyl Ester

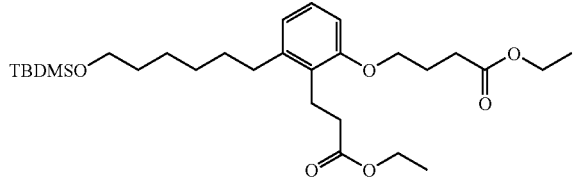

To a solution of 4-[3-[6-(tert-butyl-dimethyl-silanyloxy)-hex-1-enyl]-2-((E)-2-ethoxycarbonyl-vinyl)-phenoxy]-butyric acid ethyl ester (0.977 mmol, 507 mg) in ethyl acetate (10 mL) was added 10% palladium on carbon (350 mg) at room temperature. The resulting black mixture was stirred in the presence of atmospheric hydrogen gas in a balloon for 36 h at room temperature. Then, the catalyst was removed by filtration using a filter paper and the residue was washed with hot ethyl acetate (~60 mL). The filtrate was concentrated in vacuo and the resulting residue was dried under high vacuum to obtain 4-[3-[6-(tert-butyl-dimethyl-silanyloxy)-hexyl]-2-(2-ethoxycarbonyl-ethyl)-phenoxy]-butyric acid ethyl ester (438 mg, 86%) as a colorless oil: ES(+)-HRMS m/e calculated for $C_{29}H_{50}O_6Si$ (M+Na)$^+$ 545.3269, found 545.3267.

8) Preparation of 4-[2-(2-ethoxycarbonyl-ethyl)-3-(6-hydroxy-hexyl)-phenoxy]-butyric Acid Ethyl Ester

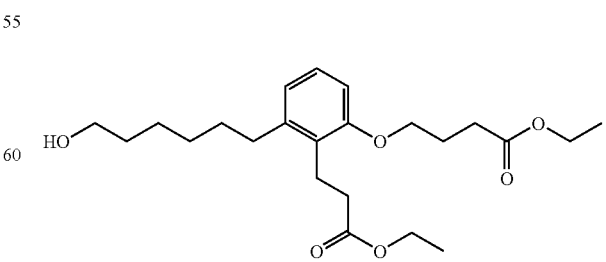

To a solution of 4-[3-[6-(tert-butyl-dimethyl-silanyloxy)-hexyl]-2-(2-ethoxycarbonyl-ethyl)-phenoxy]-butyric acid ethyl ester (0.837 mmol, 438 mg) in THF (12 mL) was added a solution of n-tetrabutyl ammonium fluoride (1.25 mmol, 1.25 mL, 1.0M) in THF at 0° C. Then, the resulting colorless solution was allowed to warm to room temperature in 2 h and the mixture was stirred for another 2 h at room temperature before being diluted with water (~50 mL). The organic compound was extracted into ethyl acetate (2×50 mL) and the combined extracts were washed with brine solution (100 mL). The organic solution was dried over anhydrous magnesium sulfate and the filtrate was removed under vacuum after filtration of the drying agent. The crude residue was dried further under high vacuum and the desired 4-[2-(2-ethoxy-carbonyl-ethyl)-3-(6-hydroxy-hexyl)-phenoxy]-butyric acid ethyl ester (342 mg, 99%) was isolated as a colorless oil: ES(+)-HRMS m/e calculated for $C_{23}H_{36}O_6$ (M+Na)$^+$ 431.2404, found 431.2404.

9) Preparation of 4-[3-(6-bromo-hexyl)-2-(2-ethoxy-carbonyl-ethyl)-phenoxy]-butyric Acid Ethyl Ester

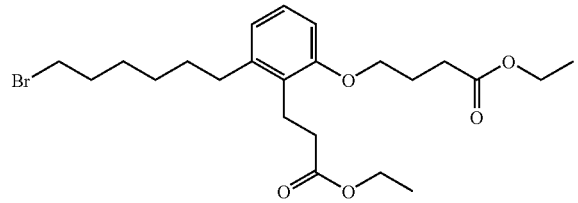

To a solution of 4-[2-(2-ethoxycarbonyl-ethyl)-3-(6-hydroxy-hexyl)-phenoxy]-butyric acid ethyl ester (0.85 mmol, 349 mg) and carbon tetrabromide (1.26 mmol, 423 mg) in dichloromethane (10 mL) was added triphenylphosphine (1.07 mmol, 281 mg) at ~0° C. The resulting colorless solution was stirred for 3 h at 5-10° C. Then, the solvent was removed under vacuum and the crude was tried to dissolve in a mixture of ethyl acetate and hexanes (1:3, 50 mL). As a result, a cloudy solution containing some precipitate was formed and the cloudy solution was transferred into a separatory funnel and was washed with a mixture of methanol and water (2:1, 150 mL). The aqueous layer was extracted one more time with ethyl acetate and hexanes (1:3, 50 mL). The combined organic extracts were washed with brine solution (100 mL) and the organic solution was dried over anhydrous magnesium sulfate. Filtration of the drying agent and the removal of the solvent gave a colorless oil which was purified by using a Biotage™ (40M) column chromatography eluting with 10% ethyl acetate in hexanes to obtain the desired 4-[3-(6-bromo-hexyl)-2-(2-ethoxycarbonyl-ethyl)-phenoxy]-butyric acid ethyl ester (350 mg, 87.5%) as a colorless oil: ES(+)-HRMS m/e calculated for $C_{23}H_{35}BrO_5$ (M+Na)$^+$ 493.1560, found 493.1560.

II. Preparation of Preferred Compounds

Method A

Step 1: 1-Iodo-3-methylsulfanyl-5-nitro-benzene

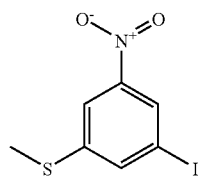

To a solution of 1-iodo-3,5-dinitrobenzene (15 g, 51 mmole) in 150 mL of DMSO trimethyl(methylthio)silane (10 mL, 70.6 mmol) was added slowly. The resulting reaction mixture turned purple at this point. Cesium carbonate 99.9% (23.13 g, 71.4 mmol) was then added. After stirring at room temperature for 18 h, the reaction mixture was diluted with 150 mL of ether, washed with 400 mL of saturated sodium bicarbonate solution and 150 mL of brine. The combined organic phase were then dried over sodium sulfate, filtered and concentrated under reduced pressure to afford 1-iodo-3-methylsulfanyl-5-nitro-benzene as a yellow solid. The crude material was used in the next step without further purification. HR-EI(+) m/e calcd for $C_7H_6NO_2SI$ (M+) 294.9164, found 294.9164.

Step 2: 1-Iodo-3-methanesulfonyl-5-nitro-benzene

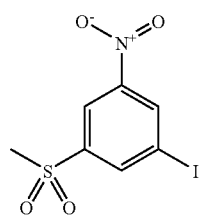

To a solution of 1-iodo-3-methylsulfanyl-5-nitro-benzene (51 mmole) in 600 mL of methylene chloride, meta-chloroperbenzoic acid (26.31 g, 153 mmole) was added and the reaction mixture stirred at room temperature for 3 h. 600 mL of a saturated sodium bicarbonate solution was added and the organic phase was extracted. (extraction with saturated sodium bicarbonate solution was repeated twice to ensure the complete removal of any residual meta-chloro benzoic acid). The aqueous phase wash washed with another 200 mL of methylene chloride. The combined organic phases were dried over sodium sulfate and evaporated under reduced pressure. The crude yellow solid was then recrystallized in hot methylene chloride (150 mL). The solid was filtered and washed with hexane to afford 12.6 g (76%) of 1-iodo-3-methanesulfonyl-5-nitro-benzene as a light yellow solid. HR-EI(+) m/e calcd for $C_7H_6NO_4SI$ (M+) 326.9062, found 326.9059.

Step 3: 3-Iodo-5-methanesulfonyl-phenol

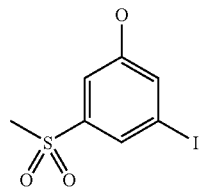

To a solution of syn-benzaldehyde oxime (3.71 g, 30.6 mmol) in DMF (80 mL) was added cesium carbonate (19.9 g, 61.3 mmol) and heated to 90° C. for 1-2 min before a solution of 1-iodo-3-methanesulfonyl-5-nitro-benzene (5.0 g, 15.3 mmol) in DMF (80 mL) was added. The resulting dark brown solution was stirred at 90° C. for 15 h. The reaction mixture was then cooled down and diluted with EtOAc and washed with 10% HCl. The organic phase was then washed again with brine. The combined organic extracts were dried over sodium sulfate and evaporated under reduced pressure to obtain a crude brown oil which was purified on ISCO column (330 g). The desired compound was eluted with 70% EtOAc-Hexanes. The desired fractions were combined and evaporated under reduced pressure to afford 2.5 g (55%) of 3-iodo-5-methanesulfonyl-phenol as an orange solid. HR-ES(+) m/e calcd for $C_7H_7O_3SI$ (M+H)$^+$ 298.9234, found 298.9234.

Step 4: 4-{2-(2-Ethoxycarbonyl-ethyl)-3-[6-(3-iodo-5-methanesulfonyl-phenoxy)-hexyl]-phenoxy}-butyric Acid Ethyl Ester

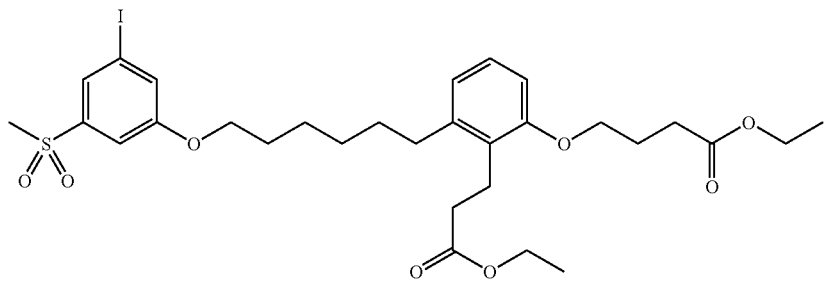

To a solution of 4-[3-(6-bromo-hexyl)-2-(2-ethoxycarbonyl-ethyl)-phenoxy]-butyric acid ethyl ester (3.79 g, 8.05 mmol), 3-iodo-5-methanesulfonyl-phenol (2.0 g, 6.71 mmol) in dimethylformamide (40 mL) and acetone (80 mL) was added potassium carbonate (9.25 g, 67.1 mmol). The resulting suspension was heated at 70° C. for 24 h. Then, the reaction mixture was cooled to room temperature, diluted with EtOAc and washed with 10% HCl and water. Then, the combined organic extracts were washed with brine. The organic layers were dried over anhydrous sodium sulfate and concentrated under reduced pressure to give the crude product which was purified by using an ISCO 120 g column. The desired compound was eluted with 40% EtOAc-Hexanes. The desired fractions were combined and evaporated under reduced pressure to afford 4.5 g (97%) of title compound as a colorless oil. HR-ES(+) m/e calcd for $C_{30}H_{41}O_8SI$ $(M+Na)^+$ 711.1459, found 711.1465.

Step 5: 4-{2-(2-Carboxy-ethyl)-3-[6-(3-iodo-5-methanesulfonyl-phenoxy)-hexyl]-phenoxy}-butyric Acid

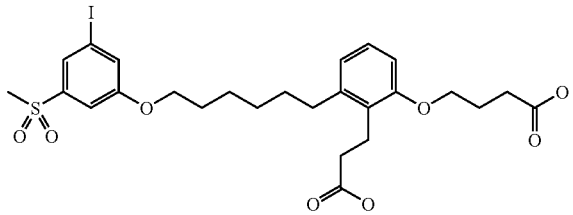

To a solution of 4-{2-(2-ethoxycarbonyl-ethyl)-3-[6-(3-iodo-5-methanesulfonyl-phenoxy)-hexyl]-phenoxy}-butyric acid ethyl ester (0.9 g, 1.31 mmol) in hot ethanol (40 mL) was added aqueous 1.0 N sodium hydroxide (10 mL). The resulting solution was heated to 60° C. and stirred for 4 h. Then, the reaction mixture was cooled down and diluted with EtOAc, washed with 10% HCl and brine. The combined ethyl acetate extracts were dried over anhydrous sodium sulfate, concentrated under reduced pressure to afford 805 mg (97%) of title compound as a light yellow oil. HR-ES(+) m/e calcd for $C_{26}H_{33}O_8SI$ $(M+H)^+$ 633.1014, found 633.1008.

Step 6: General Procedure for Suzuki Coupling

To a solution of 4-{2-(2-carboxy-ethyl)-3-[6-(3-iodo-5-methanesulfonyl-phenoxy)-hexyl]-phenoxy}-butyric acid (100 mg, 0.16 mmol), potassium carbonate (77 mg, 0.56 mmol), boronic acid (0.32 mmol) in EtOH (4 mL)/H$_2$O (1 mL) was added Pd(PPh$_3$)$_4$ (9 mg, 5 mol %). The reaction mixture was heated at 78° C. for 4 h, cooled down to room temperature then diluted with EtOAc. The resulting solution was washed with 10% HCl and brine. The organic layer was then dried over anhydrous sodium sulfate and concentrated under reduced pressure to afford the crude material. The desired products were isolated by preparative HPLC.

Example 1

4-(2-(2-Carboxy-ethyl)-3-{6-[3-(1H-indol-5-yl)-5-methanesulfonyl-phenoxy]-hexyl}-phenoxy)-butyric Acid

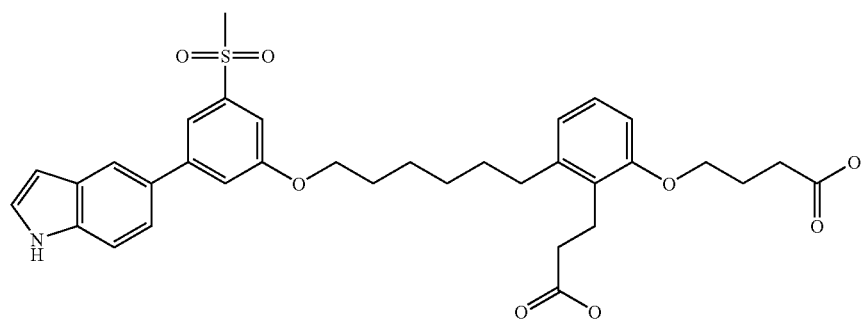

The title compound was prepared by following the general procedure for Suzuki coupling described above in step 6 with 5-indolylboronic acid. HR-ES(+) m/e calcd for $C_{34}H_{39}NO_8S$ (M+Na)$^+$ 644.2288, found 644.2288.

Example 2

4-{2-(2-Carboxy-ethyl)-3-[6-(3'-fluoro-5-methanesulfonyl-4'-methoxy-biphenyl-3-yloxy)-hexyl]-phenoxy}-butyric Acid

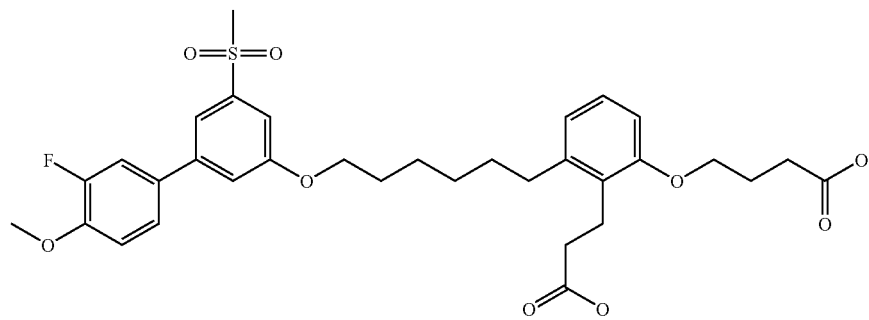

The title compound was prepared following a similar procedure as described in example 1 using 3-fluoro-4-methoxyphenylboronic acid. HR-ES(+) m/e calcd for $C_{33}H_{39}O_9SF$ (M+Na)$^+$ 653.2191, found 653.2194.

Example 3

4-{2-(2-Carboxy-ethyl)-3-[6-(3',5'-difluoro-5-methanesulfonyl-biphenyl-3-yloxy)-hexyl]-phenoxy}-butyric Acid

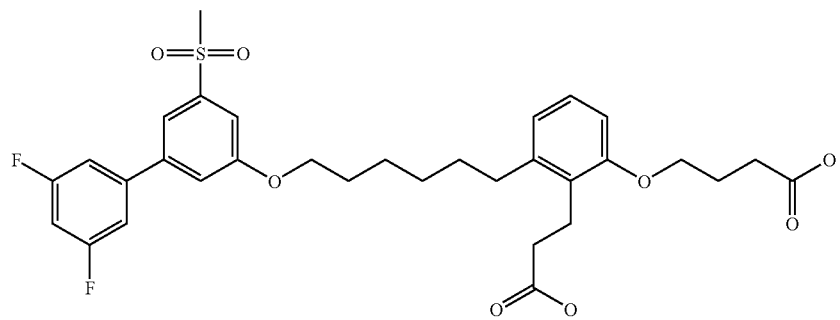

The title compound was prepared by following a similar procedure as described in example 1 using 3,5-difluorophenylboronic acid. HR-ES(+) m/e calcd for $C_{32}H_{36}O_8SF_2$ (M+Na)$^+$ 641.1991, found 641.1989.

Example 4

4-(2-(2-Carboxy-ethyl)-3-[6-(3-methanesulfonyl-5-(1-methyl-1H-indol-5-yl)-phenoxy]-hexyl}-phenoxy)-butyric Acid

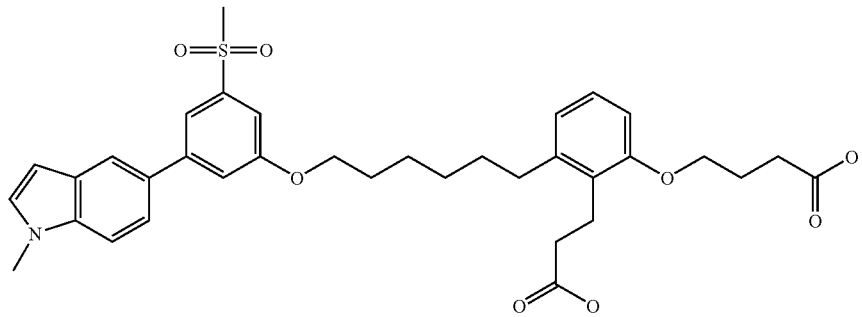

The title compound was prepared by following a similar procedure as described in example 1 using N-methylindole-5-boronic acid. HR-ES(+) m/e calcd for $C_{35}H_{41}NO_8S$ $(M+Na)^+$ 658.2445, found 658.2445.

Example 5

4-{2-(2-Carboxy-ethyl)-3-[6-(4'-hydroxy-5-methanesulfonyl-biphenyl-3-yloxy)-hexyl]-phenoxy}-butyric Acid

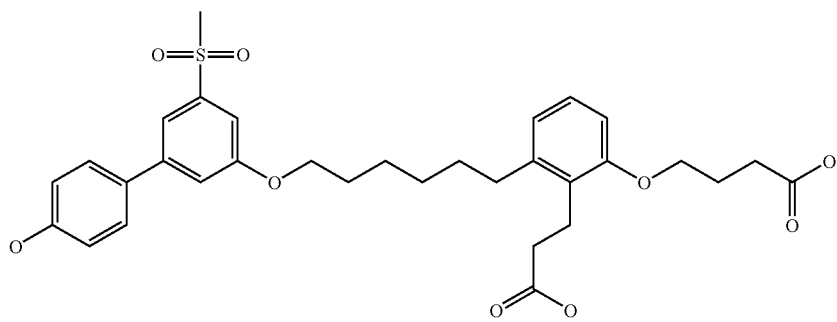

The title compound was prepared by following a similar procedure as described in example 1 using 4-hydroxyphenyl-boronic acid. HR-ES(+) m/e calcd for $C_{32}H_{38}O_9S$ $(M+H)^+$ 599.2310, found 599.2309.

Example 6

4-(2-(2-Carboxy-ethyl)-3-{6-[3-methanesulfonyl-5-(1H-pyrazol-4-yl)-phenoxy]-hexyl}-phenoxy)-butyric Acid

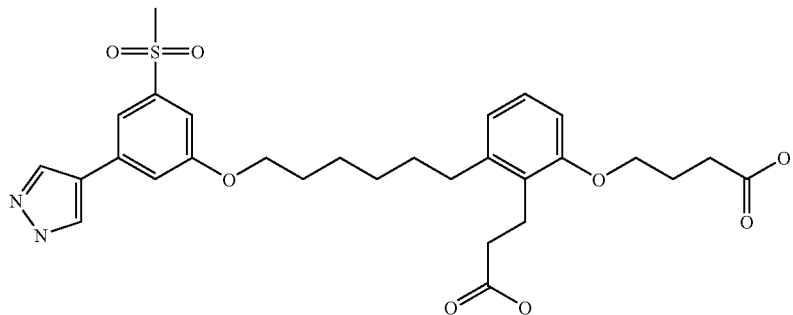

The title compound was prepared by following a similar procedure as described in example 1 using 1H-pyrazole-4-boronic acid. HR-ES(+) m/e calcd for $C_{29}H_{36}N_2O_8S$ (M+H)$^+$ 573.2265, found 573.2264.

Example 7

4-(2-(2-Carboxy-ethyl)-3-{6-[3-methanesulfonyl-5-(1-methyl-1H-pyrazol-4-yl)-phenoxy]-hexyl}-phenoxy)-butyric Acid

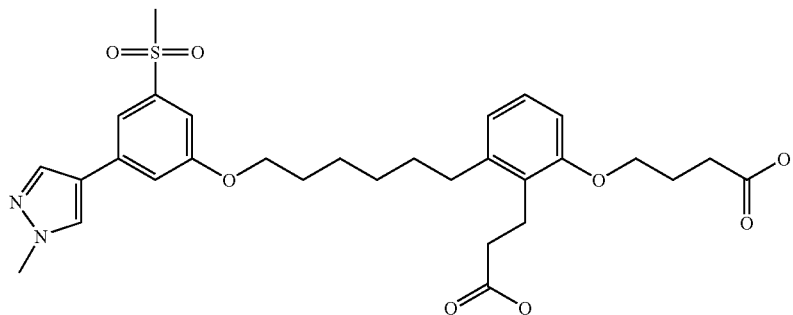

The title compound was prepared by following a similar procedure as described in example 1 using 1-methyl-4-{4,4,5,5-tetramethyl-1,3,2-dioxaborolan-2-yl}-1H-pyrazole. HR-ES(+) m/e calcd for $C_{30}H_{38}N_2O_8S$ (M+H)$^+$ 587.2422, found 587.2418.

Example 8

4-{2-(2-Carboxy-ethyl)-3-[6-(4'-fluoro-5-methane-sulfonyl-biphenyl-3-yl oxy)-hexyl]-phenoxy}-butyric Acid

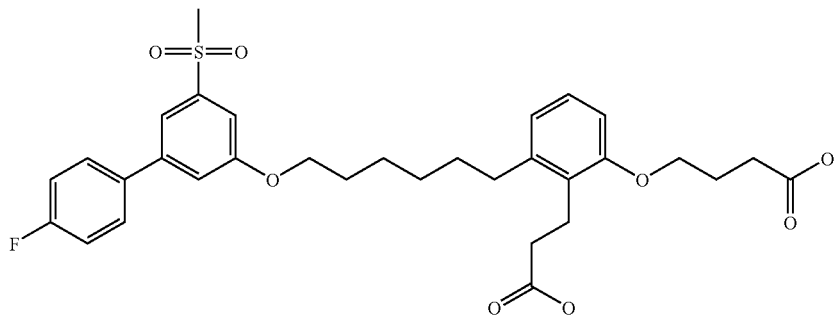

The title compound was prepared by following a similar procedure as described in example 1 using 4-fluorophenyl-boronic acid. HR-ES(+) m/e calcd for $C_{32}H_{37}O_8SF$ (M+Na)$^+$ 623.2085, found 623.2083

Example 9

4-{2-(2-Carboxy-ethyl)-3-[6-(4'-chloro-5-methane-sulfonyl-biphenyl-3-yl oxy)-hexyl]-phenoxy}-butyric Acid

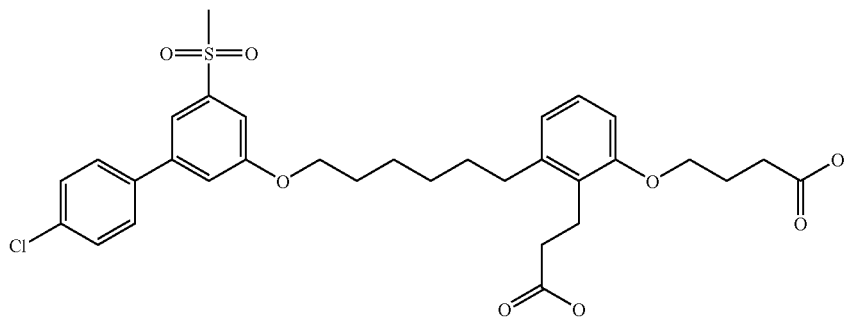

The title compound was prepared by following a similar procedure as described in example 1 using 4-chlorophenyl-boronic acid. HR-ES(+) m/e calcd for $C_{32}H_{37}O_8SCl$ (M+Na)$^+$ 639.1790, found 639.1792.

Example 10

4-{2-(2-Carboxy-ethyl)-3-[6-(3-cyclohex-1-enyl-5-methanesulfonyl-phenoxy)-hexyl]-phenoxy}-butyric Acid

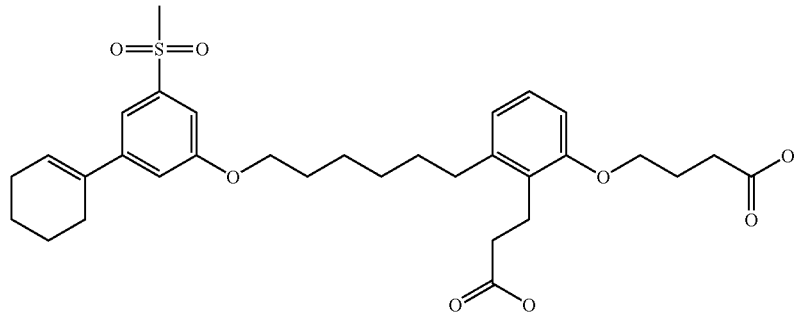

The title compound was prepared by following a similar procedure as described in example 1 using 1-cyclohexen-1-yl-boronic acid. HR-ES(+) m/e calcd for $C_{32}H_{42}O_8S$ (M+Na)$^+$ 609.2492, found 609.2497.

Method B

General Procedure for Method B

In a sealable tube, 4-{2-(2-ethoxycarbonyl-ethyl)-3-[6-(3-iodo-5-methanesulfonyl-phenoxy)-hexyl]-phenoxy}-butyric acid ethyl ester (100 mg, 0.157 mmol) in DME (3 mL) was added, followed by boronic acid (100 mg), $Cs_2CO_3$ (100 mg), and $PdCl_2(dppf)$ (20 mg). The reaction mixture was shaken at 90° C. overnight. The reaction was diluted with EtOAc (5 mL), washed with water (3 mL). The organic layer was separated and concentration under reduced pressure gave an oil, which was used in the next step without further purification. The crude sample was dissolved in EtOH (5 mL), 3N NaOH (0.5 mL) was added and stirred at 60° C. for 3 h. 3N HCl (0.55 mL) was added to neutralize the reactions. Concentration under reduced pressure gave an oil which was purified by preparative HPLC.

Example 11

4-{2-(2-Carboxy-ethyl)-3-[6-(3'-fluoro-5-methane-sulfonyl-4'-methyl-biphenyl-3-yloxy)-hexyl]-phenoxy}-butyric Acid

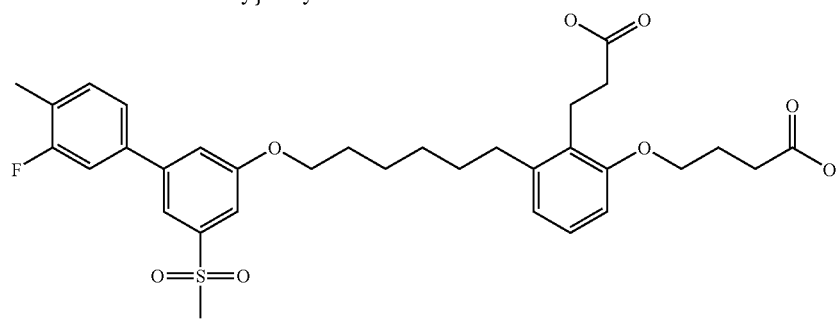

Title compound was prepared according to general procedure for method B using 3-fluoro-4-methylphenylboronic acid. LC/MS indicated a purity of 100% as measured by UV 214 nM. HR-ES(+): calculated for $C_{33}H_{40}FO_8S$ (M+Na)$^{1+}$ 628.2423, found 628.2418.

Example 12

4-{2-(2-Carboxy-ethyl)-3-[6-(3-methanesulfonyl-5-thiophen-3-yl-phenoxy)-hexyl]-phenoxy}-butyric Acid

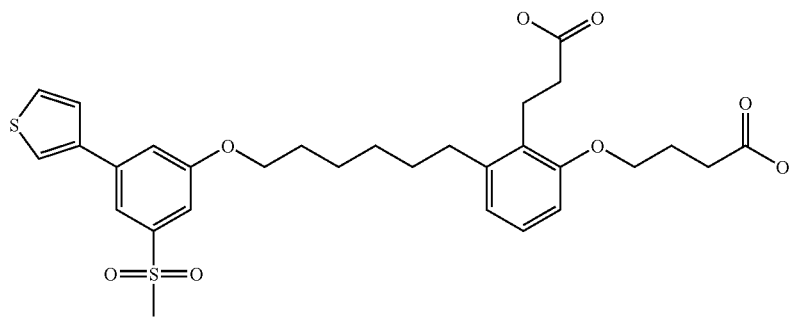

Title compound was prepared according to general procedure for method B using thiophene-3-boronic acid. LC/MS indicated a purity of 100% as measured by UV 214 nM. HR-ES(+): calculated for $C_{30}H_{36}O_8S_2$ $(M+Na)^{1+}$ 611.1744, found 611.1740.

Example 13

4-{2-(2-Carboxy-ethyl)-3-[6-(4'-ethyl-5-methanesulfonyl-biphenyl-3-yloxy)-hexyl]-phenoxy}-butyric Acid

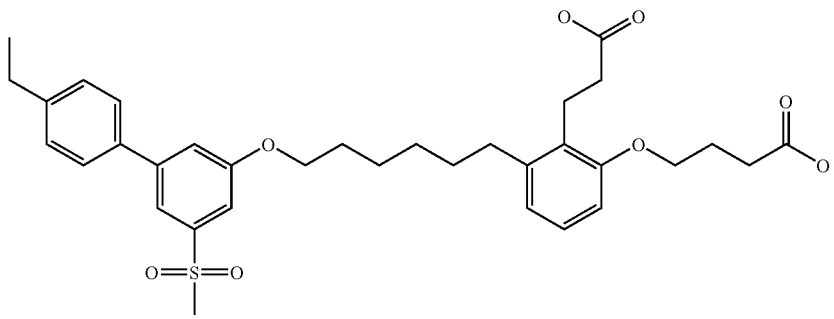

Title compound was prepared according to general procedure for method B using 4-ethylphenylboronic acid. LC/MS indicated a purity of 100% as measured by UV 214 nM. HR-ES(+): calculated for $C_{34}H_{42}O_8S$ $(M+Na)^{1+}$ 633.2492, found 633.2492.

Example 14

4-{2-(2-Carboxy-ethyl)-3-[6-(4'-chloro-3'-fluoro-5-methanesulfonyl-biphenyl-3-yloxy)-hexyl]-phenoxy}-butyric Acid

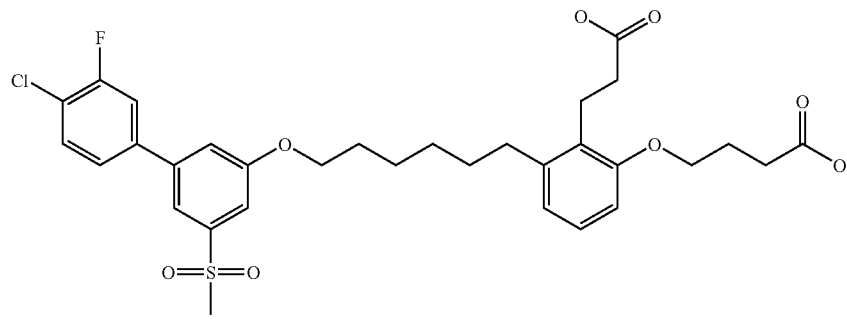

Title compound was prepared according to general procedure for method B using 4-chloro-3-fluorophenylboronic acid. LC/MS indicated a purity of 93% as measured by UV 214 nM. HR-ES(+): calculated for $C_{32}H_{36}ClFO_8S$ (M+Na)$^{1+}$ 657.1695, found 657.1696.

Example 15

4-{2-(2-Carboxy-ethyl)-3-[6-(5-methanesulfonyl-3'-methoxy-biphenyl-3-yloxy)-hexyl]-phenoxy}-butyric acid

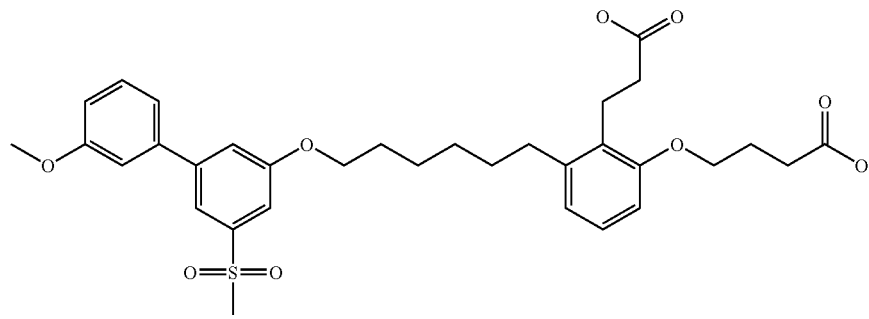

Title compound was prepared according to general procedure for method B using 3-methoxyphenylboronic acid. LC/MS indicated a purity of 100% as measured by UV 214 nM. HR-ES(+): calculated for $C_{33}H_{40}O_9S$ (M+Na)$^{1+}$ 635.2285, found 635.2284.

Example 16

4-(2-(2-Carboxy-ethyl)-3-{6-[3-(2,3-dihydro-benzo-furan-5-yl)-5-methanesulfonyl-phenoxy]-hexyl}-phenoxy)-butyric Acid

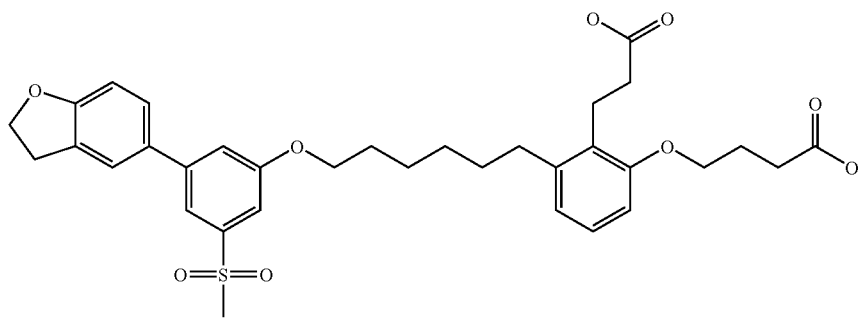

Title compound was prepared according to general procedure for method B using 2,3-dihydrobenzofuran-5-boronic acid. LC/MS indicated a purity of 91% as measured by UV 214 nM. HR-ES(+): calculated for $C_{34}H_{40}O_9S$ $(M+Na)^{1+}$ 647.2285, found 647.2282.

Example 17

4-{2-(2-Carboxy-ethyl)-3-[6-(3'-chloro-5-methane-sulfonyl-biphenyl-3-yloxy)-hexyl]-phenoxy-butyric Acid

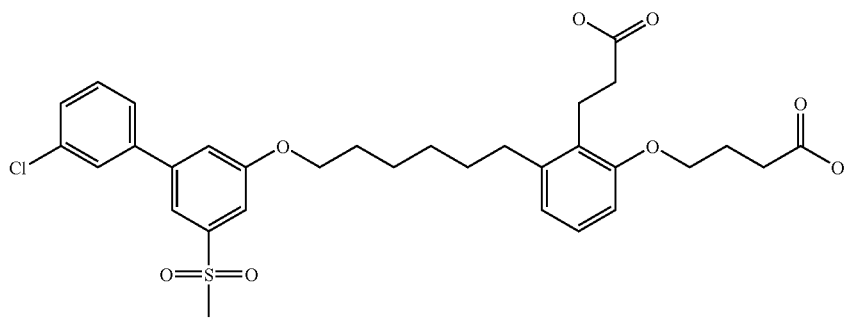

Title compound was prepared according to general procedure for method B using 3-chlorophenylboronic acid. LC/MS indicated a purity of 93% as measured by UV 214 nM. HR-ES (+): calculated for $C_{32}H_{37}ClO_8S$ $(M+Na)^{1+}$ 639.1790, found 639.1790

Example 18

4-{2-(2-Carboxy-ethyl)-3-[6-(4'-ethoxy-5-methane-sulfonyl-biphenyl-3-yloxy)-hexyl]-phenoxy-butyric Acid

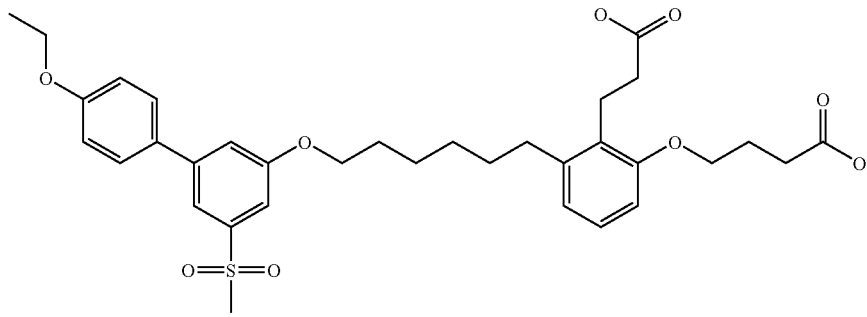

Title compound was prepared according to general procedure for method B using 4-ethoxyphenylboronic acid. LC/MS indicated a purity of 100% as measured by UV 214 nM. HR-ES(+): calculated for $C_{34}H_{42}O_9S$ $(M+Na)^{1+}$ 649.2442, found 649.2436.

Example 19

4-(2-(2-Carboxy-ethyl)-3-{6-[3-methanesulfonyl-5-(4-methyl-thiophen-3-yl)-phenoxy]-hexyl-phenoxy)-butyric Acid

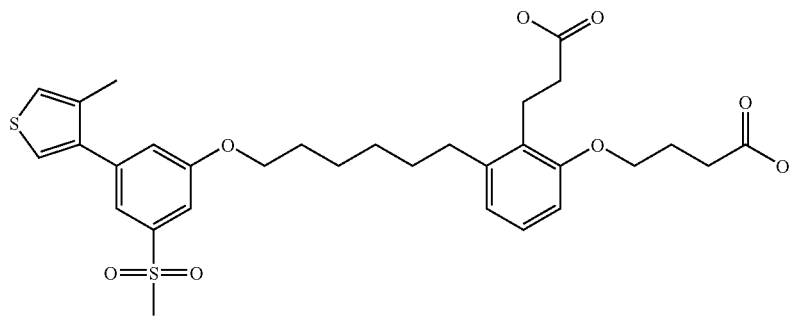

Title compound was prepared according to general procedure for method B using 4-methyl-3-thiopheneboronic acid. LC/MS indicated a purity of 100% as measured by UV 214 nM. HR-ES(+): calculated for $C_{31}H_{38}O_8S_2$ $(M+Na)^{1+}$ 625.1900, found 625.1901.

Method C

Example 20

4-{2-(2-Carboxy-ethyl)-3-[6-(3-methanesulfonyl-5-thiazol-2-yl-phenoxy)-hexyl]-phenoxy}-butyric Acid

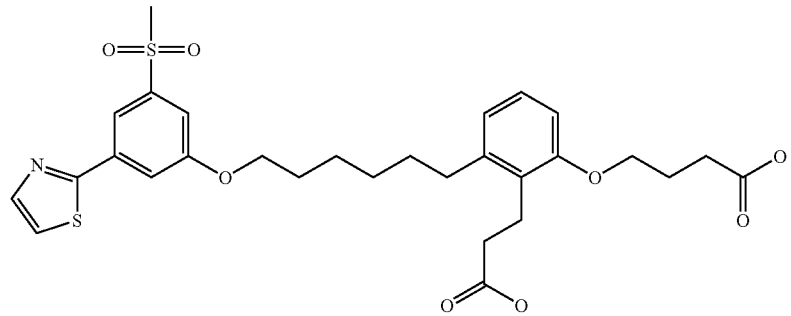

To a solution containing 4-{2-(2-ethoxycarbonyl-ethyl)-3-[6-(3-iodo-5-methanesulfonyl-phenoxy)-hexyl]-phenoxy}-butyric acid ethyl ester (90 mg, 0.14 mmol) and 2-(tributylstannyl)thiazole (0.088 mL, 0.28 mmol) in toluene (4 mL) was added Pd(PPh$_3$)$_4$ (8 mg, 5 mol %). The reaction mixture was stirred at 110° C. for 12 h, then diluted with EtOAc. The resulting solution was washed with brine. The organic layer was dried over anhydrous sodium sulfate and concentrated under reduced pressure to afford a crude sample which was dissolved in hot ethanol (4 mL). To this solution, 1 N sodium hydroxide (1 mL) was added and the reaction mixture was stirred at 60° C. for 3 h. Once the hydrolysis was completed as determined by LCMS, the reaction mixture was diluted with EtOAc and washed with 10% HCl and brine. The organic layer was dried over anhydrous sodium sulfate and concentrated under reduced pressure to afford a crude sample which was purified by preparative HPLC. HR-ES(+) m/e calcd for C$_{29}$H$_{35}$NO$_8$S$_2$ (M+H)$^+$ 590.1877, found 590.1876.

Example 21

4-{2-(2-Carboxy-ethyl)-3-[6-(3-methanesulfonyl-5-thiazol-4-yl-phenoxy)-hexyl]-phenoxy}-butyric Acid

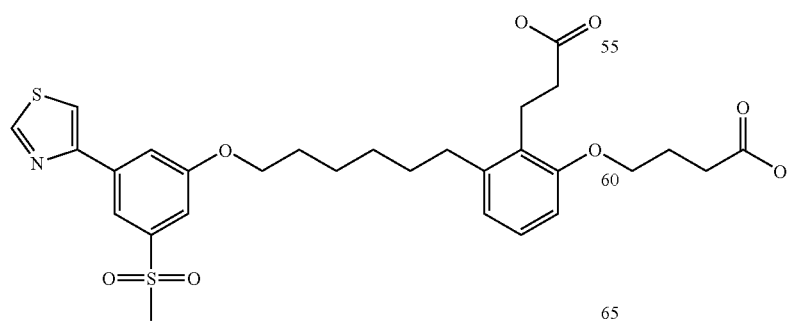

Step 1: 4-{2-(2-Ethoxycarbonyl-ethyl)-3-[6-(3-methanesulfonyl-5-thiazol-4-yl-phenoxy)-hexyl]-phenoxy}-butyric Acid Ethyl Ester

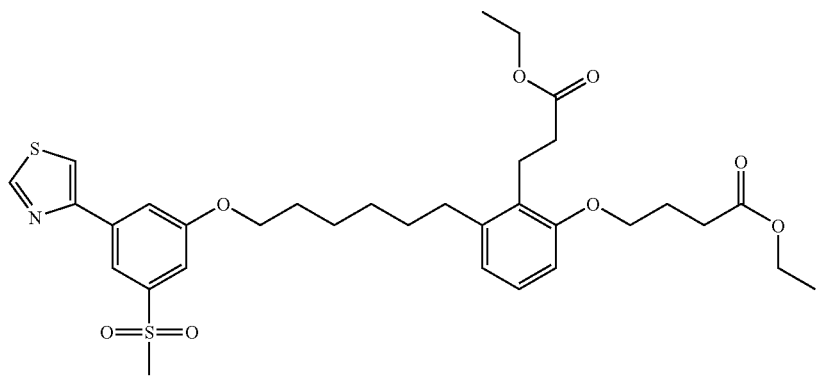

To a solution of 4-{2-(2-ethoxycarbonyl-ethyl)-3-[6-(3-iodo-5-methanesulfonyl-phenoxy)-hexyl]-phenoxy}-butyric acid ethyl ester (300 mg, 0.436 mmol) in toluene (20 mL), 4-(tributylstannyl)thiazole (243 mg, 0.25 mL, 0.653 mmol) was added, followed by Pd(PPh$_3$)$_4$ (25 mg, 0.0217 mmol). The reaction mixture was heated at 90° C. overnight. The reaction was diluted with EtOAc (250 mL), washed with water (100 mL). The organic layer was washed with brine, dried over Na$_2$SO$_4$, concentration under reduced pressure gave an oil which was purified by column chromatography. The title compound was eluted with 50% EtOAc/Hexanes to provide title compound (280 mg, 99%) as an oil.

$^1$H NMR (CDCl$_3$): □ 8.91 (d, 1H), 8.02 (d, 1H), 7.79 (d, 1H), 7.68 (d, 1H), 7.41 (d, 1H), 7.09 (dd, 1H), 6.77 (d, 1H), 6.68 (d, 1H), 4.17-4.06 (m, 6H), 3.99 (dd, 2H), 3.10 (s, 3H), 2.97 (dd, 2H), 2.61 (m, 2H), 2.56-2.46 (m, 4H), 2.17-0.89 (m, 16H).

Step 2: 4-{2-(2-Carboxy-ethyl)-3-[6-(3-methanesulfonyl-5-thiazol-4-yl-phenoxy)-hexyl]-phenoxy}-butyric Acid

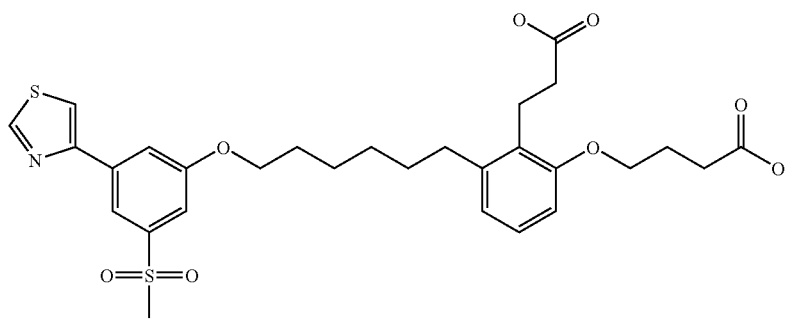

To a solution of 4-{2-(2-ethoxycarbonyl-ethyl)-3-[6-(3-methanesulfonyl-5-thiazol-4-yl-phenoxy)-hexyl]-phenoxy}-butyric acid ethyl ester (280 mg, 0.434 mmol) in EtOH (20 mL), 3N NaOH (1 mL) was added and heated at 70° C. for 2 h. The reaction was acidified with 3N HCl (1.1 mL). Concentration under reduced pressure gave an oil. Preparative HPLC provided title compound (119 mg, 46% yield). LC/MS indicated a purity of 92% as measured by UV 214 nM. HR-ES (+): calculated for C$_{29}$H$_{36}$NO$_8$S$_2$ (M+H)$^{1+}$ 590.1877, found 590.1876.

Example 22

4-{2-(2-Carboxy-ethyl)-3-[6-(3-methanesulfonyl-5-pyrimidin-4-yl-phenoxy)-hexyl]-phenoxy}-butyric Acid

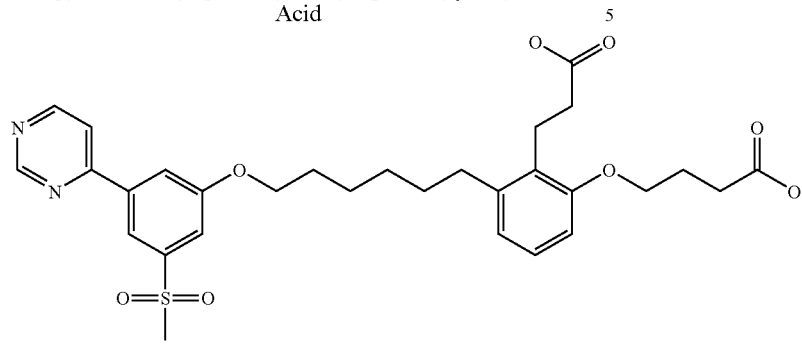

Step 1: 4-(2-(2-Ethoxycarbonyl-ethyl)-3-{6-[3-methanesulfonyl-5-(2-methylsulfanyl-pyrimidin-4-yl)-phenoxy]-hexyl}-phenoxy)-butyric Acid Ethyl Ester

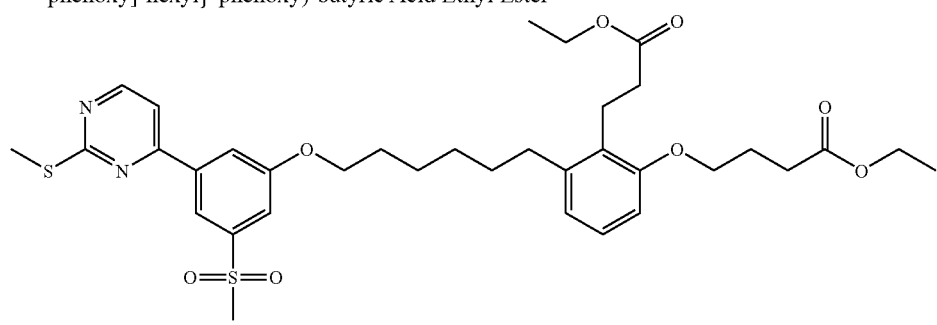

Title compound was prepared according to a similar procedure described in Example 21, step 1 by reaction of 4-{2-(2-ethoxycarbonylethyl)-3-[6-(3-iodo-5-methanesulfonyl-phenoxy)-hexyl]-phenoxy}-butyric acid ethyl ester (300 mg, 0.436 mmol) with 2-methylsulfanyl-4-trimethylstannanyl-pyrimidine (189 mg, 0.653 mmol) to afford 4-(2-(2-ethoxycarbonyl-ethyl)-3-{6-[3-methanesulfonyl-5-(2-methylsulfanyl-pyrimidin-4-yl)-phenoxy]-hexyl}-phenoxy)-butyric acid ethyl ester (292 mg, 97% yield) as an oil. $^1$H NMR (CDCl$_3$): □ 8.62 (d, 1H), 8.16 (s, 1H), 7.92 (s, 1H), 7.55 (s, 1H), 7.42 (d, 1H), 7.09 (dd, 1H), 6.77 (d, 1H), 6.68 (d, 1H), 4.17-4.07 (m, 6H), 3.99 (dd, 2H), 3.10 (s, 3H), 2.97 (dd, 2H), 2.66-2.61 (m, 5H), 2.56-2.46 (m, 4H), 2.17-0.89 (m, 16H).

Step 2: 4-{2-(2-Ethoxycarbonyl-ethyl)-3-[6-(3-methanesulfonyl-5-pyrimidin-4-yl-phenoxy)-hexyl]-phenoxy}-butyric Acid Ethyl Ester

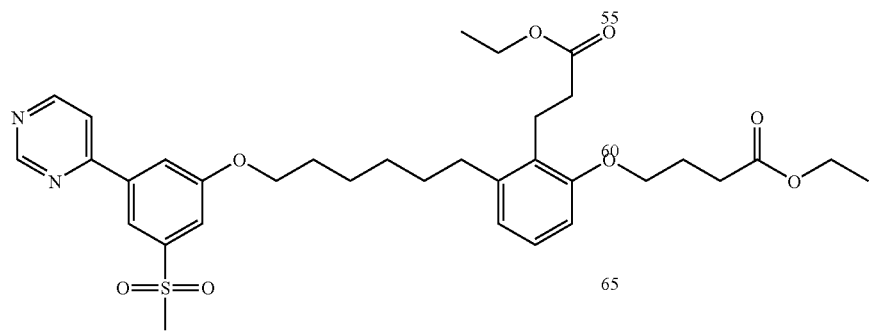

To a solution of 4-(2-(2-ethoxycarbonyl-ethyl)-3-{6-[3-methanesulfonyl-5-(2-methylsulfanyl-pyrimidin-4-yl)-phenoxy]-hexyl}-phenoxy)-butyric acid ethyl ester (292 mg, 0.423 mmol) in MeOH (15 ml) and THF (15 mL), Raney Ni (2 mL) was added, and stirred at r.t. for 3 h. The reaction was filtered, the residue was washed with MeOH, concentration gave an oil which was used in the next step without further purification. (164 mg).

Step 3: 4-{2-(2-Carboxy-ethyl)-3-[6-(3-methanesulfonyl-5-pyrimidin-4-yl-phenoxy)-hexyl]-phenoxy}-butyric Acid

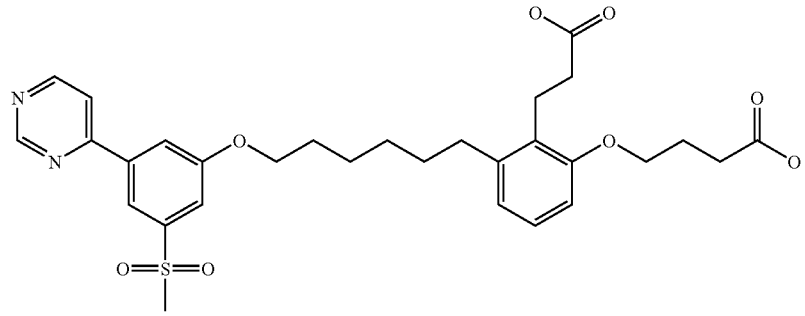

Title compound was prepared according to a similar procedure described in Example 21, step 2 by reaction of 4-{2-(2-ethoxycarbonyl-ethyl)-3-[6-(3-methanesulfonyl-5-pyrimidin-4-yl-phenoxy)-hexyl]-phenoxy}-butyric acid ethyl ester (164 mg) with 3 N NaOH (1 mL). Preparative HPLC provided the title compound. LC/MS indicated a purity of 84% as measured by UV 214 nM. HR-ES(+): calculated for $C_{30}H_{37}N_2O_8S$ $(M+H)^{1+}$ 582.2265, found 585.2267.

Method D

General Procedure for Method D

In a microwave tube, 4-{2-(2-ethoxycarbonyl-ethyl)-3-[6-(3-iodo-5-methanesulfonyl-phenoxy)-hexyl]-phenoxy}-butyric acid ethyl ester (100 mg, 0.15 mmol), phenol (0.30 mmol), CuI (28 mg, 0.15 mmol), N,N-dimethylglycine hydrochloride salt (21 mg, 0.15 mmol), $Cs_2CO_3$ (170 mg, 0.53 mmol) and dioxane (4 mL) were added. The tube was sealed, purged with argon and submitted to microwave irradiation for 30 minutes at 200° C. using the Emrys Optimizer. The suspension was filtered and the filtrate was concentrated under reduced pressure. The crude sample was diluted with EtOAc and washed with a saturated $NaHCO_3$ aqueous solution. The organic layer was dried over anhydrous sodium sulfate and concentrated under reduced pressure to afford a crude sample which was dissolved in hot ethanol (4 mL). To this solution, 1 N sodium hydroxide (1 mL) was added and the reaction mixture was stirred at 60° C. for 4 h. Once the hydrolysis was completed as determined by LCMS, the reaction mixture was diluted with EtOAc and washed with 10% HCl and brine. The organic layer was dried over anhydrous sodium sulfate and concentrated under reduced pressure to afford a crude sample which was purified by preparative HPLC.

Example 23

4-(2-(2-Carboxy-ethyl)-3-{6-[3-(4-chloro-phenoxy)-5-methanesulfonyl-phenoxy]-hexyl}-phenoxy)-butyric Acid

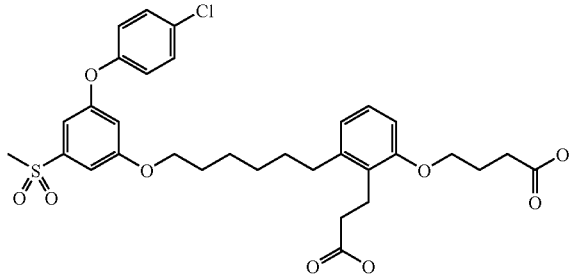

The title compound was prepared by following the general method D described above with 4-chlorophenol. HR-ES(+) m/e calcd for $C_{32}H_{37}O_9SCl$ $(M+Na)^+$ 655.1739, found 655.1744.

Example 24

4-(2-(2-Carboxy-ethyl)-3-{6-[3-(4-fluoro-phenoxy)-5-methanesulfonyl-phenoxy]-hexyl}-phenoxy)-butyric acid

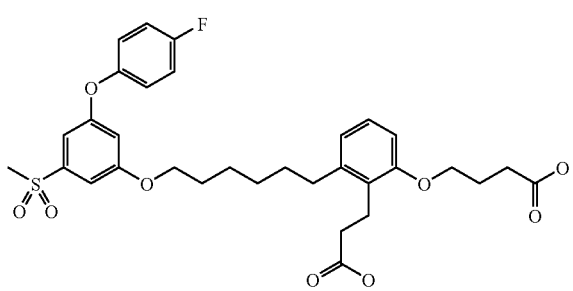

The title compound was prepared by following the general method D described above with 4-fluorophenol. HR-ES(+) m/e calcd for $C_{32}H_{37}O_9SF$ $(M+Na)^+$ 639.2034, found 639.2036.

Method E

General Procedure for Method E

A mixture of 4-{2-(2-ethoxycarbonyl-ethyl)-3-[6-(3-iodo-5-methanesulfonyl-phenoxy)-hexyl]-phenoxy}-butyric acid ethyl ester (100 mg, 0.15 mmol), amine (0.30 mmol), CuI (11 mg, 0.06 mmol), L-proline (7 mg, 0.06 mmol), $K_2CO_3$ (116 mg, 0.84 mmol) in DMSO (4 mL) was heated at 80° C. for 12 h. After completion, the reaction mixture was diluted with EtOAc and washed with brine and water. The organic layer was dried over anhydrous sodium sulfate and concentrated under reduced pressure to afford a crude sample which was dissolved in hot ethanol (4 mL). To this solution, 1 N sodium hydroxide (1 mL) was added and the reaction mixture was stirred at 60° C. for 4 h. Once the hydrolysis was completed as determined by LCMS, the reaction mixture was diluted with EtOAc and washed with 10% HCl and brine. The organic layer was dried over anhydrous sodium sulfate and concentrated under reduced pressure to afford a crude sample which was purified by preparative HPLC.

Example 25

4-{2-(2-Carboxy-ethyl)-3-[6-(3-cyclopropylamino-5-methanesulfonyl-phenoxy)-hexyl]-phenoxy}-butyric Acid

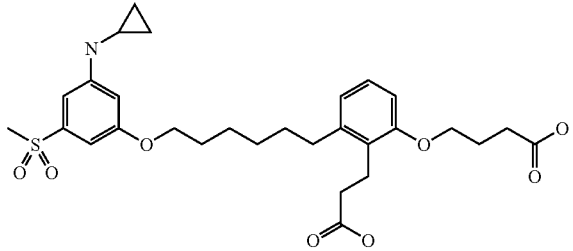

The title compound was prepared by following the general method E described above with cyclopropylamine. HR-ES (+) m/e calcd for $C_{29}H_{39}NO_8S$ $(M+H)^+$ 562.2469, found 562.2467.

Example 26

4-{2-(2-Carboxy-ethyl)-3-[6-(3-methanesulfonyl-5-phenylamino-phenoxy)-hexyl]-phenoxy}-butyric Acid

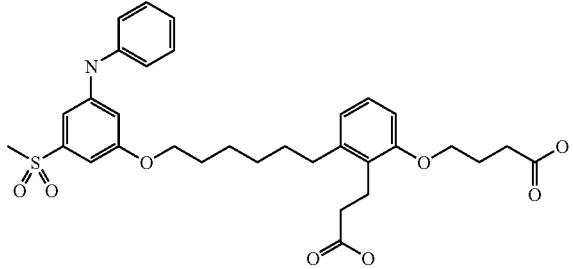

The title compound was prepared by following the general method E described above with aniline. HR-ES(+) m/e calcd for $C_{32}H_{39}NO_8S$ $(M+H)^+$ 598.2469, found 598.2466.

Method F

Step 1: 1-Benzyloxy-3,5-dibromo-benzene

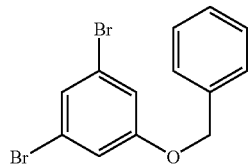

To a solution of benzyl alcohol (10.8 g, 100 mmol) in dry DMF (40 mL), 60% NaH (4.4 g, 110 mmol) was added portionwise and the mixture was stirred at 55° C. for 10 min. Then, 1,3,5-tribromobenzene (22.0 g, 70 mmol) was added slowly to the reaction mixture and the resulting solution was heated at 120° C. for 4 h. After cooling to room temperature, the reaction mixture was poured into a mixture of diethyl ether (500 mL) and water (200 mL) along with intense stirring. The organic layer was separated and washed with water (2×100 mL), 5% HCl (100 mL), saturated $NaHCO_3$ aqueous solution (100 mL) and brine (100 mL). The organic phase was dried over magnesium sulfate, filtered and concentrated under reduced pressure. The residue was purified by column chromatography on silica using hexanes-acetone (10:0.5) as eluent to afford 18.5 g (77%) of title compound as an yellow oil. $^1$H NMR (CDCl$_3$, 300 MHz): δ 7.45-7.32 (m, 5H); 7.25 (s, 1H); 7.07 (s, 2H); 5.05 (s, 2H).

Step 2: 1-Benzyloxy-3-bromo-5-methylsulfanyl-benzene

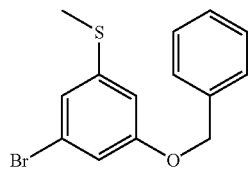

To a solution of 1-benzyloxy-3,5-dibromo-benzene (9.6 g, 28.1 mmol) in dry DMF (55 mL) was added sodium thiomethoxide (1.97 g, 28.1 mmol). The reaction mixture was then stirred at 100° C. for 1 h. After cooling to room temperature, the reaction mixture was poured into a mixture of diethyl ether (50 mL) and water (20 mL) along with intense stirring. The organic layer was separated and washed with water and brine. The organic phase was dried over magnesium sulfate, filtered and concentrated under reduced pressure. The residue was purified by column chromatography on silica using hexanes-acetone (5:0.2) as eluent to afford 3.68 g (42%) of title compound as an yellow oil. $^1$H NMR (CDCl$_3$, 300 MHz): δ 7.41-7.26 (m, 5H); 6.96 (s, 1H); 6.90 (s, 1H); 6.80 (s, 1H); 5.05 (s, 2H); 2.46 (s, 3H).

Step 3: 1-Benzyloxy-3-bromo-5-methanesulfonyl-benzene

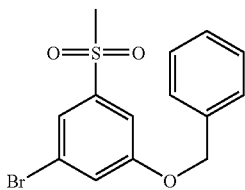

To a solution of 1-benzyloxy-3-bromo-5-methylsulfanyl-benzene (3.68 g, 12 mmol) in glacial acetic acid (20 mL) 30% $H_2O_2$ solution was added slowly. Then the reaction mixture was heated at 95° C. for 5 h. After cooling to room temperature, reaction mixture was diluted with dichloromethane (150 mL) and washed with water, saturated aq. $Na_2CO_3$ and 5% aq. sodium pyrosulfite ($Na_2S_2O_5$) solution. The organic extract was dried over magnesium sulfate, filtered and concentrated under reduced pressure. The residue was purified by column chromatography on silica using hexanes-acetone (10:1) as eluent to afford 3.46 g (85%) of the title compound as a white solid. $^1$H NMR (CDCl$_3$, 300 MHz): δ 7.66 (s, 1H); 7.45 (s, 1H); 7.43-7.34 (m, 6H); 5.09 (s, 2H); 3.01 (s, 3H).

Step 4: General Procedure for the Suzuki Coupling

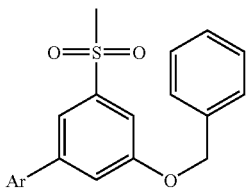

Method A

A mixture of 1-benzyloxy-3-bromo-5-methanesulfonyl-benzene (300 mg, 0.88 mmol), the appropriate boronic acid component (1.23 mmol), aq. $Na_2CO_3$ solution (0.55 g in 2.2 mL water), catalytic amount of KI (10 mg), Pd(PPh$_3$)$_4$ (65 mg, 5 mol %) and dry DCE (2.2 mL) was charged into a 8 mL microwave glass-vessel. The vessel was sealed and the reaction mixture was irradiated in the cavity with 80 W power at 160° C. for 30-60 min using a CEM Explorer Labmate Microwave instrument. After cooling to room temperature, the vessel was carefully opened and the reaction was checked by TLC. The reaction mixture was concentrated under reduced pressure and EtOAc was added. The resulting solution was washed with water. The organic extract was dried over magnesium sulfate, filtered and concentrated under reduced pressure. The residue was purified on a silica column by biotage purification station using hexanes-EtOAc (4:1) as eluent.

Method B

A mixture of 1-benzyloxy-3-bromo-5-methanesulfonyl-benzene (300 mg, 0.88 mmol), the appropriate boronic acid component (1.23 mmol), cesium fluoride (2.2 mmol), Pd(PPh$_3$)$_4$ (65 mg, 5 mol %) and dry acetonitrile (3 mL) was charged into a 8 mL microwave glass-vessel. The vessel was sealed and the reaction mixture was irradiated in the cavity with 80 W power at 160° C. for 30-60 min using a CEM Explorer Labmate Microwave instrument. After cooling to room temperature, the vessel was carefully opened and the reaction was checked by TLC. The reaction mixture was concentrated under reduced pressure and dichloromethane was added. The resulting solution was washed with water. The organic phase was dried over magnesium sulfate, filtered and concentrated under reduced pressure. The residue was purified on a silica column by Biotage purification system using hexanes-EtOAc (3:2) as eluent.

Step 5: General Procedure for the Removal of Benzyl Group

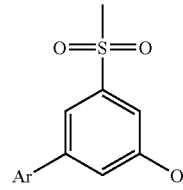

Method A

In a round-bottom flask equipped with a magnetic stir bar, the total amount of product made in step 4 was dissolved in dichloromethane (10 mL). The flask was flushed with dry nitrogen gas. The solution was cooled to −65° C. then boron tribromide (4 molar equiv. dissolved in 0.5 mL of dichloromethane) was added carefully. The mixture was stirred at room temperature overnight. Then crushed ice and dichloromethane was added to the reaction mixture. The organic layer was dried over magnesium sulfate, filtered and concentrated under reduced pressure. The crude residue obtained was then triturated with hexanes and filtered to afford the desired phenol. (in some cases, the phenol precipitated after the addition of ice and dichloromethane, so the phenol was just filtered and washed with hexanes).

Method B

The total amount of product made in step 4 was dissolved in a 1:1 mixture of MeOH-DCM (5 mL) then 10% Pd/C catalyst (40 weight % to the starting material) was added. The reaction mixture was hydrogenated by bubbling $H_2$ gas directly in the solution at room temperature under atmospheric pressure. The reaction time typically varied between 1.5-3 h. The reaction mixture was then filtered through a Hyflo Super Cel pad and washed with MeOH-DCM. The filtrate was concentrated under reduced pressure and the residue was triturated with hexanes and filtered to afford the desired phenol.

3'-Fluoro-5-methanesulfonyl-biphenyl-3-ol

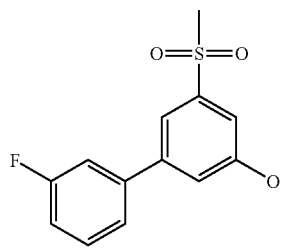

The title compound was prepared according to the general procedure in step 4, method A and step 5, method A using 3-fluorophenylboronic acid.

LC/MS calcd for $C_{13}H_{11}FO_3S$ [M+H]$^+$ 267.04, observed 267.04.

5-Methanesulfonyl-biphenyl-3-ol

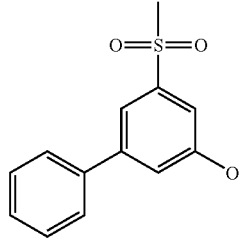

The title compound was prepared according to the general procedure in step 4, method A and step 5, method A using phenylboronic acid.

LC/MS calcd for $C_{13}H_{12}O_3S$ [M+H]$^+$ 249.05, observed 249.08.

5-Methanesulfonyl-4'-methoxy-biphenyl-3-ol

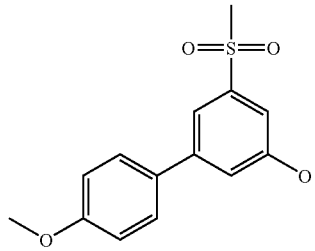

The title compound was prepared according to the general procedure in step 4, method A and step 5, method B using 4-methoxyphenylboronic acid.

LC/MS calcd for $C_{14}H_{14}O_4S$ [M+H]$^+$ 279.06, observed 279.16.

4'-Fluoro-5-methanesulfonyl-3'-methyl-biphenyl-3-ol

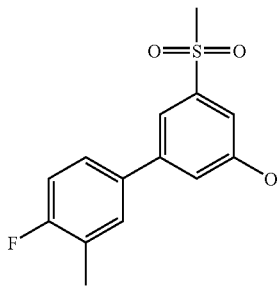

The title compound was prepared according to the general procedure in step 4, method A and step 5, method A using 4-fluoro-3-methylphenylboronic acid.

3'-Chloro-4'-fluoro-5-methanesulfonyl-biphenyl-3-ol

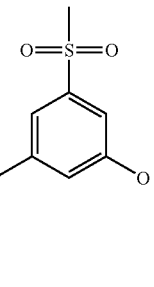

The title compound was prepared according to the general procedure in step 4, method A and step 5, method A using 3-chloro-4-fluorophenylboronic acid.

2'-Fluoro-5-methanesulfonyl-biphenyl-3-ol

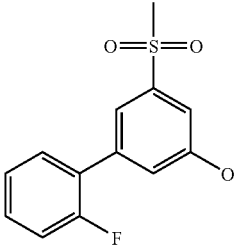

The title compound was prepared according to the general procedure in step 4, method A and step 5, method A using 2-fluorophenylboronic acid.

LC/MS calcd for $C_{13}H_{11}FO_3S$ [M+H]$^+$ 267.04, observed 267.15

5-Methanesulfonyl-2'-trifluoromethyl-biphenyl-3-ol

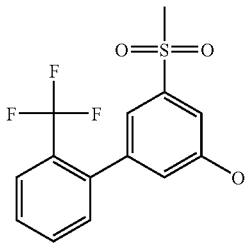

The title compound was prepared according to the general procedure in step 4, method A and step 5, method A using 2-trifluoromethylphenylboronic acid.

LC/MS calcd for $C_{14}H_{11}F_3O_3S$ [M+H]$^+$ 317.04, observed 317.15.

5-Methanesulfonyl-3'-methyl-biphenyl-3-ol

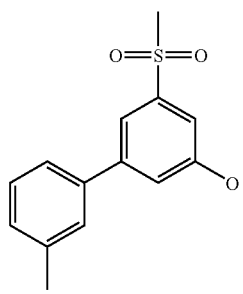

The title compound was prepared according to the general procedure in step 4, method A and step 5, method A using 3-methylphenylboronic acid.

LC/MS calcd for $C_{14}H_{14}O_3S$ [M+H]$^+$ 263.07, observed 263.17.

2'-Chloro-5-methanesulfonyl-biphenyl-3-ol

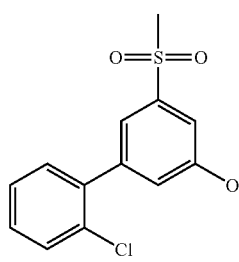

The title compound was prepared according to the general procedure in step 4, method A and step 5, method A using 2-chlorophenylboronic acid.

LC/MS calcd for $C_{14}H_{14}O_3S$ [M+H]$^+$ 283.01, observed 283.07.

5-Methanesulfonyl-4'-trifluoromethoxy-biphenyl-3-ol

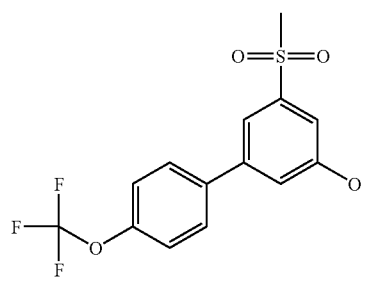

The title compound was prepared according to the general procedure in step 4, method A and step 5, method B using 4-trifluoromethoxyphenylboronic acid.

LC/MS calcd for $C_{14}H_{11}F_3O_4S$ [M−H]$^−$ 331.03, observed 330.97.

3-Methanesulfonyl-5-pyridin-4-yl-phenol

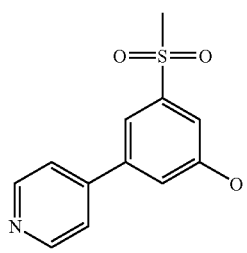

The title compound was prepared according to the general procedure in step 4, method B and step 5, method A using pyridine-4-boronic acid.

LC/MS calcd for $C_{12}H_{11}NO_3S$ [M+H]$^+$ 250.05, observed 250.02.

3-Methanesulfonyl-5-pyridin-3-yl-phenol

The title compound was prepared according to the general procedure in step 4, method B and step 5, method A using pyridine-3-boronic acid.

LC/MS calcd for $C_{12}H_{11}NO_3S$ [M+H]$^+$ 250.05, observed 249.86.

3-Methanesulfonyl-5-thiophen-2-yl-phenol

The title compound was prepared according to the general procedure in step 4, method B and step 5, method A using thiophene-2-boronic acid.

LC/MS calcd for $C_{11}H_{10}O_3S_2$ [M+H]$^+$ 255.01, observed 255.01.

Step 6: General Procedure for Method F

To a solution of a phenol (from 0.05 mmol to 0.4 mmol) in a mixture of acetone and DMF (2:1, 2 mL) were added potassium carbonate or cesium carbonate (5-10 eq.) and 4-[3-(6-bromo-hexyl)-2-(2-ethoxycarbonyl-ethyl)-phenoxy]-butyric acid ethyl ester (1.1 eq). The resulting mixture was stirred at 75° C. for 2 days. Then, the insoluble material was filtered out and the filtrate was diluted with ethyl acetate and washed with water and brine. The organic extract was dried over anhydrous sodium sulfate, concentrated and used for the next step without further purification. The total amount of material from the previous step was dissolved in EtOH (2 mL), followed by addition of 10 M NaOH solution (10 eq.). The resulting reaction mixture was stirred at room temperature overnight. Then it was neutralized with 3 N HCl and extracted into ethyl acetate. The organic extract was washed with water and brine and dried over anhydrous sodium sulfate. The crude material was purified by reverse-phase HPLC.

Example 27

4-{2-(2-Carboxy-ethyl)-3-[6-(3'-fluoro-5-methane-sulfonyl-biphenyl-3-yloxy)-hexyl]-phenoxy}-butyric Acid

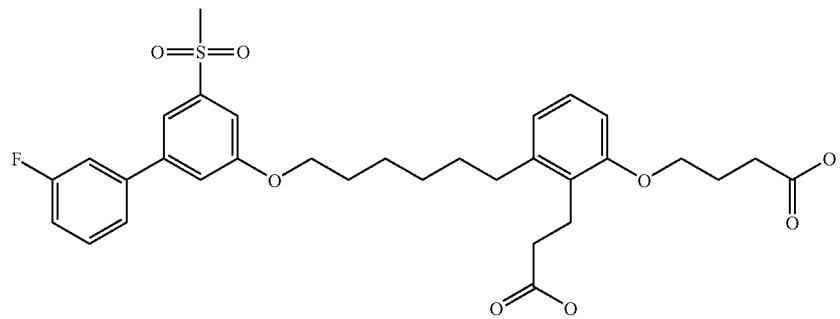

The title compound was prepared according to the general procedure for method F starting from 3'-fluoro-5-methane-sulfonyl-biphenyl-3-ol. Yield: 7% (after two steps)

HRMS calcd for $C_{32}H_{37}O_8FS$ [M+H]$^+$ 623.2085, observed 623.2088

Example 28

4-{2-(2-Carboxy-ethyl)-3-[6-(5-methanesulfonyl-biphenyl-3-yloxy)-hexyl]-phenoxy}-butyric Acid

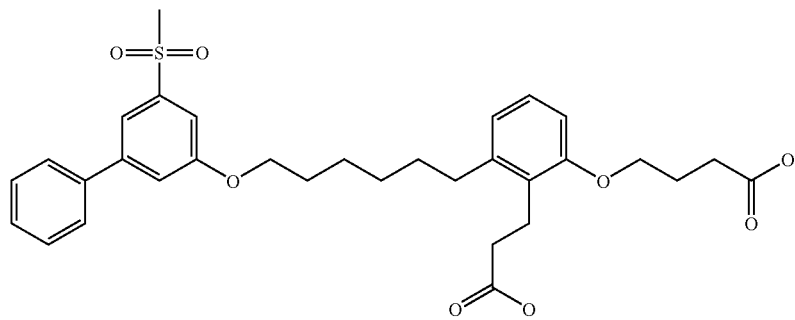

The title compound was prepared according to the general procedure for method F starting from 5-methanesulfonyl-biphenyl-3-ol. Yield: 42% (after two steps)

HRMS calcd for $C_{32}H_{38}O_8S$ [M+Na]$^+$ 605.2179, observed 605.2182

Example 29

4-{2-(2-Carboxy-ethyl)-3-[6-(5-methanesulfonyl-4'-methoxy-biphenyl-3-yloxy)-hexyl]-phenoxy}-butyric Acid

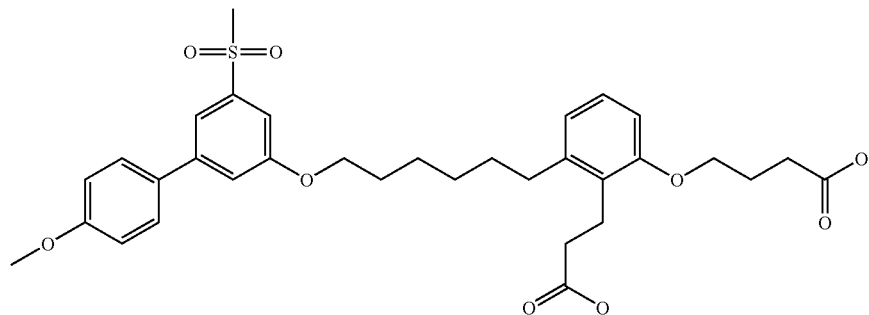

The title compound was prepared according to the general procedure for method F starting from 5-methanesulfonyl-4'-methoxy-biphenyl-3-ol. Yield: 52% (after two steps)

HRMS calcd for $C_{33}H_{40}O_9S$ $[M+Na]^+$ 635.2285, observed 635.2284

Example 30

4-{2-(2-Carboxy-ethyl)-3-[6-(4'-fluoro-5-methanesulfonyl-3'-methyl-biphenyl-3-yloxy)-hexyl]-phenoxy}-butyric Acid

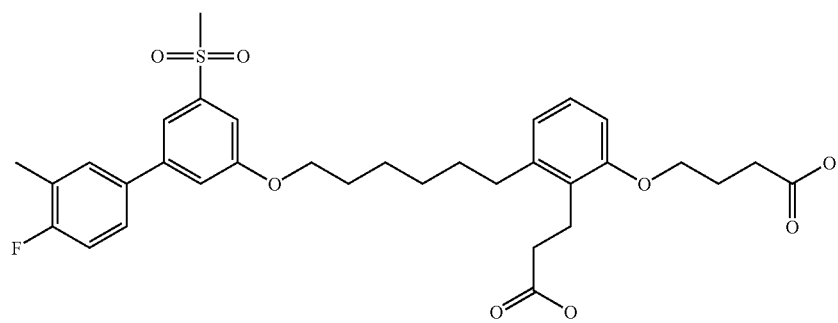

The title compound was prepared according to the general procedure for method F starting from 4'-fluoro-5-methanesulfonyl-3'-methyl-biphenyl-3-ol. Yield: 28% (after two steps)

HRMS calcd for $C_{33}H_{39}O_8FS$ $[M+Na]^+$ 637.2242, observed 637.2240

Example 31

4-{2-(2-Carboxy-ethyl)-3-[6-(3'-chloro-4'-fluoro-5-methanesulfonyl-biphenyl-3-yloxy)-hexyl]-phenoxy}-butyric Acid

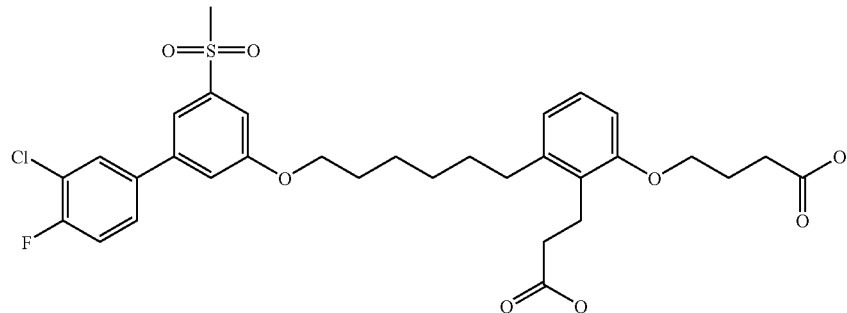

The title compound was prepared according to the general procedure for method F starting from 3'-chloro-4'-fluoro-5-methanesulfonyl-biphenyl-3-ol. Yield: 37% (after two steps)

HRMS calcd for $C_{32}H_{36}O_8ClFS$ $[M+Na]^+$ 657.1695, observed 657.1707

Example 32

4-{2-(2-Carboxy-ethyl)-3-[6-(2'-fluoro-5-methanesulfonyl-biphenyl-3-yloxy)-hexyl]-phenoxy}-butyric Acid

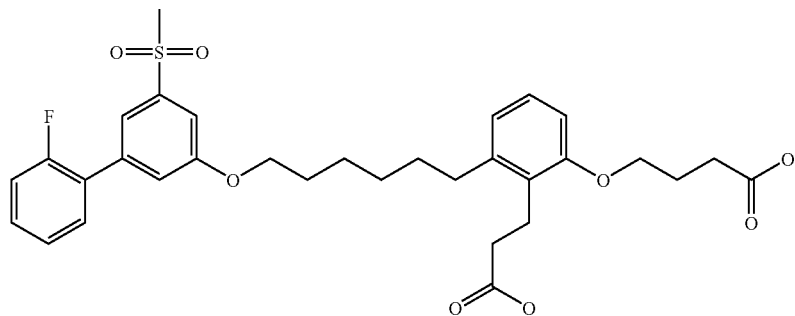

The title compound was prepared according to the general procedure for method F starting from 2'-fluoro-5-methanesulfonyl-biphenyl-3-ol. Yield: 80% (after two steps)

HRMS calcd for $C_{32}H_{37}O_8FS$ $[M+Na]^+$ 623.2085, observed 623.2089

Example 33

4-{2-(2-Carboxy-ethyl)-3-[6-(5-methanesulfonyl-2'-trifluoromethyl-biphenyl-3-yloxy)-hexyl]-phenoxy}-butyric Acid

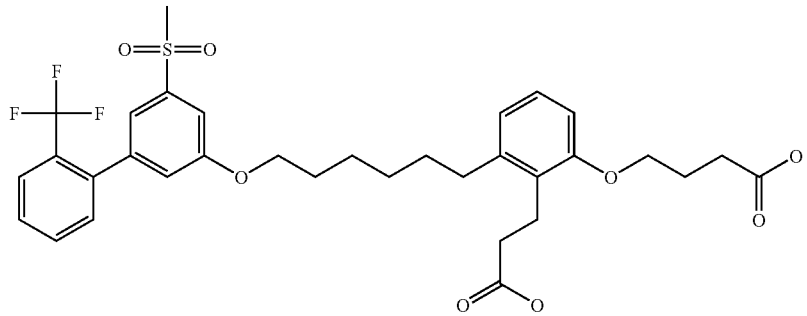

The title compound was prepared according to the general procedure for method F starting from 5-methanesulfonyl-2'-trifluoromethyl-biphenyl-3-ol. Yield: 65% (after two steps)

HRMS calcd for $C_{33}H_{37}O_8F_3S$ $[M+Na]^+$ 673.2053, observed 673.2050

Example 34

4-{2-(2-Carboxy-ethyl)-3-[6-(5-methanesulfonyl-3'-methyl-biphenyl-3-yloxy)-hexyl]-phenoxy}-butyric Acid

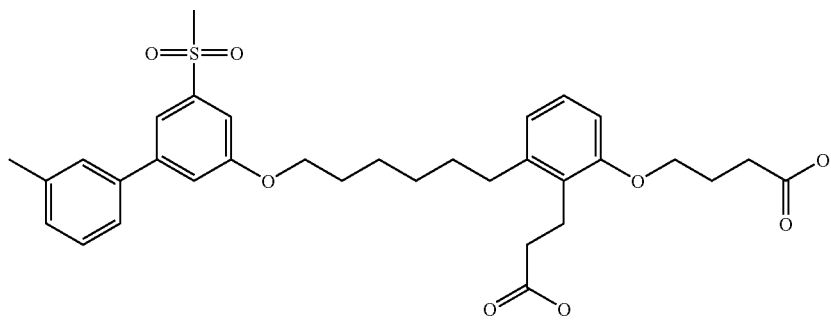

The title compound was prepared according to the general procedure for method F starting from 5-methanesulfonyl-3'-methyl-biphenyl-3-ol. Yield: 82% (after two steps)

HRMS calcd for $C_{33}H_{40}O_8S$ $[M+Na]^+$ 619.2336, observed 619.2337

Example 35

4-{2-(2-Carboxy-ethyl)-3-[6-(2'-chloro-5-methane-sulfonyl-biphenyl-3-yloxy)-hexyl]-phenoxy}-butyric Acid

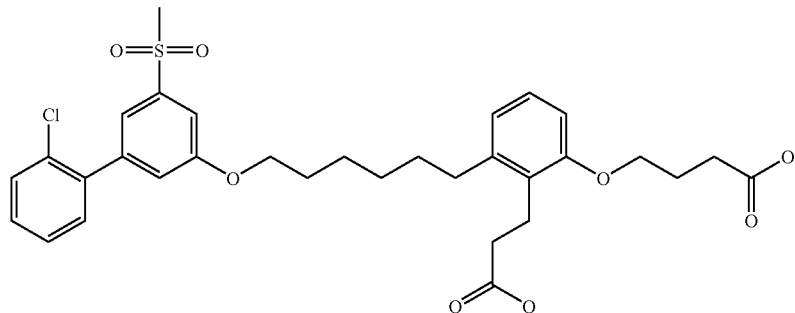

The title compound was prepared according to the general procedure for method F starting from 2'-chloro-5-methane-sulfonyl-biphenyl-3-ol. Yield: 76% (after two steps)

HRMS calcd for $C_{32}H_{37}O_8ClS$ [M+Na]$^+$ 639.1790, observed 639.1790

Example 36

4-{2-(2-Carboxy-ethyl)-3-[6-(5-methanesulfonyl-4'-trifluoromethoxy-biphenyl-3-yloxy)-hexyl]-phenoxy}-butyric Acid

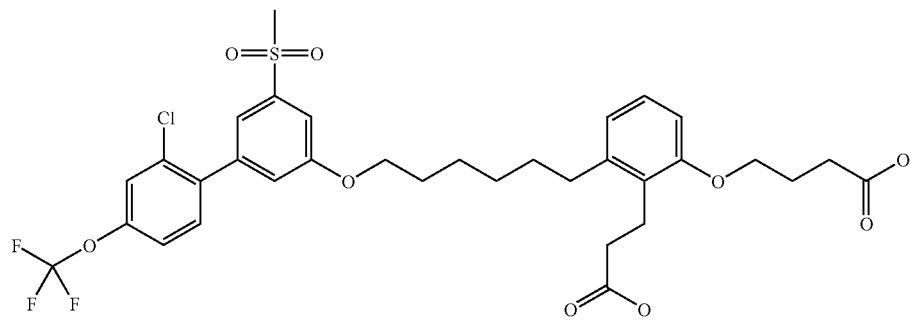

The title compound was prepared according to the general procedure for method F starting from 5-methanesulfonyl-4'-trifluoromethoxy-biphenyl-3-ol. Yield: 40% (after two steps)

HRMS calcd for $C_{33}H_{37}O_9F_3S$ [M+Na]$^+$ 689.2002, observed 689.2005

Example 37

4-{2-(2-Carboxy-ethyl)-3-[6-(3-methanesulfonyl-5-pyridin-2-yl-phenoxy)-hexyl]-phenoxy}-butyric Acid

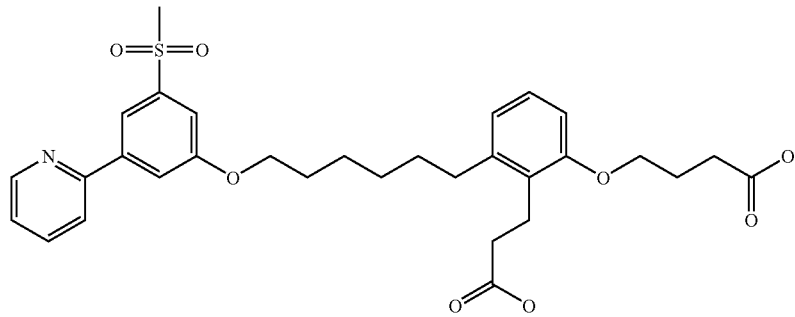

The title compound was prepared according to the general procedure for method F starting from 3-methanesulfonyl-5-pyridin-2-yl-phenol. Yield: 19% (after two steps)

HRMS calcd for $C_{31}H_{37}NO_8S$ [M+H]$^+$ 584.2313, observed 584.2312

Example 38

4-{2-(2-Carboxy-ethyl)-3-[6-(3-methanesulfonyl-5-pyridin-4-yl-phenoxy)-hexyl]-phenoxy}-butyric Acid

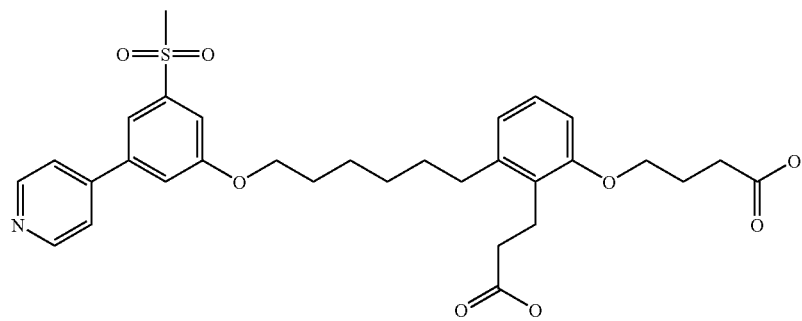

The title compound was prepared according to the general procedure for method F starting from 3-methanesulfonyl-5-pyridin-4-yl-phenol. Yield: 28% (after two steps)

HRMS calcd for $C_{31}H_{37}NO_8S$ [M+H]$^+$ 584.2313, observed 584.2309

Example 39

4-{2-(2-Carboxy-ethyl)-3-[6-(3-methanesulfonyl-5-thiophen-2-yl-phenoxy)-hexyl]-phenoxy}-butyric Acid

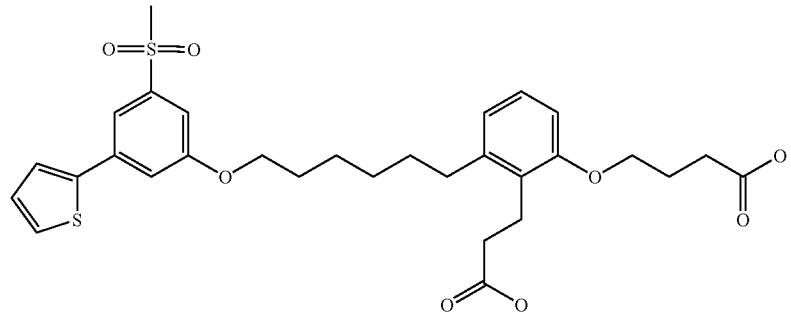

The title compound was prepared according to the general procedure for method F starting from 3-methanesulfonyl-5-thiophen-2-yl-phenol. Yield: 56% (after two steps)

HRMS calcd for $C_{30}H_{36}O_8S_2$ [M+Na]$^+$ 611.1744, observed 611.1744

Method G

Example 40

4-[3-[6-(3-Benzo[1,3]dioxol-5-yl-5-methanesulfonyl-phenoxy)-hexyl]-2-(2-carboxy-ethyl)-phenoxy]-butyric Acid

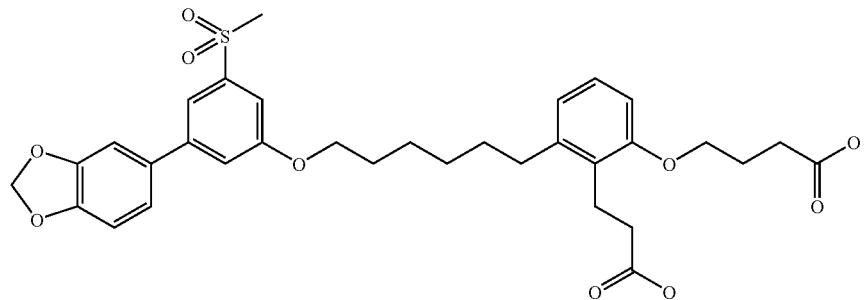

Step 1: Preparation of 1-methoxy-3-methylsulfanyl-5-nitro-benzene

To a solution of 3,5-dinitroanisole (5.0 g, 25.23 mmol) in dimethylsulfoxide (50 mL) were added methylthiotrimethylsilane (4.86 g, 40.37 mmol) and cesium carbonate (16.61 g, 50.46 mmol) at room temperature. The resulting dark green solution was stirred for 15 h at this temperature. Then, the reaction mixture was heated to 90° C. and the resulting brown mixture was stirred for another 5 h at which time TLC analysis of the mixture indicated the absence of starting material. The reaction mixture was cooled to room temperature and diluted with water (100 mL) and ethyl acetate (100 mL). The two layers were separated and the aqueous layer was extracted with ethyl acetate (50 mL). The combined extracts were washed with brine solution (150 mL) and dried over anhydrous magnesium sulfate. Filtration of the drying agent and the concentration of the solution under vacuum gave the crude residue which was purified by using an ISCO 120 column chromatography, eluting with 0-20% ethyl acetate in hexanes to obtain 1-methoxy-3-methylsulfanyl-5-nitro-benzene (1.44 g, 28.6%) as an yellow solid: EI(+)-HRMS m/e calcd for $C_8H_9NO_3S$ (M)$^+$ 199.0303, found 199.0294.

Step 2: Preparation of 1-methanesulfonyl-3-methoxy-5-nitro-benzene

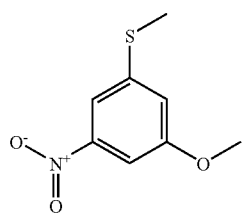

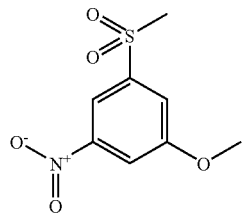

To a solution of 1-methoxy-3-methylsulfanyl-5-nitro-benzene (1.56 g, 7.83 mmol) in dichloromethane (48.75 mL) was added m-chloroperbenzoic acid (4.5 g, 15.66 mmol) at −10° C. The resulting white suspension was stirred for 10 min at −10° C. and then it was allowed to warm to room temperature. The resulting clear solution was stirred for 15 h at which time TLC analysis of the mixture indicated the absence of starting material. Then, the dichloromethane was removed under reduced pressure and the residue was dissolved in ethyl acetate (100 mL) and washed with saturated sodium bicarbonate solution (3×100 mL). Then, the ethyl acetate layer was washed with brine solution (100 mL) and dried over anhydrous magnesium sulfate, filtered, and concentrated in vacuo. Then, the crude residue was purified by using a silica gel column, eluting with 0-40% ethyl acetate in hexanes to afford 1-methanesulfonyl-3-methoxy-5-nitro-benzene (1.58 g, 87%) as a white solid: EI(+)-HRMS m/e calcd for $C_8H_9NO_5S$ $(M)^+$ 231.0204, found 231.0201.

Step 3: Preparation of
1-methanesulfonyl-5-methoxy-phenylamine

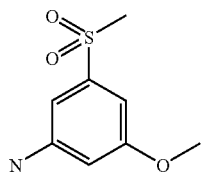

To a mixture of 1-methanesulfonyl-3-methoxy-5-nitro-benzene (1.5 g, 6.48 mmol), zinc dust (4.3 g, 64.87 mmol), and ammonium chloride (5.2 g, 97.31 mmol) were added methanol (20.32 mL) and water (9.9 mL) at room temperature. After addition of water, the reaction was exothermic. The suspension was stirred for 30 min and the reaction mixture was filtered through the Celite. The filter cake was washed with water and methanol. The filtrate was concentrated to remove methanol and the residue was extracted with ethyl acetate (2×50 mL). The combined extracts were washed with brine solution (100 mL), dried over anhydrous magnesium sulfate, filtered, and concentrated in vacuo to isolate 1-methanesulfonyl-5-methoxy-phenylamine (1.0 g, 76%) as a light yellow solid: ES(+)-HRMS m/e calcd for $C_8H_{12}NO_3S$ $(M+H)^+$ 202.0533, found 202.0532.

Step 4: Preparation of
3-iodo-1-methanesulfonyl-5-methoxy-benzene

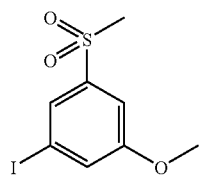

To a solution of 1-methanesulfonyl-5-methoxy-phenylamine (1.0 g, 4.94 mmol) in water (2.66 mL) was added a concentrated hydrochloric acid (2.21 mL, 29.66 mmol, 36%) at 0° C. To this mixture was added a chilled solution of sodium nitrite (0.622 g, 8.89 mmol) in water (3.78 mL) dropwise with a vigorous stirring. Then, the resulting colored mixture was stirred for 15 min at 0° C., and a cold solution of potassium iodide (1.64 g, 9.88 mmol) in water (3.78 mL) was added carefully. During this addition, a black brown solid was formed and after addition the ice bath was removed, and the reaction mixture was stirred for 2 days at room temperature. Then, the reaction mixture was diluted with water (50 mL) and saturated sodium thiosulfate solution (100 mL). The organic compound was extracted into ethyl acetate (3×50 mL). The combined organic extracts were washed with brine solution (100 mL) and dried over anhydrous magnesium sulfate. The filtration of the drying agent and concentration of the filtrate under reduced pressure gave the crude residue which was purified by using a silica gel column, eluting with 0-35% ethyl acetate in hexanes to obtain 3-iodo-1-methanesulfonyl-5-methoxy-benzene (1.08 g, 70%) as a white solid: ES(+)-HRMS m/e calcd for $C_8H_9IO_3S$ $(M+H)^+$ 312.9390, found 312.9390.

Step 5: Preparation of
3-iodo-5-methanesulfonyl-phenol

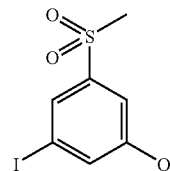

To a suspension of 3-iodo-1-methanesulfonyl-5-methoxy-benzene (1.03 g, 3.31 mmol) and sodium iodide (4.97 g, 33.15 mmol) in acetonitrile (30 mL) was added trimethylsilyl chloride (2.09 mL, 16.58 mmol) at room temperature. Then, the resulting light yellow suspension was heated to reflux for 48 h. Then, it was cooled to room temperature and diluted with water (50 mL). The organic compound was extracted into ethyl acetate (2×50 mL) and the combined ethyl acetate extracts were washed with saturated sodium thiosulfate solution (100 mL) to remove the iodine color and was also washed with brine solution (100 mL). Then, the organic layer was dried over anhydrous magnesium sulfate, filtered, and concentrated in vacuo. The crude residue was purified by using an ISCO 40 g column, eluting with 0-25% ethyl acetate in hexanes to obtain 3-iodo-5-methanesulfonyl-phenol (628 mg, 63.5%) as a light brown solid: ES(+)-HRMS m/e calcd for $C_7H_7IO_3S$ $(M+H)^+$ 298.9234, found 298.9234.

Step 6: Preparation of 4-{2-(2-ethoxycarbonyl-ethyl)-3-[6-(3-iodo-5-methanesulfonyl-phenoxy)-hexyl]-phenoxy}-butyric Acid Ethyl Ester

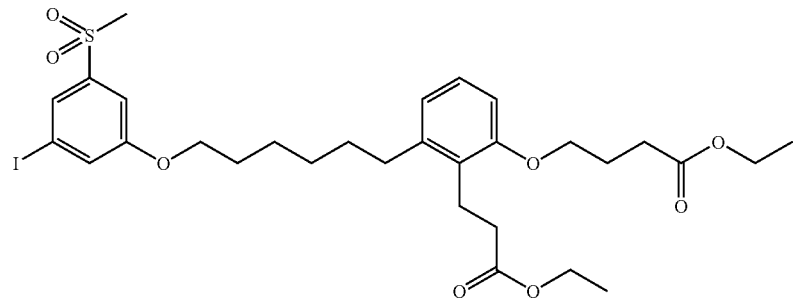

To a mixture of 4-[3-(6-bromo-hexyl)-2-(2-ethoxycarbonyl-ethyl)-phenoxy]-butyric acid ethyl ester (1.17 g, 2.49 mmol), 3-iodo-5-methanesulfonyl-phenol (620 mg, 2.08 mmol), and potassium carbonate (575 mg, 4.16 mmol) were added dimethylformamide (13.4 mL) and acetone (26.8 mL) at room temperature. The resulting suspension was heated to reflux for 2 days. Then, the reaction mixture was cooled to room temperature and diluted with water (100 mL). The organic compound was extracted into ethyl acetate (3×50 mL) and the combined organic extracts were washed with water (100 mL) and brine solution (100 mL). The organic layers were dried over anhydrous magnesium sulfate and filtration of the drying agent and concentration of the solvent gave the crude product which was purified by using an ISCO 40 g column, eluting with 2-20% ethyl acetate in hexanes to afford 4-{2-(2-ethoxycarbonyl-ethyl)-3-[6-(3-iodo-5-methanesulfonyl-phenoxy)-hexyl]-phenoxy}-butyric acid ethyl ester (1.3 g, 91%) as a colorless oil: ES(+)-HRMS m/e calcd for $C_{30}H_{41}IO_8S$ (M+Na)$^+$ 711.1459, found 711.1460.

and diluted with water (50 mL) and ethyl acetate (50 mL). The two layers were separated and the aqueous layer was extracted with ethyl acetate (2×50 mL). The combined organic extracts were washed with water (100 mL) and brine solution (100 mL). The organic layer was dried over anhydrous magnesium sulfate and filtration of the drying agent and removal of the solvent under reduced pressure gave the colored residue which was purified by using an ISCO 80 g column, eluting with 0-20% ethyl acetate in hexanes to afford 4-[3-[6-(3-benzo[1,3]dioxol-5-yl-5-methanesulfonyl-phenoxy)-hexyl]-2-(2-ethoxycarbonyl-ethyl)-phenoxy]-butyric acid ethyl ester (972 mg, 86%) as a light brown viscous oil: ES(+)-HRMS m/e calcd for $C_{37}H_{46}O_{10}S$ (M+Na)$^+$ 705.2704, found 705.2703.

Step 7: Preparation of 4-[3-[6-(3-benzo[1,3]dioxol-5-yl-5-methanesulfonyl-phenoxy)-hexyl]-2-(2-ethoxycarbonyl-ethyl)-phenoxy]-butyric Acid Ethyl Ester Step 8: Preparation of 4-[3-[6-(3-benzo[1,3]dioxol-5-yl-5-methanesulfonyl-phenoxy)-hexyl]-2-(2-carboxy-ethyl)-phenoxy]-butyric Acid

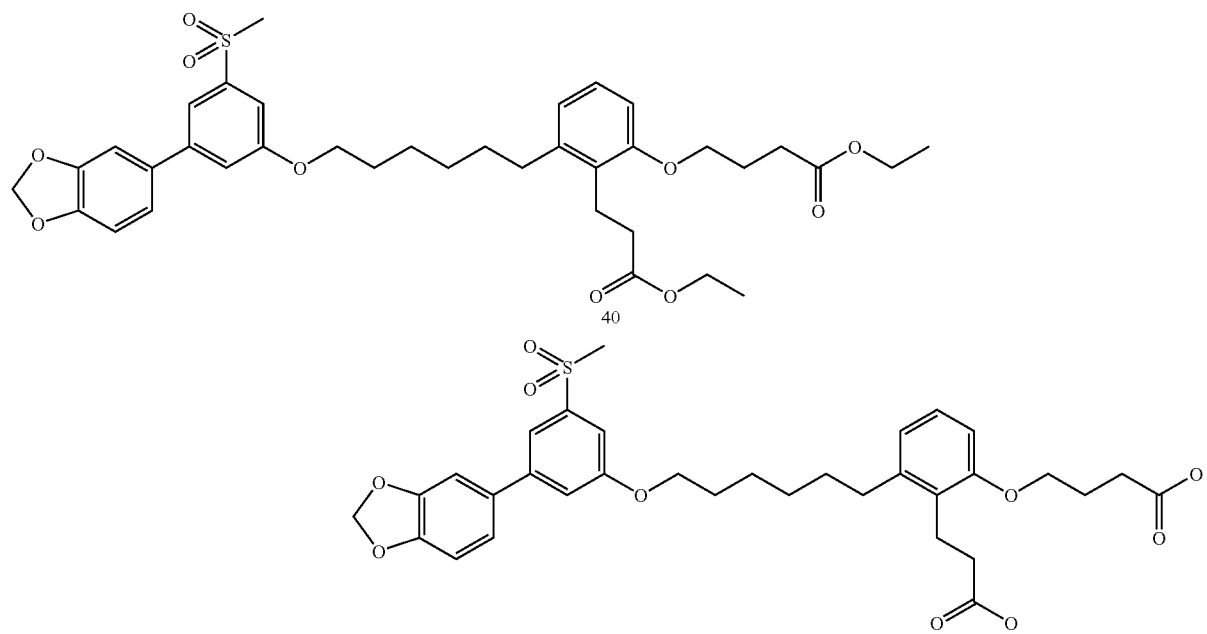

A solution of 4-{2-(2-ethoxycarbonyl-ethyl)-3-[6-(3-iodo-5-methanesulfonyl-phenoxy)-hexyl]-phenoxy}-butyric acid ethyl ester (1.14 g, 1.65 mmol) in dimethoxyethane (15 mL) was stirred for 5 minutes at room temperature under nitrogen atmosphere. Then, tetrakis(triphenylphosphine)palladium(0) (386 mg, 0.33 mmol) was added at room temperature and the resulting light yellow solution was heated to 80° C. and stirred for 5 minutes. At this period, a solution of 3,4-(methylenedioxyphenyl)boronic acid (566 g, 3.3 mmol) in ethanol (16 mL) was added followed by a solution of sodium carbonate (351 mg, 3.3 mmol) in water (1.0 mL). The resulting light yellow suspension was stirred for 15 h at reflux. Then, the reaction mixture was cooled to room temperature To a solution of the 4-[3-[6-(3-benzo[1,3]dioxol-5-yl-5-methanesulfonyl-phenoxy)-hexyl]-2-(2-ethoxycarbonyl-ethyl)-phenoxy]-butyric acid ethyl ester (26.7 g, 39.1 mmol) in THF (200 mL) and ethanol (200 mL) was added aqueous 1.0 N sodium hydroxide (200 mL) at room temperature. The resulting suspension was heated to 45-50° C. and the mixture was stirred for 30 min and then cooled to room temperature and stirred for 15 h at which time TLC analysis of the mixture indicated the absence of starting material. Then, the reaction mixture was concentrated and the residue was diluted with water (200 mL) and extracted with diethyl ether (150 mL) to remove any neutral impurities. The aqueous layer was acidified with 1.0 N hydrochloric acid and the precipitated white organic compound was extracted into ethyl acetate (2×200 mL). The combined ethyl acetate extracts were washed with brine solution (300 mL) and the organic layers were dried over anhydrous magnesium sulfate. Filtration of the drying agent and removal of the solvent afforded the crude product which was dissolved in acetonitrile (270 mL) at hot condition and was stored in the refrigerator. The resulting white solids were collected by filtration and washed with acetonitrile. After air-drying, 4-[3-[6-(3-benzo[1,3]dioxol-5-yl-5-methanesulfonyl-phenoxy)-hexyl]-2-(2-carboxy-ethyl)-phenoxy]-butyric acid (19.7 g, 80.5%) was isolated as a white solid. ES(+)-HRMS m/e calcd for $C_{33}H_{38}O_{10}S$ (M+Na)$^+$ 649.2078, found 649.2076.

Example 41

4-(2-(2-Carboxy-ethyl)-3-{6-[3-(2,3-dihydro-benzo[1,4]dioxin-6-yl)-5-methanesulfonyl-phenoxy]-hexyl}-phenoxy)-butyric Acid

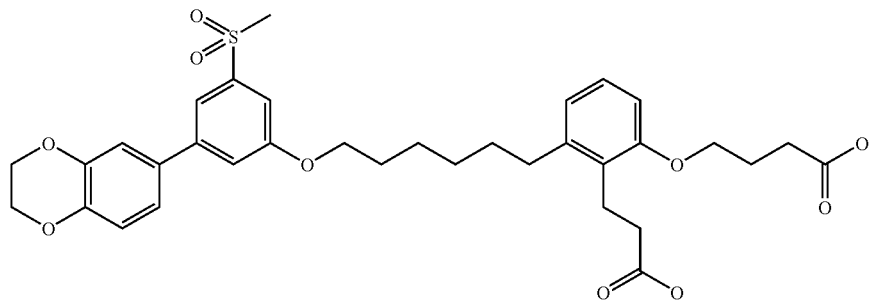

Step 1: Preparation of 4-(3-{6-[3-(2,3-dihydro-benzo[1,4]dioxin-6-yl)-5-methanesulfonyl-phenoxy]-hexyl}-2-(2-ethoxycarbonyl-ethyl)-phenoxy)-butyric Acid Ethyl Ester

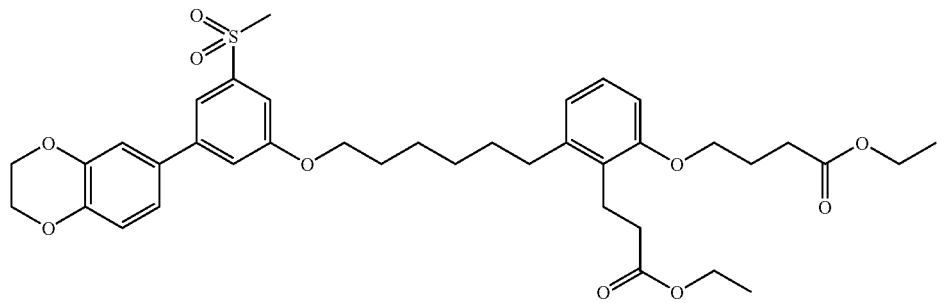

A mixture of 4-{2-(2-ethoxycarbonyl-ethyl)-3-[6-(3-iodo-5-methanesulfonyl-phenoxy)-hexyl]-phenoxy}-butyric acid ethyl ester (646 mg, 0.94 mmol), 1,4-benzodioxaneboronic acid (337 g, 1.87 mmol), [1,1'-bis(diphenylphosphino)ferrocene]dichloropalladium(II) (103 mg, 0.14 mmol), and cesium carbonate(617 mg, 1.87 mmol) was added at room temperature under nitrogen atmosphere. The resulting brown reaction mixture was heated to 96° C. and stirred for 15 h at which time the TLC of the reaction mixture indicated the absence of starting material. Then, the reaction mixture was cooled to room temperature and diluted with water (50 mL) and ethyl acetate (50 mL). removal of the solvent under reduced pressure gave the colored residue which was purified by using an ISCO 80 column, eluting with 5-25% ethyl acetate in hexanes to afford 4-(3-{6-[3-(2,3-dihydro-benzo[1,4]dioxin-6-yl)-5-methanesulfonyl-phenoxy]-hexyl}-2-(2-ethoxycarbonyl-ethyl)-phenoxy)-butyric acid ethyl ester (336 mg, 51%) as a light brown viscous oil: ES(+)-LRMS m/e calcd for $C_{38}H_{48}O_{10}S$ (M+H)$^+$ 697.3, found 697.23.

Step 2: Preparation of 4-(2-(2-carboxy-ethyl)3-{6-[3-(2,3-dihydro-benzo[1,4]dioxin-6-yl)-5-methane-sulfonyl-phenoxy]-hexyl}-phenoxy)-butyric Acid

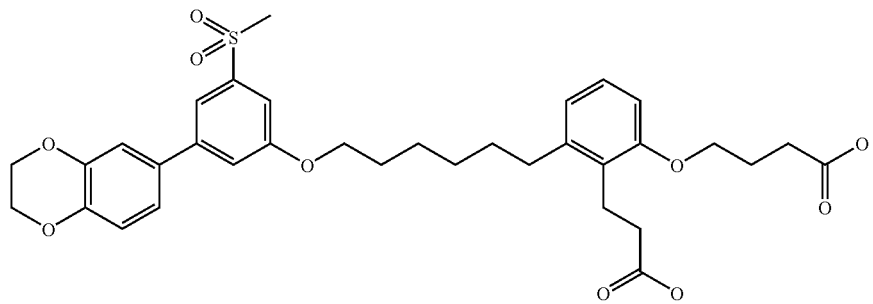

A similar procedure as described in Example 40, step 8 was used, starting from 4-(2-(2-ethoxycarbonyl-ethyl)-3-{6-[3-(2,3-dihydro-benzo[1,4]dioxin-6-yl)-5-methanesulfonyl-phenoxy]-hexyl}-phenoxy)-butyric acid ethyl ester (330 mg, 0.47 mmol) and 1.0 N aqueous sodium hydroxide (4.74 mL) to afford 4-(2-(2-carboxy-ethyl)-3-{6-[3-(2,3-dihydro-benzo[1,4]dioxin-6-yl)-5-methanesulfonyl-phenoxy]-hexyl}-phenoxy)-butyric acid (210 mg, 69%) as a white solid: ES(+)-HRMS m/e calcd for $C_{34}H_{40}O_{10}S$ $(M+Na)^+$ 663.2234, found 663.2229.

Example 42

4-[2-(2-Carboxy-ethyl)-3-[6-(5-methanesulfonyl-3',4'-difluoro-biphenyl-3-yloxy)-hexyl]-phenoxy]-butyric Acid

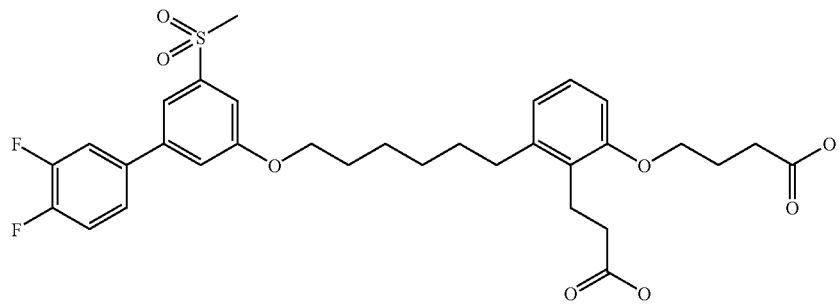

Step 1: Preparation of 4-[2-(2-ethoxycarbonyl-ethyl)-3-[6-(5-methanesulfonyl-3',4'-difluoro-biphenyl-3-yloxy)-hexyl]-phenoxy]-butyric Acid Ethyl Ester

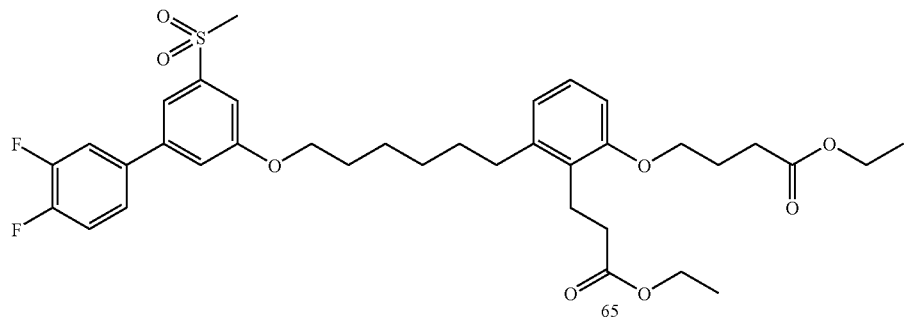

A similar procedure as described in Example 41, step 1 was used, starting from 4-{2-(2-ethoxycarbonyl-ethyl)-3-[6-(3- iodo-5-methanesulfonyl-phenoxy)-hexyl]-phenoxy}-butyric acid ethyl ester (500 mg, 0.73 mmol), 3,4-difluorophenylboronic acid (236 mg, 1.45 mmol), [1,1'-bis(diphenylphosphino)ferrocene]dichloropalladium(II) (79.7 mg, 0.109 mmol), and cesium carbonate (477.9 mg, 1.45 mmol) to afford 4-[2-(2-ethoxycarbonyl-ethyl)-3-[6-(5-methanesulfonyl-3',4'-difluoro-biphenyl-3-yloxy)-hexyl]-phenoxy]-butyric acid ethyl ester (207 mg, 42.2%) as a light yellow viscous oil: ES(+)-HRMS m/e calcd for $C_{36}H_{44}F_2O_8S$ (M+Na)$^+$ 697.2617, found 697.2611.

Step 2: Preparation of 4-[2-(2-carboxy-ethyl)-3-[6-(5-methanesulfonyl-3',4'-difluoro-biphenyl-3-yloxy)-hexyl]-phenoxy]-butyric Acid

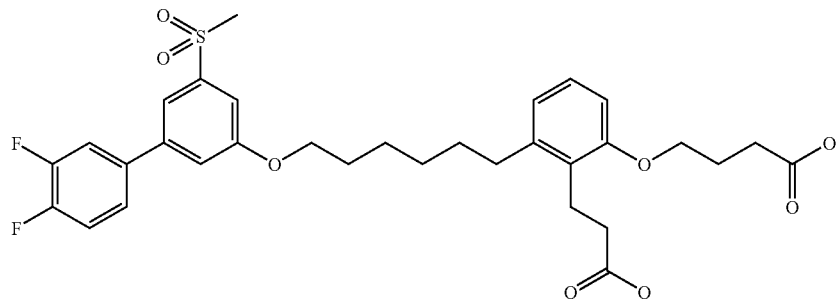

A similar procedure as described in Example 40, step 8 was used, starting from 4-[2-(2-ethoxycarbonyl-ethyl)-3-[6-(5-methanesulfonyl-3',4'-difluoro-biphenyl-3-yloxy)-hexyl]-phenoxy]-butyric acid ethyl ester (200 mg, 0.296 mmol) and 1.0 N aqueous sodium hydroxide (2.96 mL) to afford 4-[2-(2-carboxy-ethyl)-3-[6-(5-methanesulfonyl-3',4'-difluoro-biphenyl-3-yloxy)-hexyl]-phenoxy]-butyric acid (92 mg, 50%) as an amorphous white solid: ES(+)-HRMS m/e calcd for $C_{32}H_{36}F_2O_8S$ (M+Na)$^+$ 641.1991, found 641.1988.

Example 43

4-[3-[6-(5,4'-Bis-methanesulfonyl-biphenyl-3-yloxy)-hexyl]-2-(2-carboxy-ethyl)-phenoxy]-butyric Acid

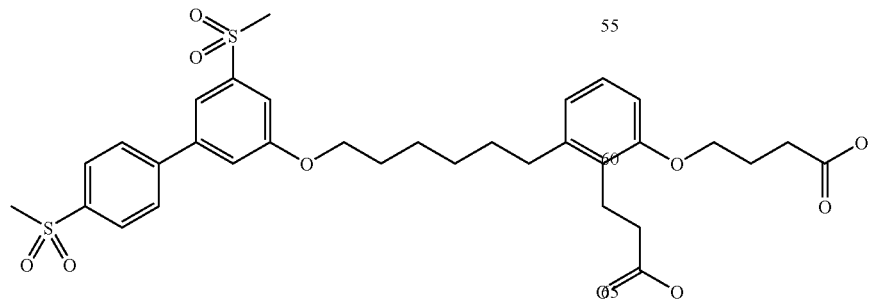

Step 1: Preparation of 4-[3-[6-(5,4'-bis-methane-sulfonyl-biphenyl-3-yloxy)-hexyl]-2-(2-ethoxycarbonyl-ethyl)-phenoxy]-butyric Acid Ethyl Ester

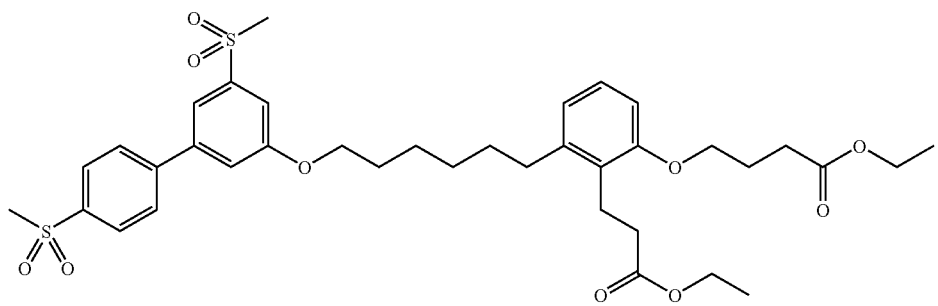

A similar procedure as described in Example 41, step 1 was used, starting from 4-{2-(2-ethoxycarbonyl-ethyl)-3-[6-(3-iodo-5-methanesulfonyl-phenoxy)-hexyl]-phenoxy}-butyric acid ethyl ester (257 mg, 0.37 mmol), 4-methanesulfonylphenylboronic acid (153.8 mg, 0.75 mmol), [1,1'-bis(diphenylphosphino)ferrocene]dichloropalladium(II) (40.9 mg, 0.056 mmol), and cesium carbonate (245.5 mg, 0.75 mmol) to afford 4-[3-[6-(5,4'-bis-methanesulfonyl-biphenyl-3-yloxy)-hexyl]-2-(2-ethoxycarbonyl-ethyl)-phenoxy]-butyric acid ethyl ester (71 mg, 26.4%) as a light brown viscous oil: ES(+)-HRMS m/e calcd for $C_{37}H_{48}O_{10}S_2$ $(M+H)^+$ 717.2762, found 717.2758.

Step 2: Preparation of 4-[3-[6-(5,4'-bis-methane-sulfonyl-biphenyl-3-yloxy)-hexyl]-2-(2-carboxy-ethyl)-phenoxy]-butyric Acid

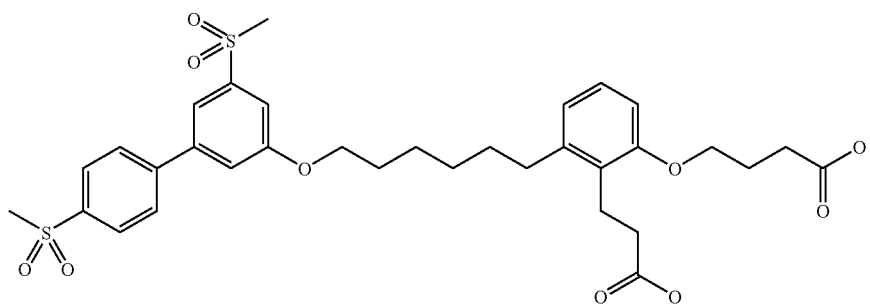

A similar procedure as described in Example 40, step 8 was used, starting from 4-[3-[6-(5,4'-bis-methanesulfonyl-biphenyl-3-yloxy)-hexyl]-2-(2-ethoxycarbonyl-ethyl)-phenoxy]-butyric acid ethyl ester (67 mg, 0.09 mmol) and 1.0 N aqueous sodium hydroxide (0.9 mL) to afford 4-[3-[6-(5,4'-bis-methanesulfonyl-biphenyl-3-yloxy)-hexyl]-2-(2-carboxy-ethyl)-phenoxy]-butyric acid (35 mg, 57%) as an amorphous white solid: ES(+)-HRMS m/e calcd for $C_{33}H_{40}O_{10}S_2$ $(M+Na)^+$ 683.1955, found 683.1954.

Example 44

4-(2-(2-Carboxy-ethyl)-3-{6-[3-methanesulfonyl-5-(1H-pyrazol-3-yl)-phenoxy]-hexyl}-phenoxy)-butyric Acid

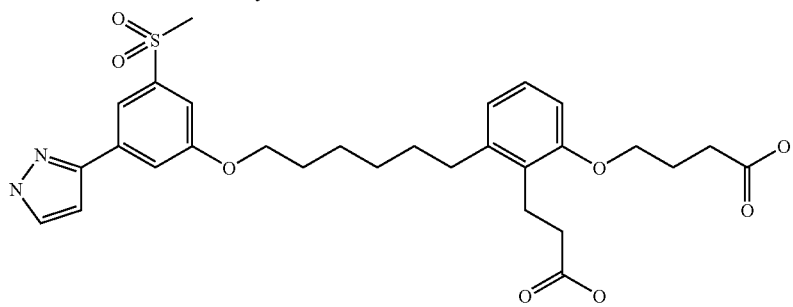

Step 1: Preparation of 4-(2-(2-ethoxycarbonyl-ethyl)-3-{6-[3-methanesulfonyl-5-(1H-pyrazol-3-yl)-phenoxy]-hexyl}-phenoxy)-butyric Acid Ethyl Ester

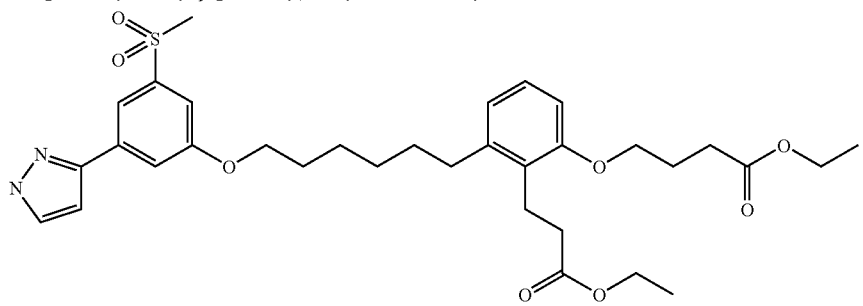

A similar procedure as described in Example 40, step 7 was used, starting from 4-{2-(2-ethoxycarbonyl-ethyl)-3-[6-(3-iodo-5-methanesulfonyl-phenoxy)-hexyl]-phenoxy}-butyric acid ethyl ester (150 mg, 0.22 mmol), 1H-pyrazol-3-ylboronic acid (51.4 mg, 0.45 mmol), tetrakis(triphenylphosphine)palladium(0) (50.8 mg, 0.04 mmol), and potassium carbonate (30.2 mg, 0.22 mmol) to afford 4-(2-(2-ethoxycarbonyl-ethyl)-3-{6-[3-methanesulfonyl-5-(1H-pyrazol-3-yl)-phenoxy]-hexyl}-phenoxy)-butyric acid ethyl ester (39 mg, 28.5%) as a light brown viscous oil: ES(+)-HRMS m/e calcd for $C_{33}H_{44}N_2O_8S$ (M+H)$^+$ 629.2891, found 629.2894.

Step 2: Preparation of 4-(2-(2-carboxy-ethyl)-3-{6-[3-methanesulfonyl-5-(1H-pyrazol-3-yl)-phenoxy]-hexyl}-phenoxy)-butyric Acid

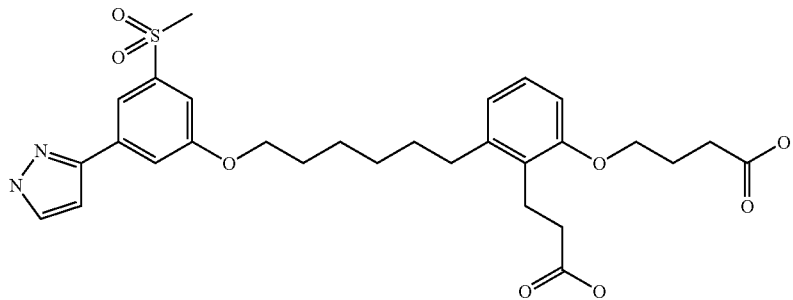

A similar procedure as described in Example 40, step 8 was used, starting from 4-(2-(2-ethoxycarbonyl-ethyl)-3-{6-[3- methanesulfonyl-5-(1H-pyrazol-3-yl)-phenoxy]-hexyl}-phenoxy)-butyric acid ethyl ester (35 mg, 0.05 mmol) and 1.0 N aqueous sodium hydroxide (0.4 mL) to afford 4-(2-(2-carboxy-ethyl)-3-{6-[3-methanesulfonyl-5-(1H-pyrazol-3-yl)-phenoxy]-hexyl}-phenoxy)-butyric acid (24 mg, 75%) as an amorphous white solid: ES(+)-HRMS m/e calcd for $C_{29}H_{36}N_2O_8S$ (M+Na)$^+$ 595.2084, found 595.2080.

Example 45

4-[3-[6-(3-Benzothiazol-5-yl-5-methanesulfonyl-phenoxy)-hexyl]-2-(2-carboxy-ethyl)-phenoxy]-butyric Acid

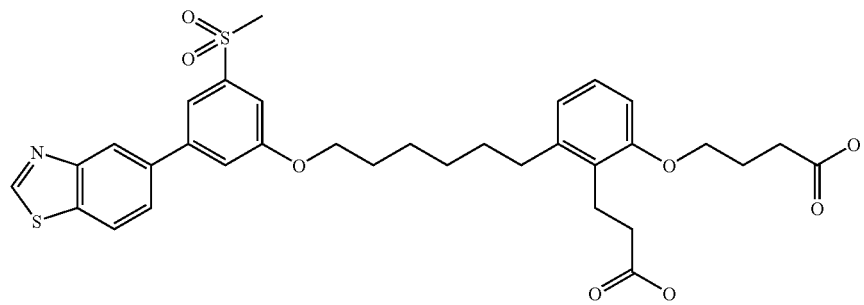

Step 1: Preparation of 4-[3-[6-(3-benzothiazol-5-yl-5-methanesulfonyl-phenoxy)-hexyl]-2-(2-ethoxycarbonyl-ethyl)-phenoxy]-butyric Acid Ethyl Ester

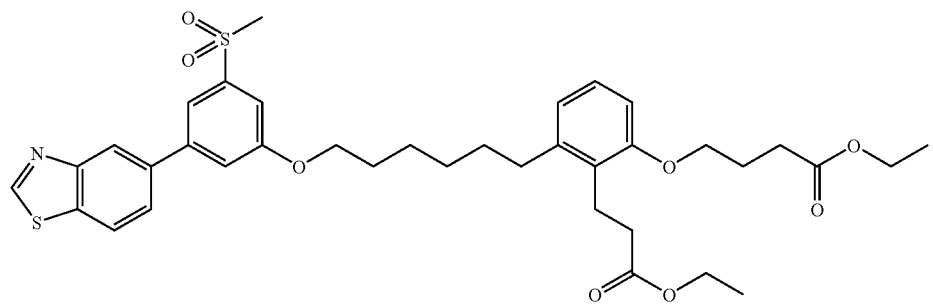

To a mixture of benzothiazole-5-ylboronic acid pinacol ester (151.5 mg, 0.58 mmol), palladium acetate(II) (6.6 mg, 0.029 mmol), and triphenylphosphine (15.4 mg, 0.058 mmol) in dioxane (5 mL) were added 4-{2-(2-ethoxycarbonyl-ethyl)-3-[6-(3-iodo-5-methanesulfonyl-phenoxy)-hexyl]-phenoxy}-butyric acid ethyl ester (200 mg, 0.29 mmol), potassium phosphate (126.9 mg, 0.58 mmol), and water (10 mg) at room temperature under nitrogen atmosphere. Then, the brown reaction mixture was heated to 100° C. and stirred for 2 h at which time the TLC of the reaction mixture indicated the absence of starting material. Then, the reaction mixture was cooled to room temperature and diluted with water (50 mL) and ethyl acetate (50 mL). The two layers were separated and the aqueous layer was extracted with ethyl acetate (50 mL) and the combined organic extracts were washed with water (100 mL) and brine solution (100 mL). The organic layer was dried over anhydrous magnesium sulfate and filtration of the drying agent and removal of the solvent under reduced pressure gave the colored residue which was purified by using an ISCO 40 g column, eluting with 2-25% ethyl acetate in hexanes to afford 4-[3-[6-(3-benzothiazol-5-yl-5-methanesulfonyl-phenoxy)-hexyl]-2-(2-ethoxycarbonyl-ethyl)-phenoxy]-butyric acid ethyl ester (110 mg, 54.4%) as a light brown solid: ES(+)-HRMS m/e calcd for $C_{37}H_{45}NO_8S_2$ (M+H)$^+$ 696.2660, found 696.2658.

Step 2: Preparation of 4-[3-[6-(3-benzothiazol-5-yl-5-methanesulfonyl-phenoxy)-hexyl]-2-(2-carboxy-ethyl)-phenoxy]-butyric Acid

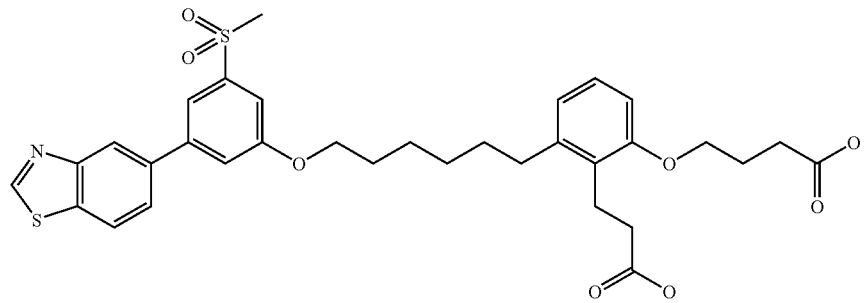

A similar procedure as described in Example 40, step 8 was used, starting from 4-[3-[6-(3-benzothiazol-5-yl-5-methanesulfonyl-phenoxy)-hexyl]-2-(2-ethoxycarbonyl-ethyl)-phenoxy]-butyric acid ethyl ester (100 mg, 0.14 mmol) and 1.0 N aqueous sodium hydroxide (1.44 mL) to afford 4-[3-[6-(3-benzothiazol-5-yl-5-methanesulfonyl-phenoxy)-hexyl]-2-(2-carboxy-ethyl)-phenoxy]-butyric acid (50 mg, 54.4%) as an amorphous white solid: ES(+)-HRMS m/e calcd for $C_{33}H_{37}NO_8S_2$ (M+H)$^+$ 640.2034, found 640.2030.

Method H

Example 46

4-(2-(2-Carboxy-ethyl)-3-{6-[3-(2,2-difluoro-benzo[1,3]dioxol-5-yl)-5-methanesulfonyl-phenoxy]-hexyl}-phenoxy)-butyric Acid

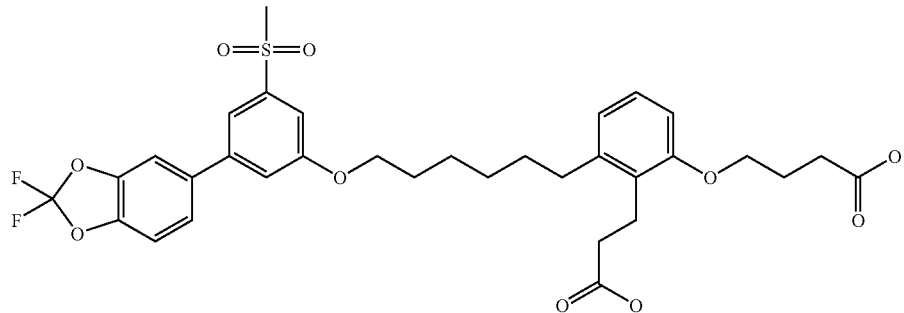

Step 1: Preparation of 2,2-difluoro-benzo[1,3]dioxole-5-boronic Acid

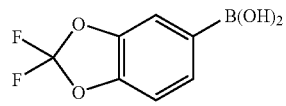

n-BuLi in hexanes (2.5 M solution, 46 mL) was added to anhydrous THF (250 mL) cooled in acetone-dry ice bath under the flow of nitrogen. After 10 min 5-bromo-2,2-difluoro-1,3-benzodioxole (25.0 g) was added dropwise and the resulting solution was stirred for 30 min. Then, boron isopropoxide (30 mL) was added dropwise and the reaction mixture was allowed to reach room temperature over a period of 3 h. Then acetic acid (30 mL) was added in one portion and the resulting mixture was stirred at room temperature for 10 min. The reaction mixture was then diluted with ethyl acetate and washed with water and brine. The organic extract was dried over anhydrous sodium sulfate and concentrated under reduced pressure. The title compound was obtained by trituration with hexanes as a white solid (14.2 g, 73% yield). HRMS calcd for $C_7H_5O_4BF_2$ $[2M-H-H_2O]^-$ 385.0324, observed 385.0319.

stirred at 75° C. for 5 h. Over the period of 4 hours additional amount of sodium methoxide (total 754 mg) was added in two equal portions. When the starting material was completely consumed the reaction mixture was diluted with ethyl acetate and washed with water and brine. The organic extract was dried over anhydrous sodium sulfate, concentrated under reduced pressure and purified on a silica gel column using ethyl acetate and hexanes to yield the title compound (2.1 g, 60% yield). HRMS calcd for $C_{15}H_{15}O_2BrS$ $[M+H]^+$ 339.0049, observed 339.0047.

Step 2: 1,3-Dibromo-5-(4-methoxy-benzyloxy)-benzene

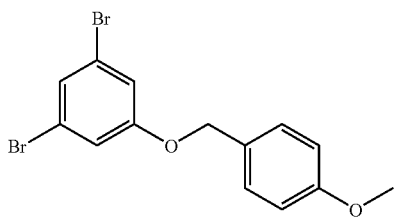

3,5-Dibromophenol (10.0 g), 4-methoxybenzyl bromide (8.8 g) and potassium carbonate (27.3 g) were combined in acetone (300 mL) and refluxed for 3 h. Then the insoluble material was removed by filtration, the filtrate was concentrated under reduced pressure and the resulting crude oil was purified on a silica gel column using ethyl acetate and hexanes to give light yellow oil which was then crystallized from hexanes to give the title compound (12.1 g, 82% yield). HRMS calcd for $C_{14}H_{12}O_2Br_2$ $M^+$ 369.9203, observed 369.9198.

Step 3: 1-Bromo-3-(4-methoxy-benzyloxy)-5-methylsulfanyl-benzene

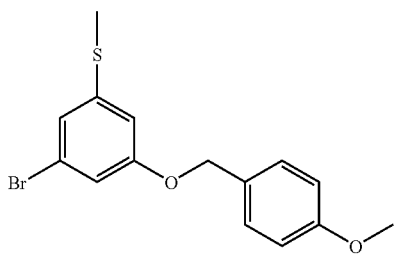

1,3-Dibromo-5-(4-methoxy-benzyloxy)-benzene (4.0 g) was dissolved in DMF (60 mL), followed by addition of sodium thiomethoxide (829 mg). The resulting mixture was

Step 4: 1-Bromo-3-methanesulfonyl-5-(4-methoxybenzyloxy)-benzene

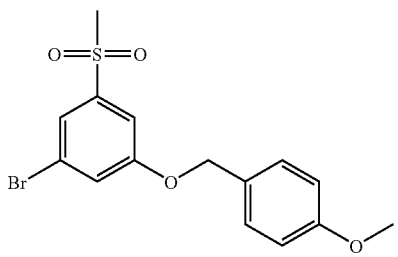

To a solution of 1-bromo-3-(4-methoxy-benzyloxy)-5-methylsulfanyl-benzene (7.4 g) in dichloromethane (200 mL) was added mcpba (11.4 g) and the resulting mixture was stirred at room temperature for 3 h. Then the solution was washed with sodium bicarbonate, water and brine. The organic extract was dried over anhydrous sodium sulfate, concentrated under reduced pressure and purified on a silica gel column using ethyl acetate and hexanes to yield the title compound (5.0 g, 62% yield). HRMS calcd for $C_{15}H_{15}O_4BrS$ $[M+Na]^+$ 392.9766, observed 392.9768.

Step 5: 3-Bromo-5-methanesulfonyl-phenol

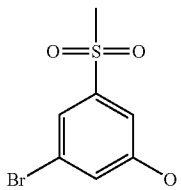

Bromo-3-methanesulfonyl-5-(4-methoxy-benzyloxy)-benzene (5.7 g) was dissolved in glacial acetic acid (80 mL) and stirred at 100° C. for 5 h. The solvent was removed under reduced pressure and the crude material was purified on a silica gel column using ethyl acetate and hexanes to yield the title compound (3.4 g, 88% yield)

HRMS calcd for $C_7H_7O_3BrS$ $[M-H]^-$ 248.9226, observed 248.9227

Step 6: 4-[3-[6-(3-Bromo-5-methanesulfonyl-phenoxy)-hexyl]-2-(2-ethoxycarbonyl-ethyl)-phenoxy]-butyric Acid Ethyl Ester

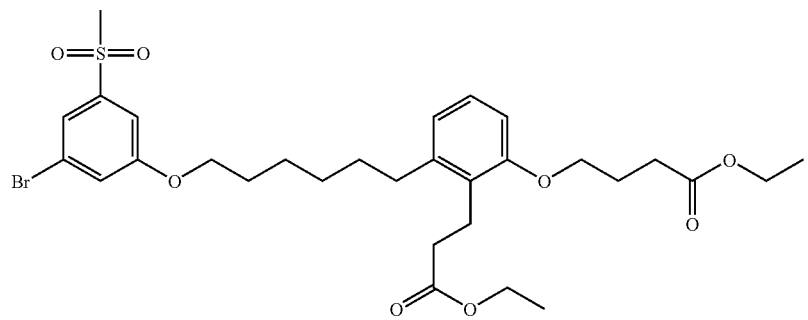

To a solution of 3-bromo-5-methanesulfonyl-phenol (1.3 g) in a mixture of acetone and DMF (2:1, 60 mL) were added potassium carbonate (7.1 g) and 4-[3-(6-bromo-hexyl)-2-(2-ethoxycarbonyl-ethyl)-phenoxy]-butyric acid ethyl ester (2.7 g). The resulting mixture was stirred at 75° C. for 1 day. Then the insoluble material was filtered out and the filtrate was diluted with ethyl acetate and washed with water and brine. The organic extract was dried over anhydrous sodium sulfate, concentrated and purified on a silica gel column using ethyl acetate and hexanes to yield the title compound (2.9 g, 87% yield). LRMS calcd for $C_{30}H_{41}O_8BrS$ $[M+H]^+$ 641.2, observed 641.1.

Step 7: 4-[3-{6-[3-(2,2-Difluoro-benzo[1,3]dioxol-5-yl)-5-methanesulfonyl-phenoxy]-hexyl}-2-(2-ethoxycarbonyl-ethyl)-phenoxy]-butyric Acid Ethyl Ester

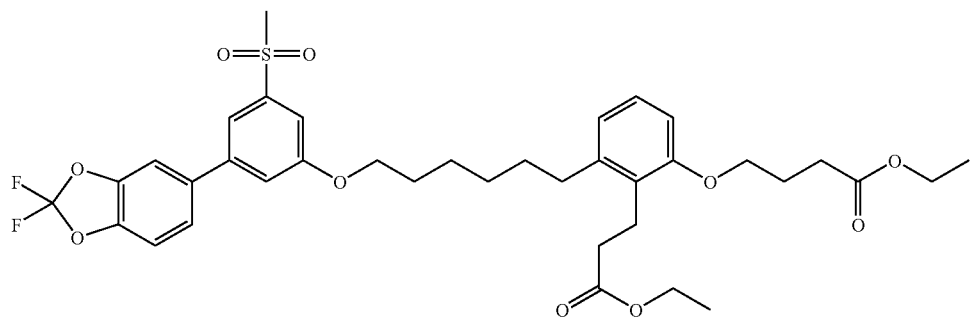

To a solution of 4-[3-[6-(3-bromo-5-methanesulfonyl-phenoxy)-hexyl]-2-(2-ethoxycarbonyl-ethyl)-phenoxy]-butyric acid ethyl ester (1.0 g) in 1,2-dimethoxyethane (80 mL) were added 2,2-difluoro-benzo[1,3]dioxole-5-boronic acid (430 mg), 2 M aq. sodium carbonate solution (3.1 mL) and $Pd(PPh_3)_4$ (40 mg) and the resulting mixture was stirred at 85° C. for 3 h. Then the reaction mixture was diluted with ethyl acetate, filtered through Celite and washed with water and brine. The organic extract was dried over anhydrous sodium sulfate, concentrated and purified on a silica gel column using ethyl acetate and hexanes to yield the title compound (1.0 g, 89% yield). HRMS calcd for $C_{37}H_{44}O_{10}F_2S$ $[M+H]^+$ 719.2696, observed 719.2693.

Step 8: 4-(2-(2-Carboxy-ethyl)-3-{6-[3-(2,2-difluoro-benzo[1,3]dioxol-5-yl)-5-methanesulfonyl-phenoxy]-hexyl}-phenoxy)-butyric Acid

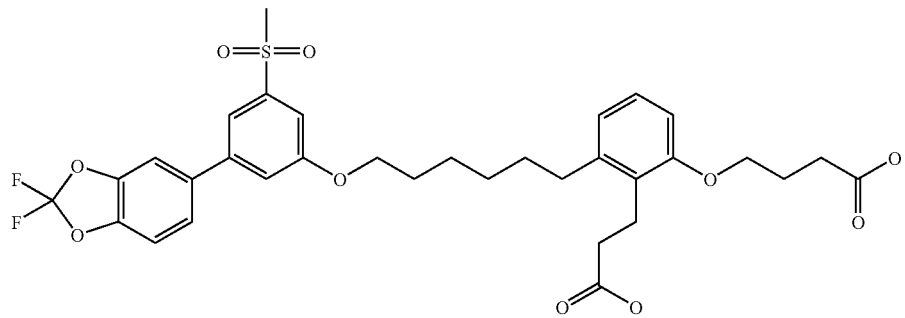

To a solution of 4-[3-{6-[3-(2,2-difluoro-benzo[1,3]dioxol-5-yl)-5-methanesulfonyl-phenoxy]-hexyl}-2-(2-ethoxycarbonyl-ethyl)-phenoxy]-butyric acid ethyl ester (1.0 g) in ethanol (8 mL) was added a solution of NaOH (556 mg) in water (4 mL) and the resulting mixture was stirred at room temperature for 3 h. Then the reaction mixture was diluted with water, acidified with 3 N HCl and extracted into ethyl acetate. The organic extract was washed with brine, dried over anhydrous sodium sulfate and concentrated under reduced pressure to give an oil which was crystallized from ethyl acetate/hexanes mixture to yield the title compound (0.8 g, 87% yield). HRMS calcd for $C_{33}H_{36}O_{10}F_2S$ [M+Na]$^+$ 685.1889, observed 685.1892.

Example 47

4-[3-[6-(3-Benzo[1,3]dioxol-5-yl-5-ethanesulfonyl-phenoxy)-hexyl]-2-(2-carboxy-ethyl)-phenoxy]-butyric Acid

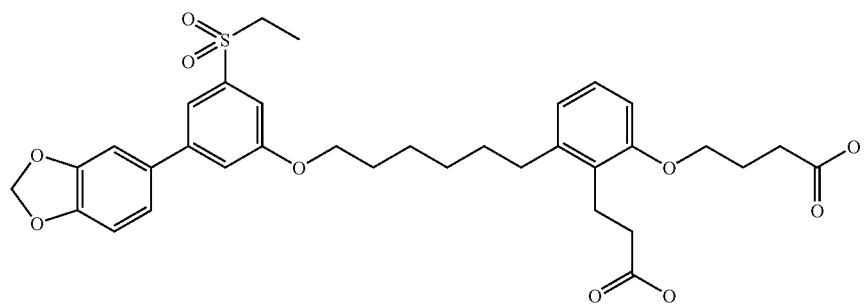

Step 1: Preparation of 1,3-dibromo-5-methoxy-benzene

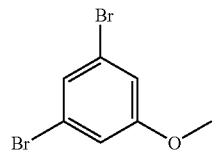

To a suspension of 3,5-dibromophenol (20 g, 79.39 mmol) and potassium carbonate (21.95 g, 158.78 mmol) in acetone (100 mL) was added iodomethane (24.79 g, 174.65 mmol) at room temperature. The resulting light yellow color mixture was heated to reflux and stirred for 15 h at which time TLC analysis of the mixture indicated the absence of starting material. Then, the reaction mixture was cooled to room temperature and diluted with water (200 mL) and ethyl acetate (200 mL). The two layers were separated and the aqueous layer was extracted with ethyl acetate (100 mL). The combined extracts were washed with brine solution (250 mL) and dried over anhydrous magnesium sulfate. Filtration of the drying agent and the concentration of the solution under reduced pressure gave the crude residue which was purified by using an ISCO 330 g column chromatography, eluting with 0-3% ethyl acetate in hexanes to obtain 1,3-dibromo-5-methoxy-benzene (20.47 g, 97%) as a white solid: EI(+)-HRMS m/e calcd for $C_7H_6Br_2O$ (M)$^+$ 263.8780, found 263.8785.

Step 2: Preparation of
1-bromo-3-ethylsulfanyl-5-methoxy-benzene

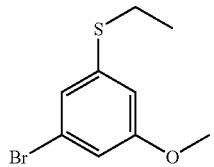

To a mixture 1,3-dibromo-5-methoxy-benzene (2.65 g, 10 mmol) and sodium thioethoxide (1.01 g, 12 mmol) was added dimethylformamide (30 mL) at room temperature. Then, the resulting light yellow solution was heated to 105° C. and stirred for 2 h at which time TLC analysis of the mixture indicated the absence of starting material. The reaction mixture was cooled to room temperature and diluted with water (50 mL) and brine solution (50 mL). Then, the organic compound was extracted into ethyl acetate (3×50 mL). The combined extracts were washed with brine solution (150 mL) and dried over anhydrous magnesium sulfate. Filtration of the drying agent and the concentration of the solution under reduced pressure gave the crude residue which was purified by using an ISCO 120 g column chromatography, eluting with 0-20% ethyl actetate in hexanes to obtain 1-bromo-3-ethylsulfanyl-5-methoxy-benzene (1.35 g, 55%) as a white solid: EI(+)-HRMS m/e calcd for $C_9H_{11}BrOS$ (M)$^+$ 245.9715, found 245.9713.

Step 3: Preparation of
1-bromo-3-ethanesulfonyl-5-methoxy-benzene

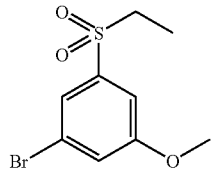

A similar procedure as described in Example 40, step 2 was used, starting from 1-bromo-3-ethylsulfanyl-5-methoxy-benzene (882 mg, 3.56 mmol) and m-chloroperbenzoic acid (2.0 g, 11.58 mmol) to afford 1-bromo-3-ethanesulfonyl-5-methoxy-benzene (685 mg, 69%) as a white solid: EI(+)-HRMS m/e calcd for $C_9H_{11}BrO_3S$ (M)$^+$ 277.9613, found 277.9612.

Step 4: Preparation of
3-bromo-5-ethanesulfonyl-phenol

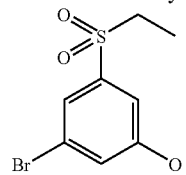

To a solution of 1-bromo-3-ethanesulfonyl-5-methoxy-benzene (670 mg, 2.4 mmol) in dichloromethane (25 mL) was added boron tribromide (4.8 mL, 4.8 mmol) in dichloromethane (1.0 M) at −70° C. Then, the resulting brown solution was stirred for 30 minutes at this temperature and then the cooling bath was removed to warm to room temperature and stirred for 15 h at which time TLC analysis of the mixture indicated the absence of starting material. The reaction mixture was quenched with water slowly (50 mL). The two layers were separated and the aqueous layer was extracted with dichloromethane (50 mL). The combined organic layer was washed with brine solution (100 mL) and the organic layer was dried over anhydrous magnesium sulfate, filtered, and concentrated in vacuo. The crude residue was purified by using an ISCO 40 g column, eluting with 0-50% ethyl acetate in hexanes to obtain 3-bromo-5-ethanesulfonyl-phenol (576 mg, 90.5%) as a colorless viscous oil: ES(+)-HRMS m/e calcd for $C_8H_9BrO_3S$ (M+H)$^+$ 264.9529, found 264.9528.

Step 5: Preparation of 4-[3-[6-(3-bromo-5-ethanesulfonyl-phenoxy)-hexyl]-2-(2-ethoxycarbonyl-ethyl)-phenoxy]-butyric Acid Ethyl Ester

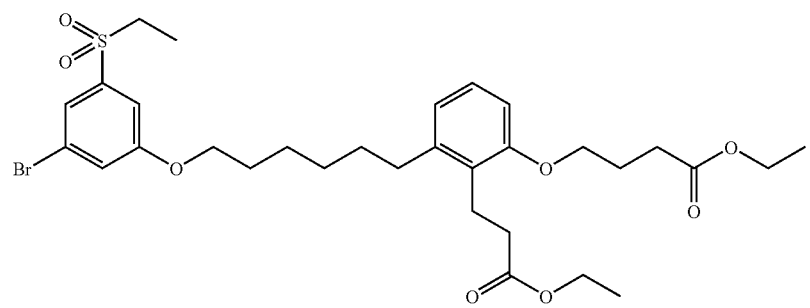

A similar procedure as described in Example 40, step 6 was used, starting from 4-[3-(6-bromo-hexyl)-2-(2-ethoxycarbonyl-ethyl)-phenoxy]-butyric acid ethyl ester (1.13 g, 2.39 mmol), 3-bromo-5-ethanesulfonyl-phenol (576 mg, 2.17 mmol), and potassium carbonate (600 mg, 4.34 mmol) to afford 4-[3-[6-(3-bromo-5-ethanesulfonyl-phenoxy)-hexyl]-2-(2-ethoxycarbonyl-ethyl)-phenoxy]-butyric acid ethyl ester (1.35 g, 95%) as a colorless viscous oil: ES(+)-HRMS m/e calcd for $C_{31}H_{43}BrO_8S$ (M+Na)$^+$ 677.1754, found 677.1756.

Step 6: Preparation of 4-[3-[6-(3-benzo[1,3]dioxol-5-yl-5-ethanesulfonyl-phenoxy)-hexyl]-2-(2-ethoxycarbonyl-ethyl)-phenoxy]-butyric Acid Ethyl Ester

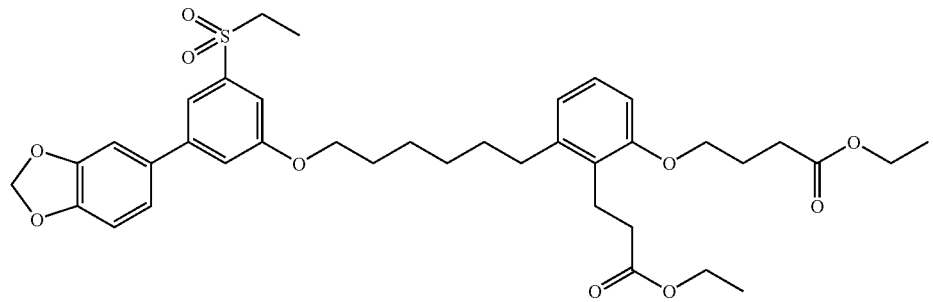

A similar procedure as described in Example 41, step 1 was used, starting from 4-[3-[6-(3-bromo-5-ethanesulfonyl-phenoxy)-hexyl]-2-(2-ethoxycarbonyl-ethyl)-phenoxy]-butyric acid ethyl ester (200 mg, 0.31 mmol), 3,4-(methylenedioxyphenyl)boronic acid (101 mg, 0.62 mmol), [1,1'-bis(diphenylphosphino)ferrocene]dichloropalladium(II) (37 mg, 0.05 mmol), and cesium carbonate (199 mg, 0.62 mmol) to afford 4-[3-[6-(3-benzo[1,3]dioxol-5-yl-5-ethanesulfonyl-phenoxy)-hexyl]-2-(2-ethoxycarbonyl-ethyl)-phenoxy]-butyric acid ethyl ester (212 mg, 99%) as a colorless viscous oil: ES(+)-HRMS m/e calcd for $C_{38}H_{48}O_{10}S$ (M+Na)$^+$ 719.2860, found 719.2865.

Step 7: Preparation of 4-[3-[6-(3-benzo[1,3]dioxol-5-yl-5-ethanesulfonyl-phenoxy)-hexyl]-2-(2-carboxy-ethyl)-phenoxy]-butyric Acid

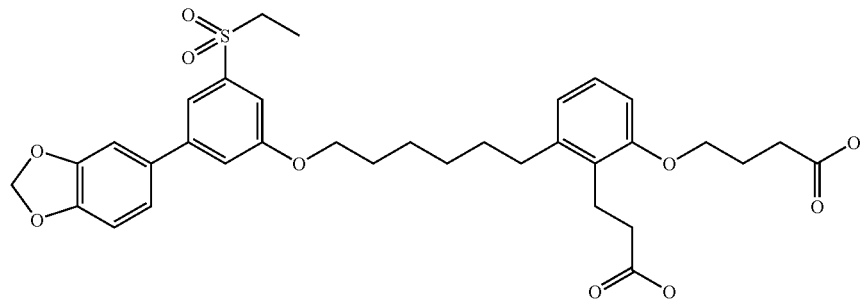

A similar procedure as described in Example 40, step 8 was used, starting from 4-[3-[6-(3-benzo[1,3]dioxol-5-yl-5-ethanesulfonyl-phenoxy)-hexyl]-2-(2-ethoxycarbonyl-ethyl)-phenoxy]-butyric acid ethyl ester (200 mg, 0.28 mmol) and 1.0 N aqueous sodium hydroxide (5 mL) to afford 4-[3-[6-(3-benzo[1,3]dioxol-5-yl-5-ethanesulfonyl-phenoxy)-hexyl]-2-(2-carboxy-ethyl)-phenoxy]-butyric acid (151 mg, 82%) as an amorphous white solid, mp=134-135° C.: ES(+)-HRMS m/e calcd for $C_{34}H_{40}O_{10}S$ (M+Na)$^+$ 663.2234, found 663.2235.

Example 48

4-[2-(2-Carboxy-ethyl)-3-[6-(5-ethanesulfonyl-3',4'-difluoro-biphenyl-3-yloxy)-hexyl]-phenoxy]-butyric Acid

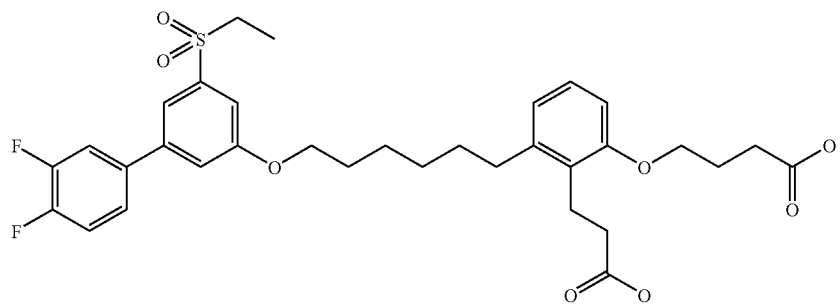

Step 1: Preparation of 4-[3-[6-(5-ethanesulfonyl-3',4'-difluoro-biphenyl-3-yloxy)-hexyl]-2-(2-ethoxycarbonyl-ethyl)-phenoxy]-butyric Acid Ethyl Ester

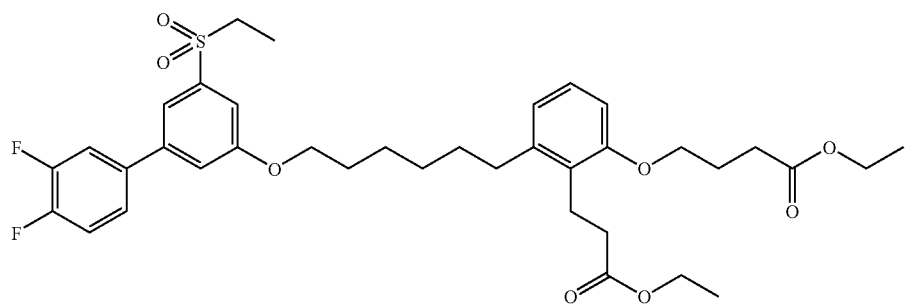

A similar procedure as described in Example 41, step 1 was used, starting from 4-[3-[6-(3-bromo-5-ethanesulfonyl-phenoxy)-hexyl]-2-(2-ethoxycarbonyl-ethyl)-phenoxy]-butyric acid ethyl ester (150 mg, 0.23 mmol), 3,4-difluorophenylboronic acid (72 mg, 0.46 mmol), [1,1'-bis(diphenylphosphino)ferrocene]dichloropalladium(II) (29 mg, 0.04 mmol), and cesium carbonate (149 mg, 0.46 mmol) to afford 4-[3-[6-(5-ethanesulfonyl-3',4'-difluoro-biphenyl-3-yloxy)-hexyl]-2-(2-ethoxycarbonyl-ethyl)-phenoxy]-butyric acid ethyl ester (148 mg, 94%) as a colorless viscous oil: ES(+)-HRMS m/e calcd for $C_{37}H_{46}F_2O_8S$ (M+Na)$^+$ 711.2773, found 711.2778.

Step 2: Preparation of 4-[2-(2-carboxy-ethyl)-3-[6-(5-ethanesulfonyl-3',4'-difluoro-biphenyl-3-yloxy)-hexyl]-phenoxy]-butyric Acid

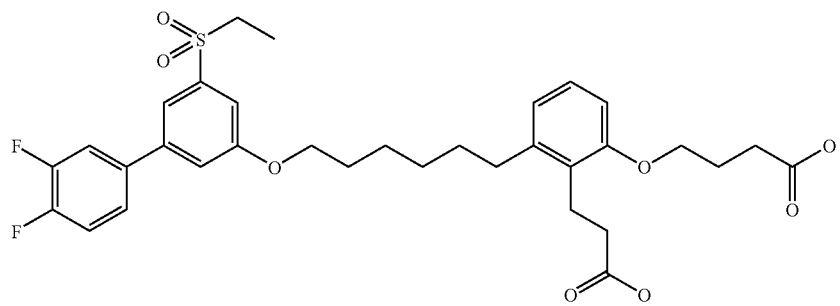

A similar procedure as described in Example 40, step 8 was used, starting from 4-[3-[6-(5-ethanesulfonyl-3',4'-difluoro-biphenyl-3-yloxy)-hexyl]-2-(2-ethoxycarbonyl-ethyl)-phenoxy]-butyric acid ethyl ester (137 mg, 0.198 mmol) and 1.0 N aqueous sodium hydroxide (5 mL) to afford 4-[2-(2-carboxy-ethyl)-3-[6-(5-ethanesulfonyl-3',4'-difluoro-biphenyl-3-yloxy)-hexyl]-phenoxy]-butyric acid (102 mg, 82%) as an amorphous white solid: ES(+)-HRMS m/e calcd for $C_{33}H_{38}F_2O_8S$ $(M+H)^+$ 633.2328, found 633.2327.

Example 49

4-[2-(2-Carboxy-ethyl)-3-[6-(5-ethanesulfonyl-4'-fluoro-3'-hydroxy-biphenyl-3-yloxy)-hexyl]-phenoxy]-butyric Acid

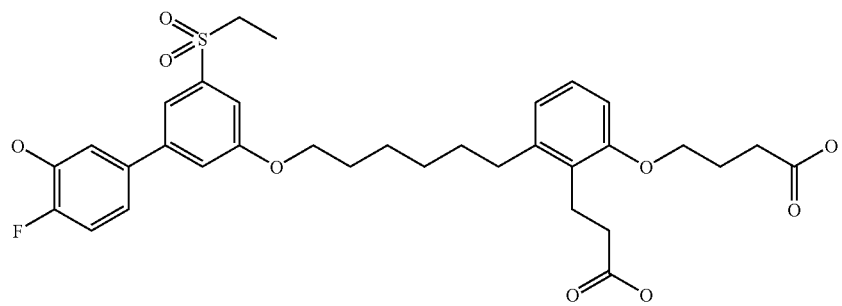

Step 1: Preparation of 4-[3-[6-(5-ethanesulfonyl-4'-fluoro-3'-hydroxy-biphenyl-3-yloxy)-hexyl]-2-(2-ethoxycarbonyl-ethyl)-phenoxy]-butyric Acid Ethyl Ester

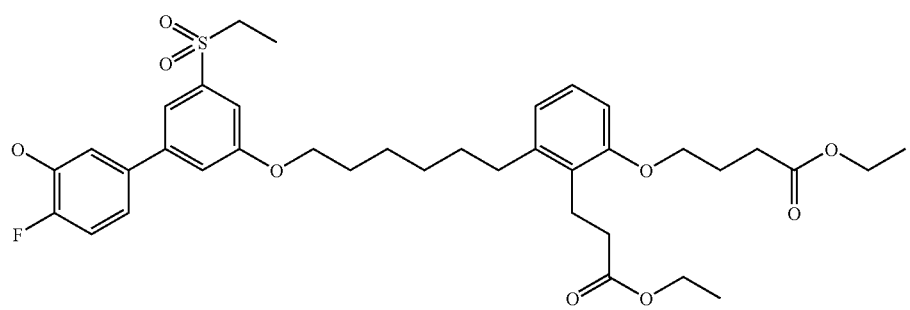

A similar procedure as described in Example 41, step 1 was used, starting from 4-[3-[6-(3-bromo-5-ethanesulfonyl-phenoxy)-hexyl]-2-(2-ethoxycarbonyl-ethyl)-phenoxy]-butyric acid ethyl ester (213 mg, 0.32 mmol), 4-fluoro-3-hydroxy-phenylboronic acid (101 mg, 0.64 mmol), [1,1'-bis(diphenylphosphino)ferrocene]dichloropalladium(II) (37 mg, 0.05 mmol), and cesium carbonate (317 mg, 0.97 mmol) to afford 4-[3-[6-(5-ethanesulfonyl-4'-fluoro-3'-hydroxy-biphenyl-3-yloxy)-hexyl]-2-(2-ethoxycarbonyl-ethyl)-phenoxy]-butyric acid ethyl ester (218 mg, 99%) as a colorless viscous oil: ES(+)-HRMS m/e calcd for $C_{37}H_{47}FO_9S$ $(M+Na)^+$ 709.2817, found 709.2817.

Step 2: Preparation of 4-[2-(2-carboxy-ethyl)-3-[6-(5-ethanesulfonyl-4'-fluoro-3'-hydroxy-biphenyl-3-yloxy)-hexyl]-phenoxy]-butyric Acid

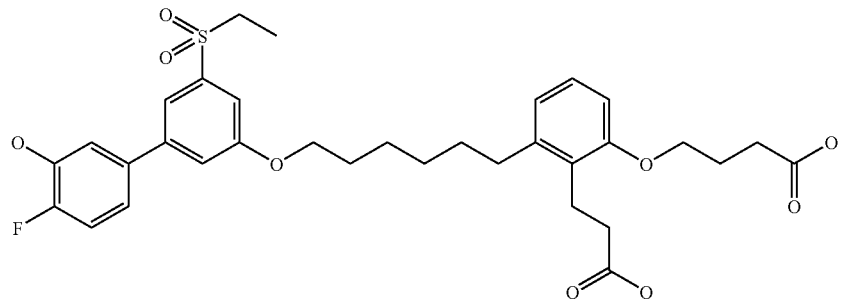

A similar procedure as described in Example 40, step 8 was used, starting from 4-[3-[6-(5-ethanesulfonyl-4'-fluoro-3'-hydroxy-biphenyl-3-yloxy)-hexyl]-2-(2-ethoxycarbonyl-ethyl)-phenoxy]-butyric acid ethyl ester (218 mg, 0.32 mmol) and 1.0 N aqueous sodium hydroxide (5 mL) to afford 4-[2-(2-carboxy-ethyl)-3-[6-(5-ethanesulfonyl-4'-fluoro-3'-hydroxy-biphenyl-3-yloxy)-hexyl]-phenoxy]-butyric acid (173 mg, 87%) as an amorphous white solid: ES(+)-HRMS m/e calcd for $C_{33}H_{39}FO_9S$ $(M+Na)^+$ 653.2191, found 653.2194.

Example 50

4-[2-(2-Carboxy-ethyl)-3-[6-(5-ethanesulfonyl-4'-chloro-biphenyl-3-yloxy)-hexyl]-phenoxy]-butyric Acid

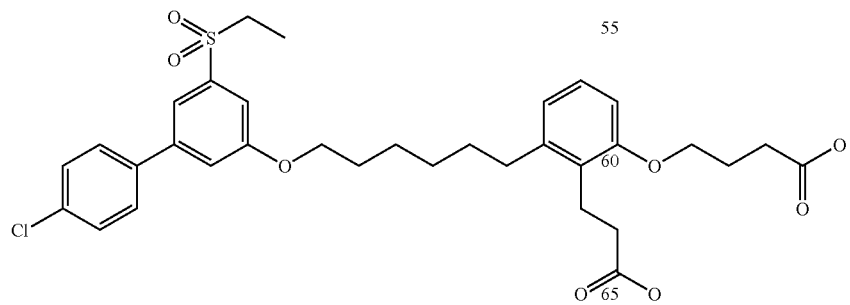

Step 1: Preparation of 4-[3-[6-(5-ethanesulfonyl-4'-chloro-biphenyl-3-yloxy)-hexyl]-2-(2-ethoxycarbonyl-ethyl)-phenoxy]-butyric Acid Ethyl Ester

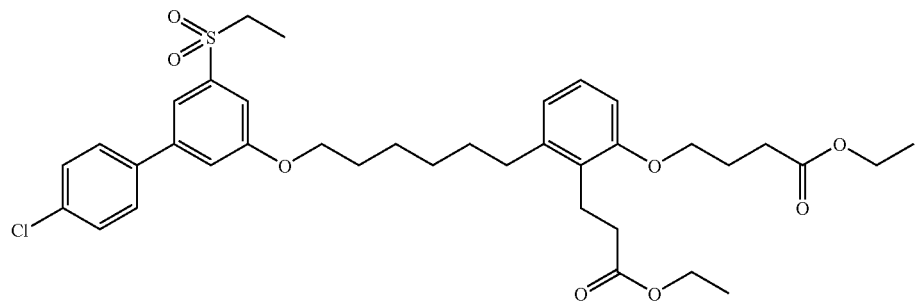

A similar procedure as described in Example 41, step 1 was used, starting from 4-[3-[6-(3-bromo-5-ethanesulfonyl-phenoxy)-hexyl]-2-(2-ethoxycarbonyl-ethyl)-phenoxy]-butyric acid ethyl ester (161 mg, 0.25 mmol), 4-chloro-phenylboronic acid (81 mg, 0.50 mmol), [1,1'-bis(diphenylphosphino)ferrocene]dichloropalladium(II) (27 mg, 0.038 mmol), and cesium carbonate (162 mg, 0.5 mmol) to afford 4-[3-[6-(5-ethanesulfonyl-4'-chloro-biphenyl-3-yloxy)-hexyl]-2-(2-ethoxycarbonyl-ethyl)-phenoxy]-butyric acid ethyl ester (130 mg, 77%) as a colorless viscous oil: ES(+)-HRMS m/e calcd for $C_{37}H_{47}ClO_8S$ (M+Na)$^+$ 709.2572, found 709.2572.

Step 2: Preparation of 4-[2-(2-carboxy-ethyl)-3-[6-(5-ethanesulfonyl-4'-chloro-biphenyl-3-yloxy)-hexyl]-phenoxy]-butyric Acid

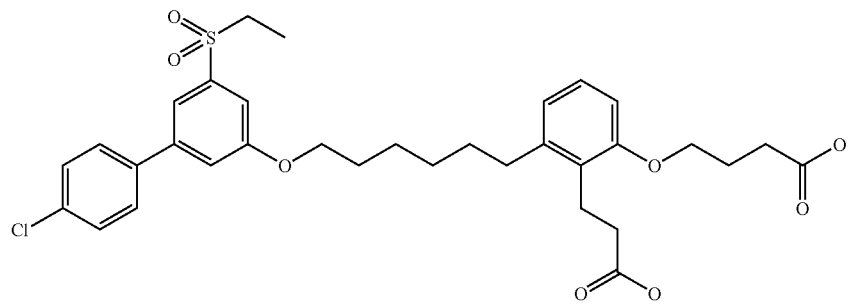

A similar procedure as described in Example 40, step 8 was used, starting from 4-[3-[6-(5-ethanesulfonyl-4'-chloro-biphenyl-3-yloxy)-hexyl]-2-(2-ethoxycarbonyl-ethyl)-phenoxy]-butyric acid ethyl ester (116 mg, 0.17 mmol) and 1.0 N aqueous sodium hydroxide (1.7 mL) to afford 4-[2-(2-carboxy-ethyl)-3-[6-(5-ethanesulfonyl-4'-chloro-biphenyl-3-yloxy)-hexyl]-phenoxy]-butyric acid (106 mg, 99%) as an amorphous white solid: ES(+)-HRMS m/e calcd for $C_{33}H_{39}ClO_8S$ (M+Na)$^+$ 653.1946, found 653.1948.

Example 51

4-[2-(2-Carboxy-ethyl)-3-[6-(5-ethanesulfonyl-4'-fluoro-biphenyl-3-yloxy)-hexyl]-phenoxy]-butyric Acid

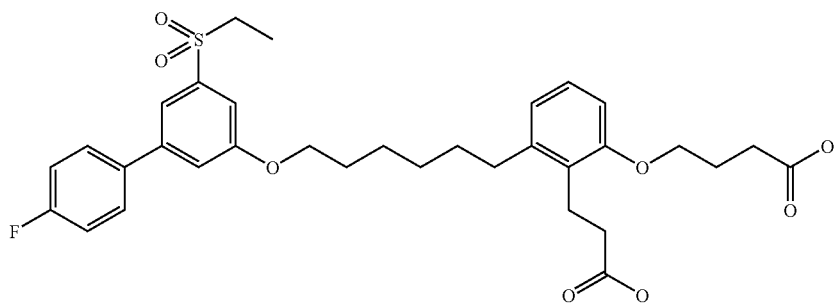

Step 1: Preparation of 4-[3-[6-(5-ethanesulfonyl-4'-fluoro-biphenyl-3-yloxy)-hexyl]-2-(2-ethoxycarbonyl-ethyl)-phenoxy]-butyric Acid Ethyl Ester

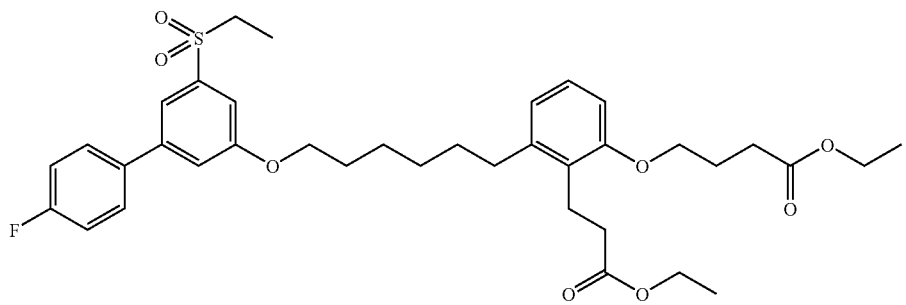

A similar procedure as described in Example 41, step 1 was used, starting from 4-[3-[6-(3-bromo-5-ethanesulfonyl-phenoxy)-hexyl]-2-(2-ethoxycarbonyl-ethyl)-phenoxy]-butyric acid ethyl ester (150 mg, 0.23 mmol), 4-fluoro-phenylboronic acid (65.4 mg, 0.46 mmol), [1,1'-bis(diphenylphosphino)ferrocene]dichloropalladium(II) (25 mg, 0.034 mmol), and cesium carbonate (151 mg, 0.46 mmol) to afford 4-[3-[6-(5-ethanesulfonyl-4'-fluoro-biphenyl-3-yloxy)-hexyl]-2-(2-ethoxycarbonyl-ethyl)-phenoxy]-butyric acid ethyl ester (123 mg, 80%) as a colorless viscous oil: ES(+)-HRMS m/e calcd for $C_{37}H_{47}FO_8S$ $(M+Na)^+$ 693.2868, found 693.2871.

Step 2: Preparation of 4-[2-(2-carboxy-ethyl)-3-[6-(5-ethanesulfonyl-4'-fluoro-biphenyl-3-yloxy)-hexyl]-phenoxy]-butyric Acid

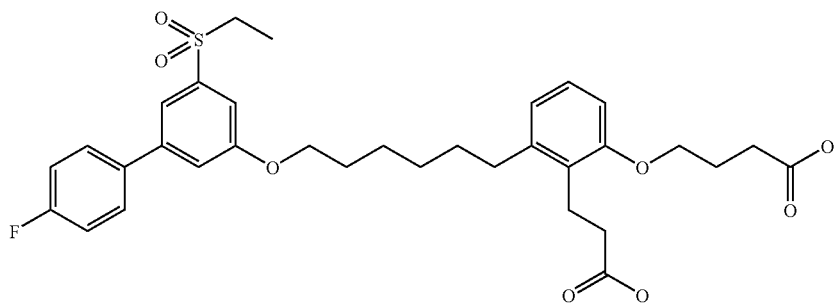

A similar procedure as described in Example 40, step 8 was used, starting from 4-[3-[6-(5-ethanesulfonyl-4'-fluoro-biphenyl-3-yloxy)-hexyl]-2-(2-ethoxycarbonyl-ethyl)-phenoxy]-butyric acid ethyl ester (115 mg, 0.17 mmol) and 1.0 N aqueous sodium hydroxide (1.7 mL) to afford 4-[2-(2-carboxy-ethyl)-3-[6-(5-ethanesulfonyl-4'-fluoro-biphenyl-3-yloxy)-hexyl]-phenoxy]-butyric acid (51 mg, 48%) as an amorphous white solid: ES(+)-HRMS m/e calcd for $C_{33}H_{39}FO_8S$ $(M+Na)^+$ 637.2242, found 637.2242.

Example 52

4-[2-(2-Carboxy-ethyl)-3-[6-(3-ethanesulfonyl-5-thiophen-3-yl-phenoxy)-hexyl]-phenoxy]-butyric Acid

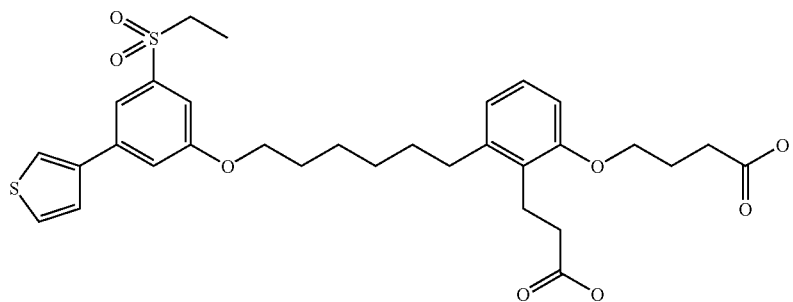

Step 1: Preparation of 4-[3-[6-(3-ethanesulfonyl-5-thiophen-3-yl-phenoxy)-hexyl]-2-(2-ethoxycarbonyl-ethyl)-phenoxy]-butyric Acid Ethyl Ester

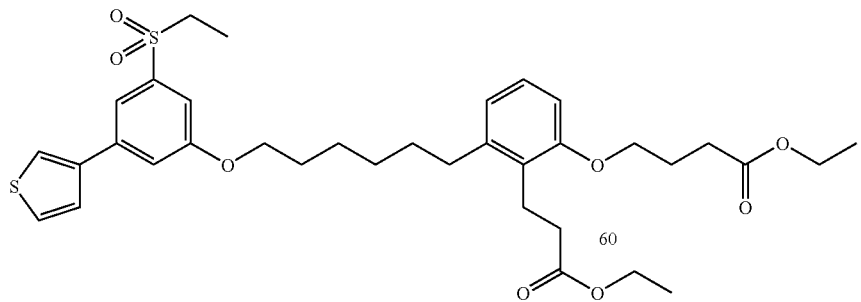

A similar procedure as described in Example 41, step 1 was used, starting from 4-[3-[6-(3-bromo-5-ethanesulfonyl-phenoxy)-hexyl]-2-(2-ethoxycarbonyl-ethyl)-phenoxy]-butyric acid ethyl ester (154 mg, 0.23 mmol), 3-thiopheneboronic acid (60.2 mg, 0.47 mmol), [1,1'-bis(diphenylphosphino)ferrocene]dichloropalladium(II) (26 mg, 0.035 mmol), and cesium carbonate (155 mg, 0.47 mmol) to afford 4-[3-[6-(3-ethanesulfonyl-5-thiophen-3-yl-phenoxy)-hexyl]-2-(2-ethoxycarbonyl-ethyl)-phenoxy]-butyric acid ethyl ester (117 mg, 76%) as a colorless viscous oil: ES(+)-HRMS m/e calcd for $C_{35}H_{46}O_8S_2$ (M+Na)$^+$ 681.2526, found 681.2526.

Step 2: Preparation of 4-[2-(2-carboxy-ethyl)-3-[6-(3-ethanesulfonyl-5-thiophen-3-yl-phenoxy)-hexyl]-phenoxy]-butyric Acid

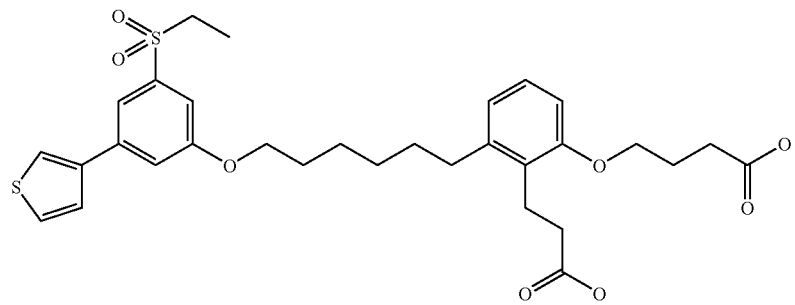

A similar procedure as described in Example 40, step 8 was used, starting from 4-[3-[6-(3-ethanesulfonyl-5-thiophen-3-yl-phenoxy)-hexyl]-2-(2-ethoxycarbonyl-ethyl)-phenoxy]-butyric acid ethyl ester (111 mg, 0.17 mmol) and 1.0 N aqueous sodium hydroxide (1.7 mL) to afford 4-[2-(2-carboxy-ethyl)-3-[6-(3-ethanesulfonyl-5-thiophen-3-yl-phenoxy)-hexyl]-phenoxy]-butyric acid (53 mg, 52%) as an amorphous white solid: ES(+)-HRMS m/e calcd for $C_{31}H_{38}O_8S_2$ (M+Na)$^+$ 625.1900, found 625.1904.

Example 53

4-[3-[6-[3-Benzo[1,3]dioxol-5-yl-5-(propane-1-sulfonyl)-phenoxy]-hexyl]-2-(2-carboxy-ethyl)-phenoxy]-butyric Acid

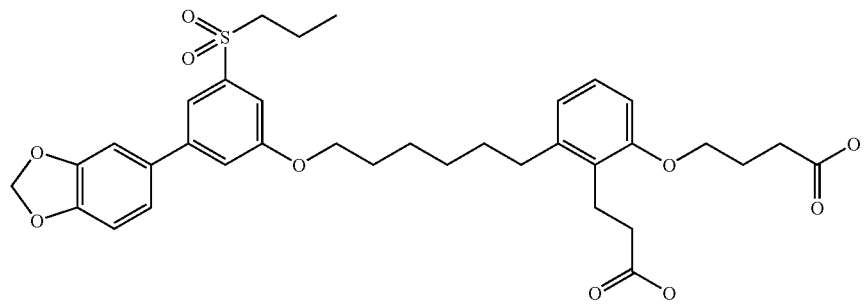

Step 1: Preparation of 1-bromo-3-methoxy-5-propylsulfanyl-benzene

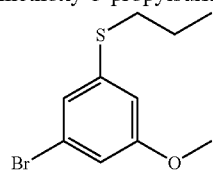

A similar procedure as described in Example 47, step 2 was used, starting from 3,5-dibromoanisole (5.3 g, 19.93 mmol) and sodium 1-propanethiolate (2.47 g, 23.92 mmol) to afford 1-bromo-3-methoxy-5-propylsulfanyl-benzene (2.01 g, 39%) as a light yellow oil: EI(+)-HRMS m/e calcd for $C_{10}H_{13}BrOS$ (M)$^+$ 259.9870, found 259.9870.

Step 2: Preparation of
1-bromo-3-methoxy-5-(propane-1-sulfonyl)-benzene

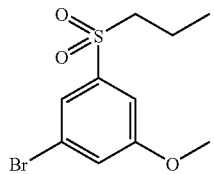

A similar procedure as described in Example 40, step 2 was used, starting from 1-bromo-3-methoxy-5-propylsulfanyl-benzene (1.99 g, 7.62 mmol) and m-chloroperbenzoic acid (4.6 g, 16 mmol) to afford 1-bromo-3-methoxy-5-(propane-1-sulfonyl)-benzene (1.56 g, 70%) as a white solid: ES(+)-HRMS m/e calcd for $C_{10}H_{13}BrO_3S$ (M+Na)$^+$ 314.9661, found 314.9660.

Step 3: Preparation of
3-bromo-5-(propane-1-sulfonyl)-phenol

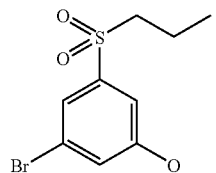

A similar procedure as described in Example 47, step 4 was used, starting from 1-bromo-3-methoxy-5-(propane-1-sulfonyl)-benzene (1.55 g, 5.29 mmol) and boron tribromide (10.57 mL, 10.57 mmol, 1.0M in dichloromethane) to afford 3-bromo-5-(propane-1-sulfonyl)-phenol (1.15 g, 78%) as a white solid: ES(+)-HRMS m/e calcd for $C_9H_{11}BrO_3S$ (M+Na)$^+$ 300.9504, found 300.9503.

Step 4: Preparation of 4-[3-{6-[3-bromo-5-(propane-1-sulfonyl)-phenoxy]-hexyl}-2-(2-ethoxycarbonyl-ethyl)-phenoxy]-butyric Acid Ethyl Ester

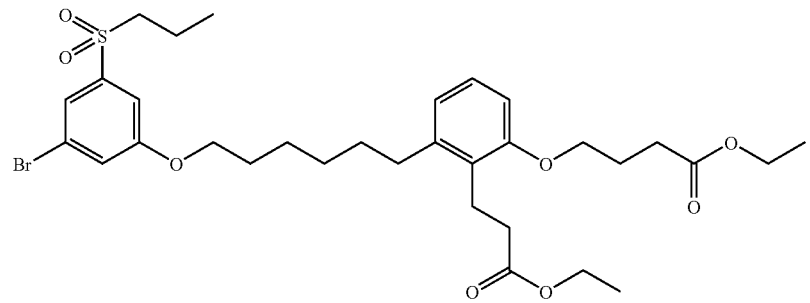

A similar procedure as described in Example 40, step 6 was used, starting from 4-[3-(6-bromo-hexyl)-2-(2-ethoxycarbonyl-ethyl)-phenoxy]-butyric acid ethyl ester (2.14 g, 4.53 mmol), 3-bromo-5-(propane-1-sulfonyl)-phenol (1.15 g, 4.12 mmol), and potassium carbonate (1.14 g, 8.24 mmol) to afford 4-[3-{6-[3-bromo-5-(propane-1-sulfonyl)-phenoxy]-hexyl}-2-(2-ethoxycarbonyl-ethyl)-phenoxy]-butyric acid ethyl ester (2.67 g, 97%) as a colorless viscous oil: ES(+)-HRMS m/e calcd for $C_{32}H_{45}BrO_8S$ (M+Na)$^+$ 691.1911, found 691.1905.

Step 5: Preparation of 4-[3-{6-[3-benzo[1,3]dioxol-5-yl-5-(propane-1-sulfonyl)-phenoxy]-hexyl}-2-(2-ethoxycarbonyl-ethyl)-phenoxy]-butyric Acid Ethyl Ester

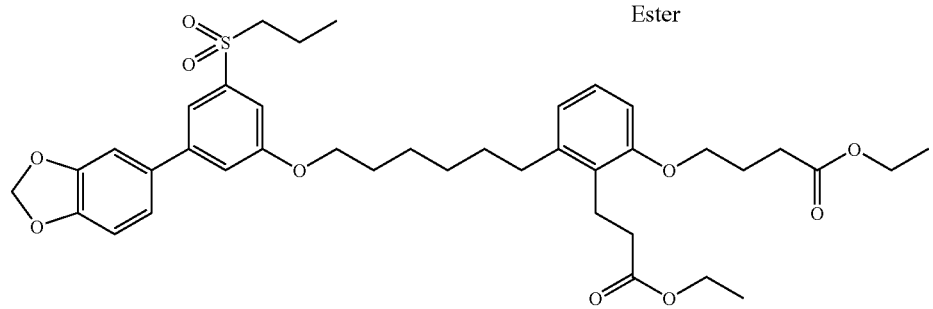

A similar procedure as described in Example 41, step 1 was used, starting from 4-[3-{6-[3-bromo-5-(propane-1-sulfony)-phenoxy]-hexyl}-2-(2-ethoxycarbonyl-ethyl)-phenoxy]-butyric acid ethyl ester (208 mg, 0.31 mmol), 3,4-(methylenedioxyphenyl)boronic acid (103 mg, 0.62 mmol), [1,1'-bis(diphenylphosphino)ferrocene]dichloropalladium (II) (34 mg, 0.046 mmol), and cesium carbonate (205 mg, 0.62 mmol) to afford 4-[3-{6-[3-benzo[1,3]dioxol-5-yl-5-(propane-1-sulfonyl)-phenoxy]-hexyl}-2-(2-ethoxycarbonyl-ethyl)-phenoxy]-butyric acid ethyl ester (95 mg, 43%) as a colorless viscous oil: ES(+)-HRMS m/e calcd for $C_{39}H_{50}O_{10}S$ (M+Na)$^+$ 733.3017, found 733.3011.

Step 6: Preparation of 4-[3-{6-[3-benzo[1,3]dioxol-5-yl-5-(propane-1-sulfonyl)-phenoxy]-hexyl}-2-(2-carboxy-ethyl)-phenoxy]-butyric Acid

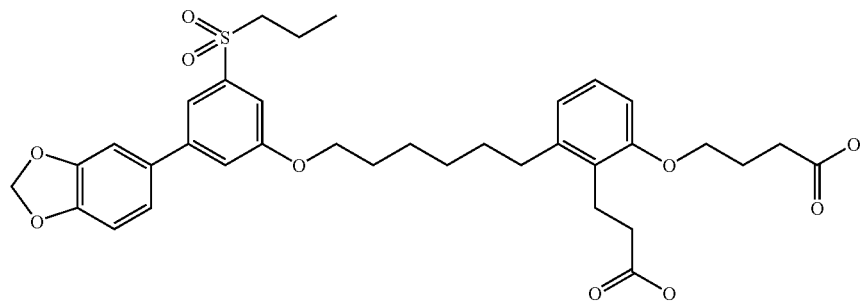

A similar procedure as described in Example 40, step 8 was used, starting from 4-[3-{6-[3-benzo[1,3]dioxol-5-yl-5-(propane-1-sulfonyl)-phenoxy]-hexyl}-2-(2-ethoxycarbonyl-ethyl)-phenoxy]-butyric acid ethyl ester (87 mg, 0.12 mmol) and 1.0 N aqueous sodium hydroxide (1.22 mL) to afford 4-[3-{6-[3-benzo[1,3]dioxol-5-yl-5-(propane-1-sulfonyl)-phenoxy]-hexyl}-2-(2-carboxy-ethyl)-phenoxy]-butyric acid (46 mg, 57%) as an amorphous white solid: ES(+)-HRMS m/e calcd for $C_{35}H_{42}O_{10}S$ (M+Na)$^+$ 677.2391, found 677.2388.

Example 54

4-[2-(2-Carboxy-ethyl)-3-[6-(5-(propane-1-sulfonyl)-4'-chloro-biphenyl-3-yloxy)-hexyl]-phenoxy]-butyric Acid

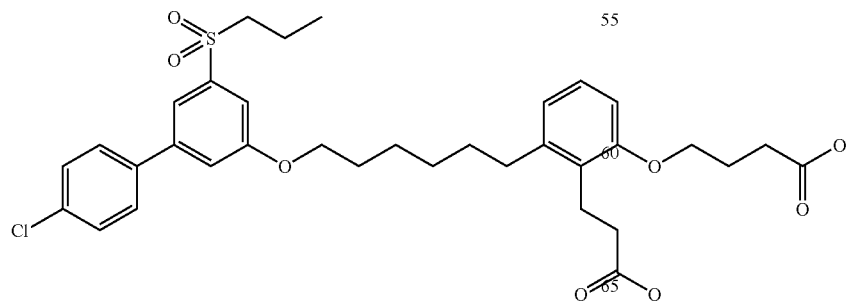

Step 1: Preparation of 4-[2-(2-ethoxycarbonyl-ethyl)-3-[6-(5-(propane-1-sulfonyl)-4'-chloro-biphenyl-3-yloxy)-hexyl]-phenoxy]-butyric Acid Ethyl Ester

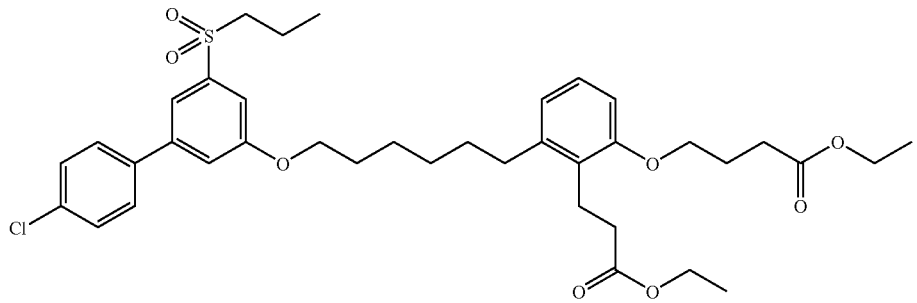

A similar procedure as described in Example 41, step 1 was used, starting from 4-[3-[6-(3-bromo-5-(propane-1-sulfonyl)-phenoxy)-hexyl]-2-(2-ethoxycarbonyl-ethyl)-phenoxy]-butyric acid ethyl ester (220 mg, 0.33 mmol), 4-chlorophenylboronic acid (108 mg, 0.66 mmol), [1,1'-bis(diphenylphosphino)ferrocene]dichloropalladium(II) (36 mg, 0.049 mmol), and cesium carbonate (217 mg, 0.66 mmol) to afford 4-[2-(2-ethoxycarbonyl-ethyl)-3-[6-(5-(propane-1-sulfonyl)-4'-chloro-biphenyl-3-yloxy)-hexyl]-phenoxy]-butyric acid ethyl ester (209 mg, 91%) as a colorless viscous oil: ES(+)-HRMS m/e calcd for $C_{38}H_{49}ClO_8S$ $(M+Na)^+$ 723.2729, found 723.2729.

Step 2: Preparation of 4-[2-(2-carboxy-ethyl)-3-[6-(5-(propane-1-sulfonyl)-4'-chloro-biphenyl-3-yloxy)-hexyl]-phenoxy]-butyric Acid

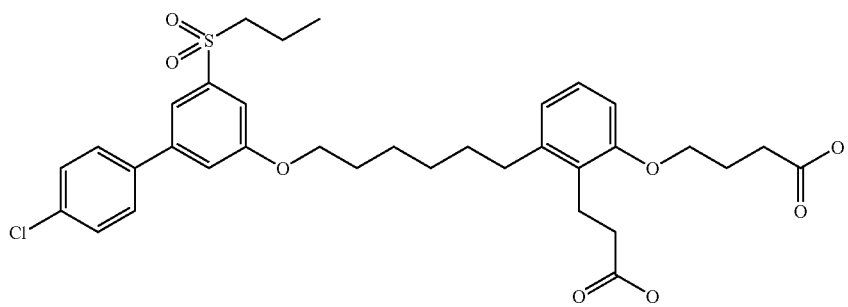

A similar procedure as described in Example 40, step 8 was used, starting from 4-[2-(2-ethoxycarbonyl-ethyl)-3-[6-(5-(propane-1-sulfonyl)-4'-chloro-biphenyl-3-yloxy)-hexyl]-phenoxy]-butyric acid ethyl ester (196 mg, 0.28 mmol) and 1.0 N aqueous sodium hydroxide (2.8 mL) to afford 4-[2-(2-carboxy-ethyl)-3-[6-(5-(propane-1-sulfonyl)-4'-chloro-biphenyl-3-yloxy)-hexyl]-phenoxy]-butyric acid (165 mg, 92%) as an amorphous white solid: ES(+)-HRMS m/e calcd for $C_{34}H_{41}ClO_8S$ $(M+Na)^+$ 667.2103, found 667.2102.

Example 55

4-[2-(2-Carboxy-ethyl)-3-[6-(5-(propane-1-sulfonyl)-4'-fluoro-biphenyl-3-yloxy)-hexyl]-phenoxy]-butyric Acid

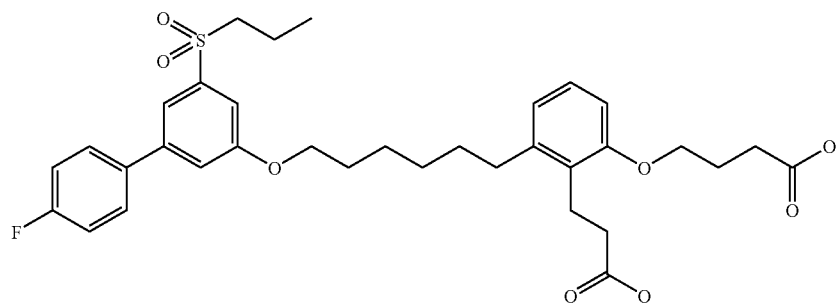

Step 1: Preparation of 4-[2-(2-ethoxycarbonyl-ethyl)-3-[6-(5-(propane-1-sulfonyl)-4'-fluoro-biphenyl-3-yloxy)-hexyl]-phenoxy]-butyric Acid Ethyl Ester

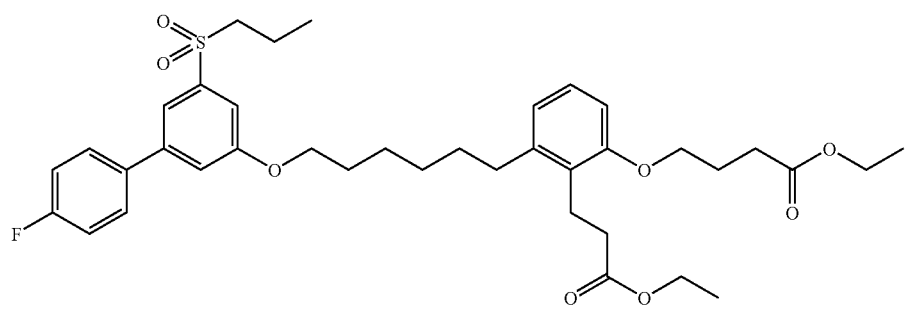

A similar procedure as described in Example 41, step 1 was used, starting from 4-[3-[6-(3-bromo-5-(propane-1-sulfonyl)-phenoxy)-hexyl]-2-(2-ethoxycarbonyl-ethyl)-phenoxy]-butyric acid ethyl ester (220 mg, 0.33 mmol), 4-fluorophenylboronic acid (92.1 mg, 0.66 mmol), [1,1'-bis(diphenylphosphino)ferrocene]dichloropalladium(II) (36 mg, 0.05 mmol), and cesium carbonate (217 mg, 0.66 mmol) to afford 4-[2-(2-ethoxycarbonyl-ethyl)-3-[6-(5-(propane-1-sulfonyl)-4'-fluoro-biphenyl-3-yloxy)-hexyl]-phenoxy]-butyric acid ethyl ester (208 mg, 92%) as a colorless viscous oil: ES(+)-HRMS m/e calcd for $C_{38}H_{49}FO_8S$ (M+Na)$^+$ 707.3024, found 707.3023.

Step 2: Preparation of 4-[2-(2-carboxy-ethyl)-3-[6-(5-(propane-1-sulfonyl)-4'-fluoro-biphenyl-3-yloxy)-hexyl]-phenoxy]-butyric Acid

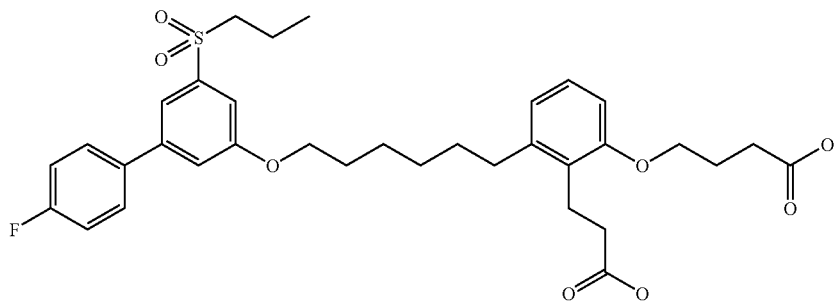

A similar procedure as described in Example 40, step 8 was used, starting from 4-[2-(2-ethoxycarbonyl-ethyl)-3-[6-(5-(propane-1-sulfonyl)-4'-fluoro-biphenyl-3-yloxy)-hexyl]-phenoxy]-butyric acid ethyl ester (195 mg, 0.29 mmol) and 1.0 N aqueous sodium hydroxide (2.9 mL) to afford 4-[2-(2-carboxy-ethyl)-3-[6-(5-(propane-1-sulfonyl)-4'-fluoro-biphenyl-3-yloxy)-hexyl]-phenoxy]-butyric acid (156 mg, 87%) as an amorphous white solid: ES(+)-HRMS m/e calcd for $C_{34}H_{41}FO_8S$ $(M+Na)^+$ 651.2398, found 651.2398.

Example 56

4-[2-(2-Carboxy-ethyl)-3-[6-(5-(propane-1-sulfonyl)-3',4'-difluoro-biphenyl-3-yloxy)-hexyl]-phenoxy]-butyric Acid

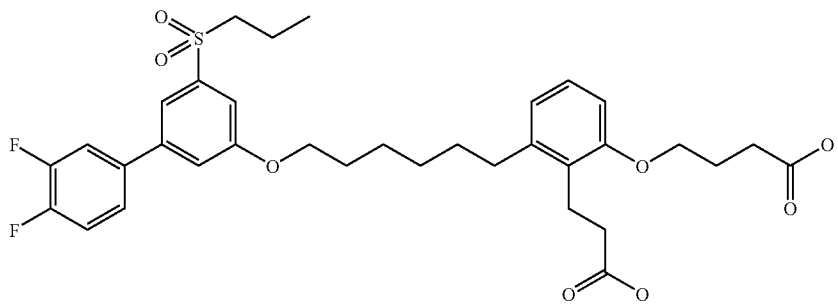

Step 1: Preparation of 4-[2-(2-ethoxycarbonyl-ethyl)-3-[6-(5-(propane-1-sulfonyl)-3',4'-difluoro-biphenyl-3-yloxy)-hexyl]-phenoxy]-butyric Acid Ethyl Ester

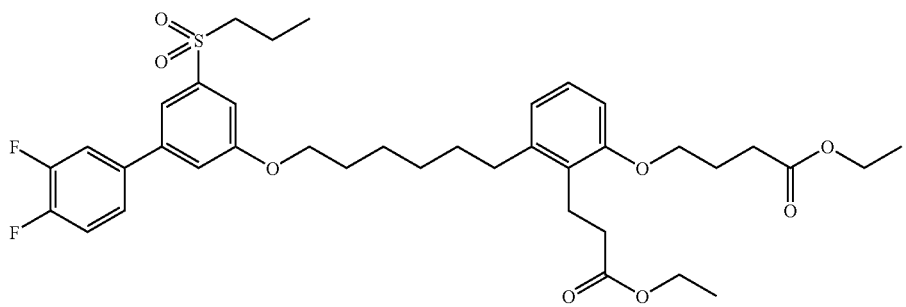

A similar procedure as described in Example 41, step 1 was used, starting from 4-[3-[6-(3-bromo-5-(propane-1-sulfonyl)-phenoxy)-hexyl]-2-(2-ethoxycarbonyl-ethyl)-phenoxy]-butyric acid ethyl ester (220 mg, 0.33 mmol), 3,4-difluoro-phenylboronic acid (107 mg, 0.66 mmol), [1,1'-bis(diphenylphosphino)ferrocene]dichloropalladium(II) (36 mg, 0.05 mmol), and cesium carbonate (217 mg, 0.66 mmol) to afford 4-[2-(2-ethoxycarbonyl-ethyl)-3-[6-(5-(propane-1-sulfonyl)-3',4'-difluoro-biphenyl-3-yloxy)-hexyl]-phenoxy]-butyric acid ethyl ester (142 mg, 62%) as a colorless viscous oil: ES(+)-HRMS m/e calcd for $C_{38}H_{48}F_2O_8S$ $(M+Na)^+$ 725.2930, found 725.2928.

Step 2: Preparation of 4-[2-(2-carboxy-ethyl)-3-[6-(5-(propane-1-sulfonyl)-3',4'-difluoro-biphenyl-3-yloxy)-hexyl]-phenoxy]-butyric Acid

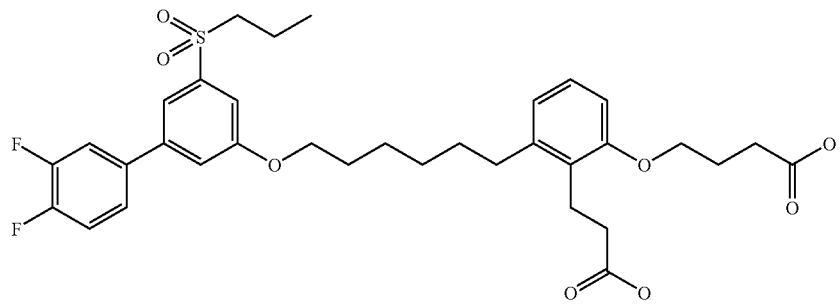

A similar procedure as described in Example 40, step 8 was used, starting from 4-[2-(2-ethoxycarbonyl-ethyl)-3-[6-(5-(propane-1-sulfonyl)-3',4'-difluoro-biphenyl-3-yloxy)-hexyl]-phenoxy]-butyric acid ethyl ester (130 mg, 0.19 mmol) and 1.0 N aqueous sodium hydroxide (1.9 mL) to afford 4-[2-(2-carboxy-ethyl)-3-[6-(5-(propane-1-sulfonyl)-3',4'-difluoro-biphenyl-3-yloxy)-hexyl]-phenoxy]-butyric acid (55 mg, 46%) as an amorphous white solid: ES(+)-HRMS m/e calcd for $C_{34}H_{40}F_2O_8S$ $(M+Na)^+$ 669.2304, found 669.2299.

Example 57

4-[2-(2-Carboxy-ethyl)-3-[6-(3-(propane-1-sulfonyl)-5-thiophen-3-yl-phenoxy)-hexyl]-phenoxy]-butyric Acid

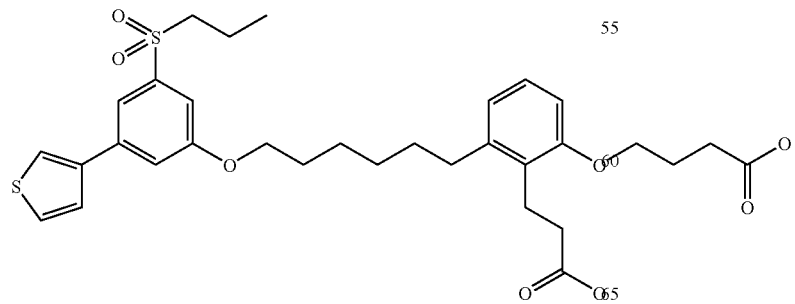

Step 1: Preparation of 4-[2-(2-ethoxycarbonyl-ethyl)-3-[6-(3-(propane-1-sulfonyl)-5-thiophen-3-yl-phenoxy)-hexyl]-phenoxy]-butyric Acid Ethyl Ester

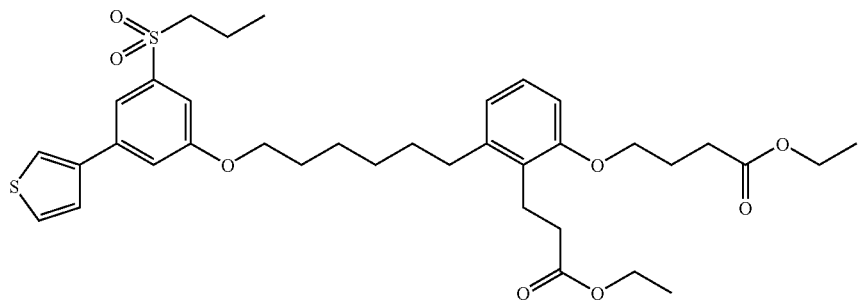

A similar procedure as described in Example 41, step 1 was used, starting from 4-[2-(2-ethoxycarbonyl-ethyl)-3-[6-(3-bromo-5-(propane-1-sulfonyl)-phenoxy)-hexyl]-phenoxy]-butyric acid ethyl ester (208 mg, 0.31 mmol), 3-thiopheneboronic acid (81.2 mg, 0.62 mmol), [1,1'-bis(diphenylphosphino)ferrocene]dichloropalladium(II) (34 mg, 0.047 mmol), and cesium carbonate (205 mg, 0.62 mmol) to afford 4-[2-(2-ethoxycarbonyl-ethyl)-3-[6-(3-(propane-1-sulfonyl)-5-thiophen-3-yl-phenoxy)-hexyl]-phenoxy]-butyric acid ethyl ester (152 mg, 73%) as a colorless viscous oil: ES(+)-HRMS m/e calcd for $C_{36}H_{48}O_8S_2$ (M+Na)$^+$ 695.2683, found 695.2680.

Step 2: Preparation of 4-[2-(2-carboxy-ethyl)-3-[6-(3-(propane-1-sulfonyl)-5-thiophen-3-yl-phenoxy)-hexyl]-phenoxy]-butyric Acid

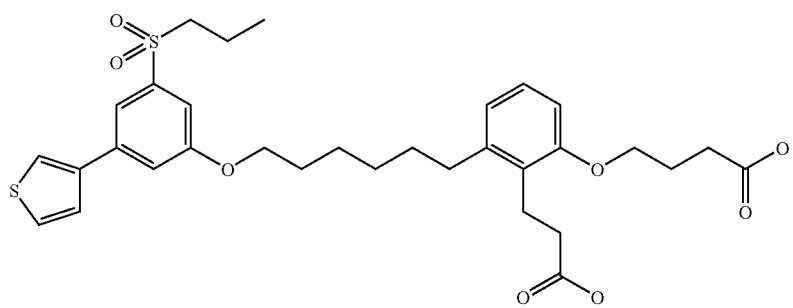

A similar procedure as described in Example 40, step 8 was used, starting from 4-[2-(2-ethoxycarbonyl-ethyl)-3-[6-(3-(propane-1-sulfonyl)-5-thiophen-3-yl-phenoxy)-hexyl]-phenoxy]-butyric acid ethyl ester (144 mg, 0.21 mmol) and 1.0 N aqueous sodium hydroxide (2.1 mL) to afford 4-[2-(2-carboxy-ethyl)-3-[6-(3-(propane-1-sulfonyl)-5-thiophen-3-yl-phenoxy)-hexyl]-phenoxy]-butyric acid (120 mg, 91%) as an amorphous white solid: ES(+)-HRMS m/e calcd for $C_{32}H_{40}O_8S_2$ (M+Na)$^+$ 639.2057, found 639.2056.

Example 58

4-[3-[6-(3-Benzo[1,3]dioxol-5-yl-5-(propane-2-sulfonyl)-phenoxy)-hexyl]-2-(2-carboxy-ethyl)-phenoxy]-butyric Acid

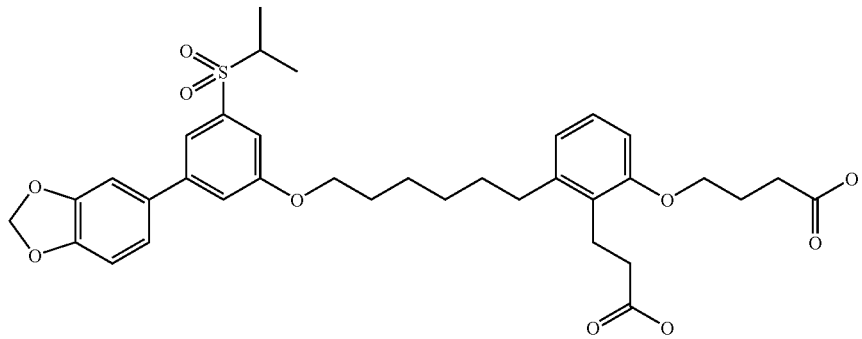

Step 1: Preparation of 1,3-dibromo-5-methoxymethoxy-benzene

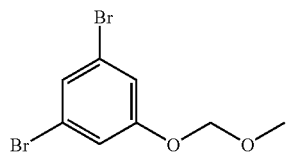

To a suspension of sodium hydride (693 mg, 17.33 mmol, 60%, oil was washed with pentane) in THF (15 mL) was added 3, 5-dibromophenol (3.0 g, 11.55 mmol) at 0° C. and the suspension was stirred for 30 minutes. Then, methoxymethyl chloride (1.4 g, 17.33 mmol) was added at 0° C. The resulting suspension was allowed to warm to room temperature and stirred for 2 days at which time TLC analysis of the mixture indicated the absence of starting material. Then, the reaction mixture was poured into an ice-water (50 mL) and the organic compound was extracted into ethyl acetate (2×100 mL). The combined extracts were washed with brine solution (250 mL) and dried over anhydrous magnesium sulfate. Filtration of the drying agent and the concentration of the solution under reduced pressure gave the crude residue which was purified by using an ISCO 120 g column chromatography, eluting with 5-20% ethyl acetate in hexanes to obtain 1,3-dibromo-5-methoxymethoxy-benzene (2.94 g, 86%) as a white solid: EI(+)-HRMS m/e calcd for $C_8H_8Br_2O_2$ (M)$^+$ 293.8891, found 293.8893.

Step 2: Preparation of 1-bromo-3-iso-propylsulfanyl-5-methoxymethoxy-benzene

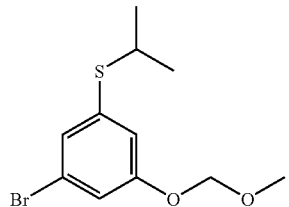

To a solution of 1,3-dibromo-5-methoxymethoxy-benzene (1.43 g, 4.8 mmol) in pentane (28.6 mL) was added n-butyllithium (9.66 mL, 24.16 mmol) at −20° C. and the reaction mixture was stirred for 1 h at this temperature. Then, the iso-propyl disulfide (3.78 g, 24.16 mmol) was added at this temperature and the resulting paste kind of suspension was allowed to warm slowly to 0° C. and stirred for 4 h. The reaction mixture was poured into a saturated ammonium chloride solution (25 mL) and the organic compound was extracted into diethyl ether (2×50 mL). The combined extracts were washed with brine solution (150 mL) and dried over anhydrous magnesium sulfate. Filtration of the drying agent and the concentration of the solution under reduced pressure gave the crude residue which was purified by using an ISCO 80 g column chromatography, eluting with 2-10% ethyl acetate in hexanes to obtain 1-bromo-3-iso-propylsulfanyl-5-methoxymethoxy-benzene (1.4 g, 99%) as a viscous oil: EI(+)-HRMS m/e calcd for $C_{11}H_{15}BrO_2S$ (M)$^+$ 289.9975, found 289.9975.

Step 3: Preparation of 1-bromo-3-methoxymethoxy-5-(propane-2-sulfonyl)-benzene

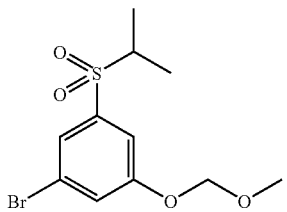

A similar procedure as described in Example 40, step 2 was used, starting from 1-bromo-3-iso-propylsulfanyl-5-methoxymethoxy-benzene (1.4 g, 4.88 mmol) and m-chloroperbenzoic acid (8.29 g, 28.85 mmol) to afford 1-bromo-3-methoxymethoxy-5-(propane-2-sulfonyl)-benzene (840 mg, 54%) as a viscous oil: ES(+)-HRMS m/e calcd for $C_{11}H_{15}BrO_4S$ (M+Na)$^+$ 344.9766, found 344.9765.

Step 4: Preparation of 3-bromo-5-(propane-2-sulfonyl)-phenol

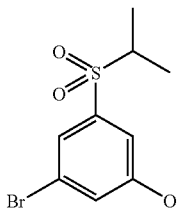

To a solution of 1-bromo-3-methoxymethoxy-5-(propane-2-sulfonyl)-benzene (840 mg, 2.59 mmol) in THF (24.4 mL) and methanol (40 mL) was added p-toluenesulfonic acid hydrate (150 mg, 0.78 mmol) at room temperature. Then, the resulting solution was heated to 70° C. and stirred for 2 days. Then, the reaction mixture was cooled to room temperature and the solvent was removed under reduced pressure. The crude residue which was purified by using an ISCO 40 g column chromatography, eluting with 5-30% ethyl acetate in hexanes to isolate 3-bromo-5-(propane-2-sulfonyl)-phenol (354 mg, 49%) as a viscous oil: ES(+)-HRMS m/e calcd for $C_9H_{11}BrO_3S$ (M+Na)$^+$ 300.9504, found 300.9505.

Step 5: Preparation of 4-[3-{6-[3-bromo-5-(propane-2-sulfonyl)-phenoxy]-hexyl}-2-(2-ethoxycarbonyl-ethyl)-phenoxy]-butyric Acid Ethyl Ester

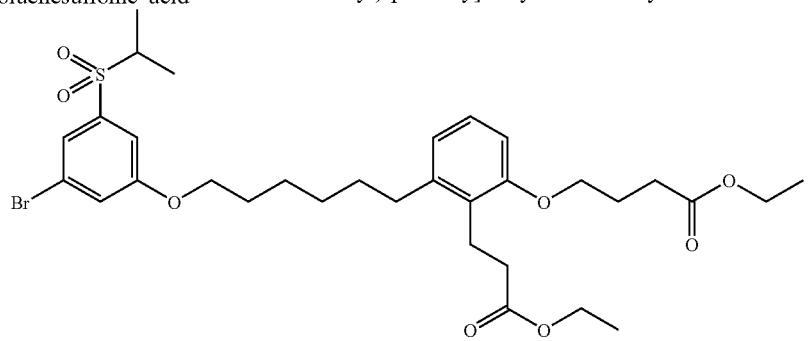

A similar procedure as described in Example 40, step 6 was used, starting from 4-[3-(6-bromo-hexyl)-2-(2-ethoxycarbonyl-ethyl)-phenoxy]-butyric acid ethyl ester (632 mg, 1.34 mmol), 3-bromo-5-(propane-2-sulfonyl)-phenol (340 mg, 1.22 mmol), and potassium carbonate (337 mg, 2.44 mmol) to afford 4-[3-{6-[3-bromo-5-(propane-2-sulfonyl)-phenoxy]-hexyl}-2-(2-ethoxycarbonyl-ethyl)-phenoxy]-butyric acid ethyl ester (567 mg, 70%) as a colorless viscous oil: ES(+)-HRMS m/e calcd for $C_{32}H_{45}BrO_8S$ (M+Na)$^+$ 691.1911, found 691.1908.

Step 6: Preparation of 4-[3-{6-[3-benzo[1,3]dioxol-5-yl-5-(propane-2-sulfonyl)-phenoxy]-hexyl}-2-(2-ethoxycarbonyl-ethyl)-phenoxy]-butyric Acid Ethyl Ester

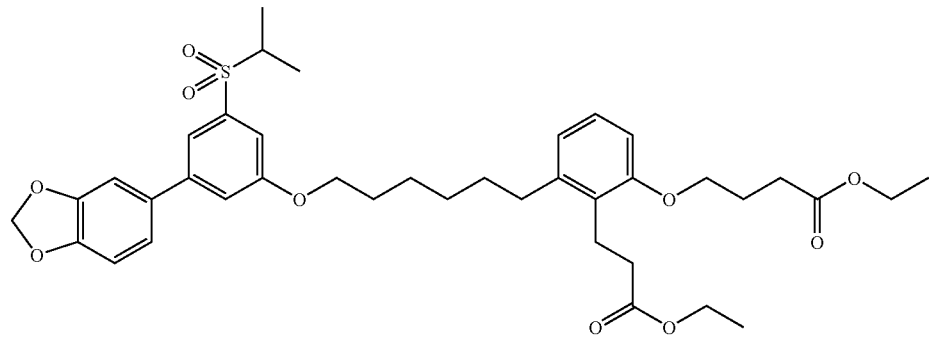

A similar procedure as described in Example 41, step 1 was used, starting from 4-[3-{6-[3-bromo-5-(propane-2-sulfony)-phenoxy]-hexyl}-2-(2-ethoxycarbonyl-ethyl)-phenoxy]-butyric acid ethyl ester (175 mg, 0.26 mmol), 3,4-(methylenedioxyphenyl)boronic acid (86.6 mg, 0.52 mmol), [1,1'-bis(diphenylphosphino)ferrocene]dichloropalladium (II) (28.7 mg, 0.039 mmol), and cesium carbonate (171.8 mg, 0.52 mmol) to afford 4-[3-{6-[3-benzo[1,3]dioxol-5-yl-5-(propane-2-sulfonyl)-phenoxy]-hexyl}-2-(2-ethoxycarbonyl-ethyl)-phenoxy]-butyric acid ethyl ester (147 mg, 79%) as a colorless viscous oil: ES(+)-HRMS m/e calcd for $C_{39}H_{50}O_{10}S$ (M+Na)$^+$ 733.3017, found 733.3017.

Step 7: Preparation of 4-[3-[6-(3-benzo[1,3]dioxol-5-yl-5-(propane-2-sulfonyl)-phenoxy)-hexyl]-2-(2-carboxy-ethyl)-phenoxy]-butyric Acid

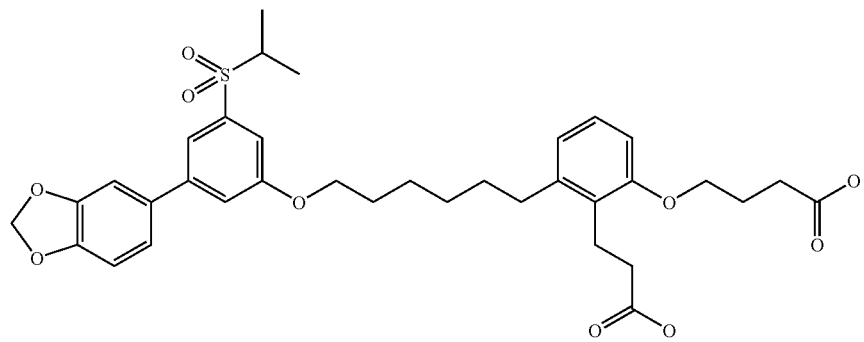

A similar procedure as described in Example 40, step 8 was used, starting from 4-[3-{6-[3-benzo[1,3]dioxol-5-yl-5-(propane-2-sulfonyl)-phenoxy]-hexyl}-2-(2-ethoxycarbonyl-ethyl)-phenoxy]-butyric acid ethyl ester (135 mg, 0.19 mmol) and 1.0 N aqueous sodium hydroxide (1.9 mL) to afford 4-[3-[6-(3-benzo[1,3]dioxol-5-yl-5-(propane-2-sulfonyl)-phenoxy)-hexyl]-2-(2-carboxy-ethyl)-phenoxy]-butyric acid (43 mg, 34%) as a white sticky solid: ES(+)-HRMS m/e calcd for $C_{35}H_{42}O_{10}S$ (M+Na)$^+$ 677.2391, found 677.2386.

Example 59

4-[2-(2-Carboxy-ethyl)-3-[6-(5-(propane-2-sulfonyl)-4'-chlorobiphenyl-3-yloxy)-hexyl]-phenoxy]-butyric Acid

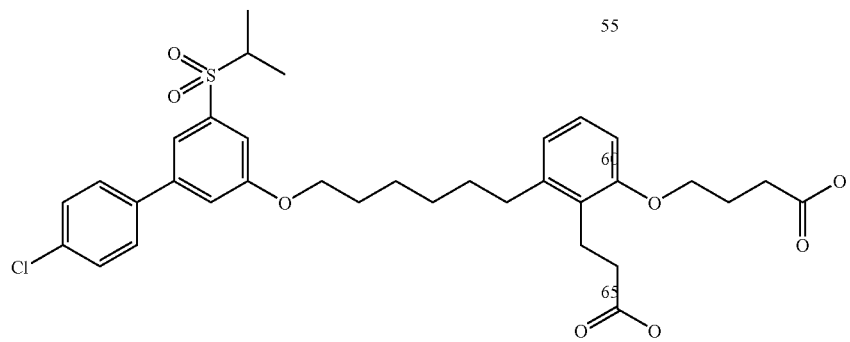

Step 1: Preparation of 4-[2-(2-ethoxycarbonyl-ethyl)-3-[6-(5-(propane-2-sulfonyl)-4'-chloro-biphenyl-3-yloxy)-hexyl]-phenoxy]-butyric Acid Ethyl Ester

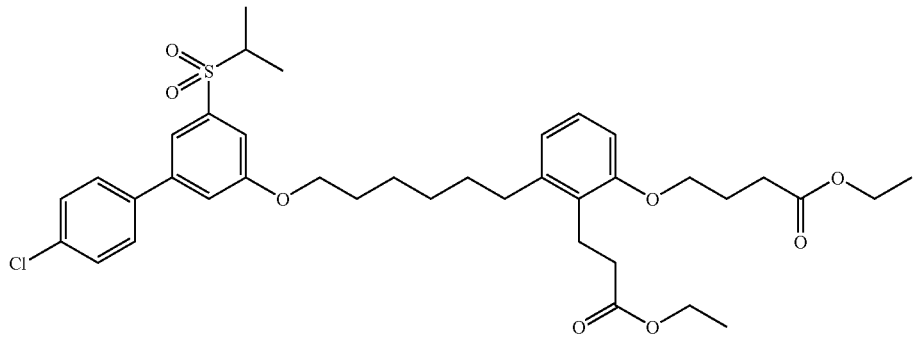

A similar procedure as described in Example 41, step 1 was used, starting from 4-[3-[6-(3-bromo-5-(propane-2-sulfonyl)-phenoxy)-hexyl]-2-(2-ethoxycarbonyl-ethyl)-phenoxy]-butyric acid ethyl ester (175 mg, 0.26 mmol), 4-chlorophenylboronic acid (86 mg, 0.52 mmol), [1,1'-bis(diphenylphosphino)ferrocene]dichloropalladium(II) (29 mg, 0.039 mmol), and cesium carbonate (172 mg, 0.52 mmol) to afford 4-[2-(2-ethoxycarbonyl-ethyl)-3-[6-(5-(propane-2-sulfonyl)-4'-chloro-biphenyl-3-yloxy)-hexyl]-phenoxy]-butyric acid ethyl ester (144 mg, 79%) as a colorless viscous oil: ES(+)-HRMS m/e calcd for $C_{38}H_{49}ClO_8S$ $(M+Na)^+$ 723.2729, found 723.2731.

Step 2: Preparation of 4-[2-(2-carboxy-ethyl)-3-[6-(5-(propane-2-sulfonyl)-4'-chloro-biphenyl-3-yloxy)-hexyl]-phenoxy]-butyric Acid

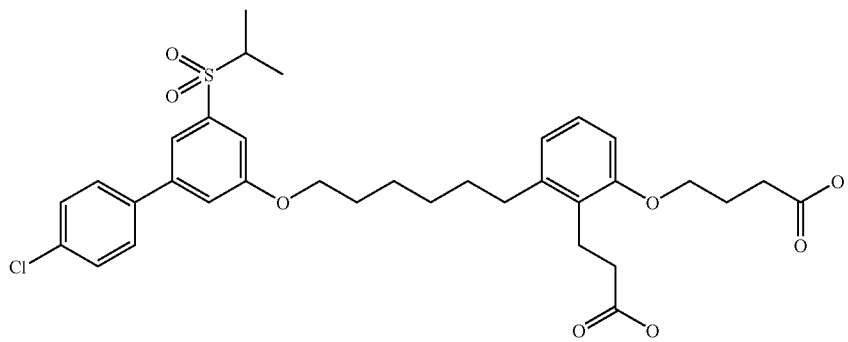

A similar procedure as described in Example 40, step 8 was used, starting from 4-[2-(2-ethoxycarbonyl-ethyl)-3-[6-(5-(propane-2-sulfonyl)-4'-chloro-biphenyl-3-yloxy)-hexyl]-phenoxy]-butyric acid ethyl ester (132 mg, 0.18 mmol) and 1.0 N aqueous sodium hydroxide (1.8 mL) to afford 4-[2-(2-carboxy-ethyl)-3-[6-(5-(propane-2-sulfonyl)-4'-chloro-biphenyl-3-yloxy)-hexyl]-phenoxy]-butyric acid (57 mg, 47%) as an amorphous white solid: ES(+)-HRMS m/e calcd for $C_{34}H_{41}ClO_8S$ $(M+Na)^+$ 667.2103, found 667.2101.

Example 60

4-[2-(2-Carboxy-ethyl)-3-[6-(5-(propane-2-sulfonyl)-4'-fluoro-biphenyl-3-yloxy)-hexyl]-phenoxy]-butyric Acid

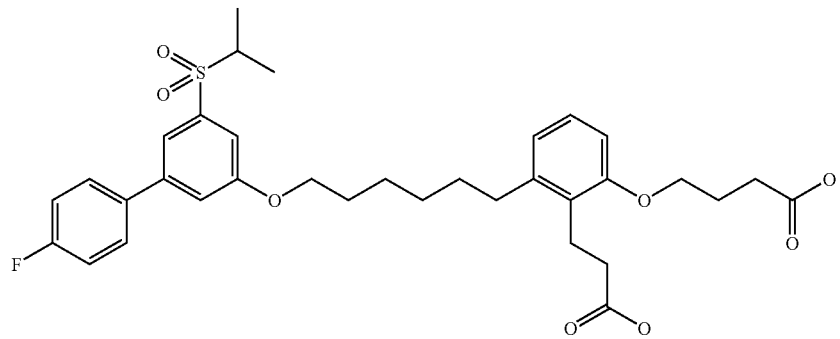

Step 1: Preparation of 4-[2-(2-ethoxycarbonyl-ethyl)-3-[6-(5-(propane-2-sulfonyl)-4'-fluoro-biphenyl-3-yloxy)-hexyl]-phenoxy]-butyric Acid Ethyl Ester

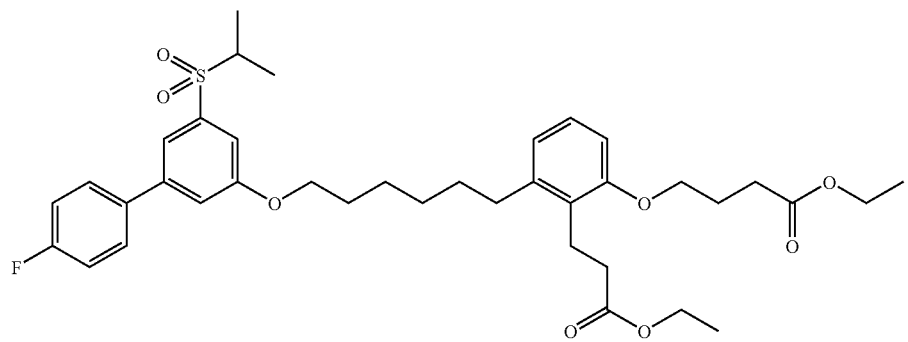

A similar procedure as described in Example 41, step 1 was used, starting from 4-[3-[6-(3-bromo-5-(propane-2-sulfonyl)-phenoxy)-hexyl]-2-(2-ethoxycarbonyl-ethyl)-phenoxy]-butyric acid ethyl ester (175 mg, 0.26 mmol), 4-fluorophenylboronic acid (73 mg, 0.52 mmol), [1,1'-bis(diphenylphosphino)ferrocene]dichloropalladium(II) (29 mg, 0.039 mmol), and cesium carbonate (172 mg, 0.52 mmol) to afford 4-[2-(2-ethoxycarbonyl-ethyl)-3-[6-(5-(propane-2-sulfonyl)-4'-fluoro-biphenyl-3-yloxy)-hexyl]-phenoxy]-butyric acid ethyl ester (180 mg, 99%) as a colorless viscous oil: ES(+)-HRMS m/e calcd for $C_{38}H_{49}FO_8S$ $(M+Na)^+$ 707.3024, found 707.3020.

Step 2: Preparation of 4-[2-(2-carboxy-ethyl)-3-[6-(5-(propane-2-sulfonyl)-4'-fluoro-biphenyl-3-yloxy)-hexyl]-phenoxy]-butyric Acid

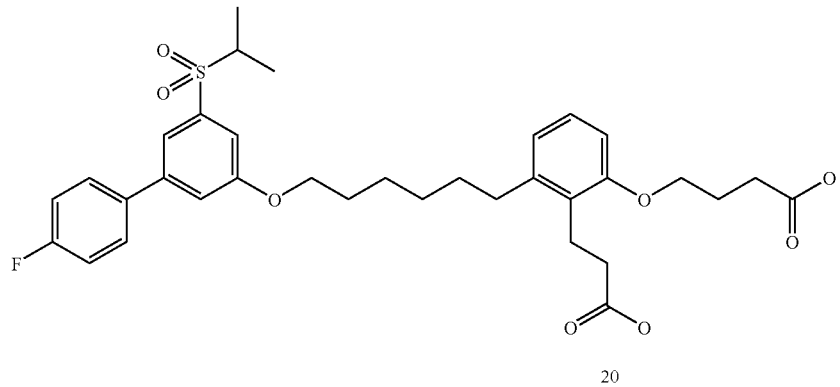

A similar procedure as described in Example 40, step 8 was used, starting from 4-[2-(2-ethoxycarbonyl-ethyl)-3-[6-(5-(propane-2-sulfonyl)-4'-fluoro-biphenyl-3-yloxy)-hexyl]-phenoxy]-butyric acid ethyl ester (180 mg, 0.26 mmol) and 1.0 N aqueous sodium hydroxide (2.6 mL) to afford 4-[2-(2-carboxy-ethyl)-3-[6-(5-(propane-2-sulfonyl)-4'-fluoro-biphenyl-3-yloxy)-hexyl]-phenoxy]-butyric acid (79 mg, 48%) as an amorphous white solid: ES(+)-HRMS m/e calcd for $C_{34}H_{41}FO_8S$ (M+Na)$^+$ 651.2398, found 651.2395.

Example 61

Assay of Compounds for Inhibition of LTB$_4$ Activity $Ca^{2+}$ Flux Assay for LTB4 Antagonist Assay
Cell Culture Conditions:

Human leukemia HL-60 cells endogenously expressing BLT1 and BLT2 receptors were cultured in RPMI-1640 medium supplemented with 20% fetal bovine serum, 2 mM glutamine, 100 U/mL penicillin and 100 ug/mL streptomycin.

Seventy two hours prior to experiment cells are counted using ViaCount reagent, centrifuged and resuspended at 2.0× 10$^5$ cells/mL density with the complete growth media containing 1 µM Retinoic Acid (Sigma).
Dye Loading and Assay:

On a day of the experiment loading buffer (Calcium-3 Assay Kit, Molecular Devices) was prepared by dissolving the contents of one vial (Express Kit) into 500 mL Hank's Balanced Salt Solution containing 20 mM HEPES and 5 mM probenecid. Equal volume of the loading buffer was mixed with the replacement buffer (Hank's Balanced Salt Solution containing 20 mM HEPES, 0.05% BSA and 5 mM probenecid). Retinoic Acid induced HL-60 cells were counted using ViaCount reagent, centrifuged and resuspended at 2.0×10$^6$ cells/mL density with the loading buffer/replacement buffer, dispensed into 384 well black/clear microplates (Falcon)(25 µL/well) and placed in a 37° C./5% CO$_2$ incubator for 1 hour.

During the incubation, test compounds were prepared at 6× the desired concentration in HBSS/20 mM HEPES/0.05% BSA as well as LTB4 (Biomol) was prepared at 2.2× concentration in HBSS/20 mM HEPES/0.5% BSA buffer.

After the incubation, both the cell and compound plates were brought to the FLIPR and 5 µL of the diluted compounds were transferred to the cell plates by the FLIPR. Plates were then incubated for 30 min at room temperature. After the ½ hour incubation, plates were returned to the FLIPR and 25 µL of 2.2×LTB4 was added to the cell plates. During the assay, fluorescence readings were taken simultaneously from all 384 wells of the cell plate every 1.5 seconds. Five readings were taken to establish a stable baseline, then 25 µL (LTB4) of sample was rapidly and simultaneously added to each well of the cell plate. The fluorescence was continuously monitored before, during and after sample addition for a total elapsed time of 100 seconds. Responses (increase in peak fluorescence) in each well following agonist addition was determined. The initial fluorescence reading from each well, prior to ligand stimulation, was used a zero baseline value for the data from that well. The responses are expressed as % inhibition of the neutral control (neural control: wells that received buffer plus DMSO but no test compound).

Assay Results

| Example # | Compound name | LTB4 antagonism (HL-60 FLIPR) |
|---|---|---|
| 5 | 4-{2-(2-Carboxy-ethyl)-3-[6-(4'-hydroxy-5-methanesulfonyl-biphenyl-3-yloxy)-hexyl]-phenoxy}-butyric acid | IC50 = 1.22 nM |
| 8 | 4-{2-(2-Carboxy-ethyl)-3-[6-(4'-fluoro-5-methanesulfonyl-biphenyl-3-yloxy)-hexyl]-phenoxy}-butyric acid | IC50 = 0.38 nM |
| 11 | 4-{2-(2-Carboxy-ethyl)-3-[6-(3'-fluoro-5-methanesulfonyl-4'-methyl-biphenyl-3-yloxy)-hexyl]-phenoxy}-butyric acid | IC50 = 0.32 nM |
| 12 | 4-{2-(2-Carboxy-ethyl)-3-[6-(3-methanesulfonyl-5-thiophen-3-yl-phenoxy)-hexyl]-phenoxy}-butyric acid | IC50 = 0.44 nM |
| 13 | 4-{2-(2-Carboxy-ethyl)-3-[6-(4'-ethyl-5-methanesulfonyl-biphenyl-3-yloxy)-hexyl]-phenoxy}-butyric acid | IC50 = 0.91 nM |
| 21 | 4-{2-(2-Carboxy-ethyl)-3-[6-(3-methanesulfonyl-5-thiazol-4-yl-phenoxy)-hexyl]-phenoxy}-butyric acid | IC50 = 261.43 nM |
| 23 | 4-(2-(2-Carboxy-ethyl)-3-{6-[3-(4-chloro-phenoxy)-5-methanesulfonyl-phenoxy]-hexyl}-phenoxy)-butyric acid | IC50 = 361.06 nM |
| 26 | 4-{2-(2-Carboxy-ethyl)-3-[6-(3-methanesulfonyl-5-phenylamino-phenoxy)-hexyl]-phenoxy}-butyric acid | IC50 = 47.11 nM |
| 27 | 4-{2-(2-Carboxy-ethyl)-3-[6-(3'-fluoro-5-methanesulfonyl-biphenyl-3-yloxy)-hexyl]-phenoxy}-butyric acid | IC50 = 0.9 nM |

-continued

| Example # | Compound name | LTB4 antagonism (HL-60 FLIPR) |
|---|---|---|
| 28 | 4-{2-(2-Carboxy-ethyl)-3-[6-(5-methanesulfonyl-biphenyl-3-yloxy)-hexyl]-phenoxy}-butyric acid | IC50 = 0.38 nM |
| 29 | 4-{2-(2-Carboxy-ethyl)-3-[6-(5-methanesulfonyl-4'-methoxy-biphenyl-3-yloxy)-hexyl]-phenoxy}-butyric acid | IC50 = 0.12 nM |
| 40 | 4-[3-[6-(3-Benzo[1,3]dioxol-5-yl-5-methanesulfonyl-phenoxy)-hexyl]-2-(2-carboxy-ethyl)-phenoxy]-butyric acid | IC50 = 0.09 nM |
| 41 | 4-(2-(2-Carboxy-ethyl)-3-{6-[3-(2,3-dihydro-benzo[1,4]dioxin-6-yl)-5-methanesulfonyl-phenoxy]-hexyl}-phenoxy)-butyric acid | C50 = 0.47 nM |
| 45 | 4-[3-[6-(3-Benzothiazol-5-yl-5-methanesulfonyl-phenoxy)-hexyl]-2-(2-carboxy-ethyl)-phenoxy]-butyric acid | IC50 = 0.2 nM |
| 46 | 4-(2-(2-Carboxy-ethyl)-3-{6-[3-(2,2-difluoro-benzo[1,3]dioxol-5-yl)-5-methanesulfonyl-phenoxy]-hexyl}-phenoxy)-butyric acid | IC50 = 0.24 nM |
| 47 | 4-[3-[6-(3-Benzo[1,3]dioxol-5-yl-5-ethanesulfonyl-phenoxy)-hexyl]-2-(2-carboxy-ethyl)-phenoxy]-butyric acid | IC50 = 0.27 nM |
| 51 | 4-{2-(2-Carboxy-ethyl)-3-[6-(5-ethanesulfonyl-4'-fluoro-biphenyl-3-yloxy)-hexyl]-phenoxy}-butyric acid | IC50 = 2.8 nM |
| 52 | 4-{2-(2-Carboxy-ethyl)-3-[6-(3-ethanesulfonyl-5-thiophen-3-yl-phenoxy)-hexyl]-phenoxy}-butyric acid | IC50 = 1.04 nM |
| 55 | 4-(2-(2-Carboxy-ethyl)-3-{6-[4'-fluoro-5-(propane-1-sulfonyl)-biphenyl-3-yloxy]-hexyl}-phenoxy)-butyric acid | IC50 = 63.8 nM |
| 60 | 4-(2-(2-Carboxy-ethyl)-3-{6-[4'-fluoro-5-(propane-2-sulfonyl)-biphenyl-3-yloxy]-hexyl}-phenoxy)-butyric acid | IC50 = 15.28 nM |

It is to be understood that the invention is not limited to the particular embodiments of the invention described above, as variations of the particular embodiments may be made and still fall within the scope of the appended claims.

What is claimed is:

1. A compound of formula (I):

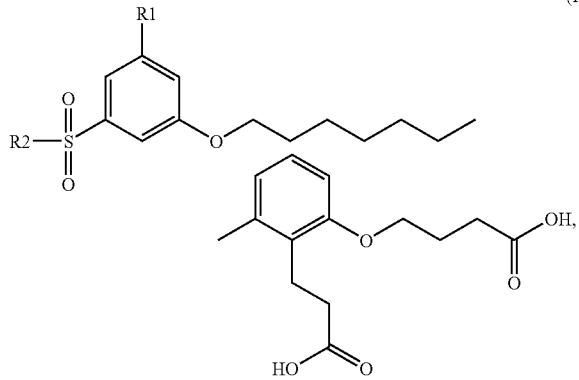

(I)

wherein:
R1 is
  -benzo[1,3]dioxol,
  -benzo[1,4]dioxin,
  -difluoro-benzo[1,3]dioxole,
  -indole, unsubstituted or substituted with lower alkyl,
  -cycloalkyl,
  -aryl, unsubstituted or mono-, di- or tri-substituted with halogen, hydroxy, alkoxy, lower alkyl, —CF$_3$, —OCF$_3$ or methanesulfonyl,
  -heteroaryl, unsubstituted or mono-, di- or tri-substituted with lower alkyl or hydroxy, and
  -N-aryl; and
R2 is -lower alkyl,
and pharmaceutically acceptable salts thereof.

2. The compound according to claim 1, wherein:
R1 is
  -benzo[1,3]dioxol,
  -benzo[1,4]dioxin,
  -difluoro-benzo[1,3]dioxole,
  -indole, unsubstituted or substituted with lower alkyl,
  -cycloalkyl,
  -aryl, unsubstituted or mono-, di- or tri-substituted with halogen, hydroxy, alkoxy, lower alkyl, —CF$_3$, —OCF$_3$ or methanesulfonyl,
  -heteroaryl, unsubstituted or mono-, di- or tri-substituted with lower alkyl or hydroxy, and
  -N-aryl; and
R2 is methyl.

3. The compound according to claim 1, wherein:
R1 is
  -benzo[1,3]dioxol,
  -benzo[1,4]dioxin,
  -difluoro-benzo[1,3]dioxole,
  -indole, unsubstituted or substituted with lower alkyl, and
  -cycloalkyl; and
R2 is lower alkyl.

4. The compound according to claim 1, wherein:
R1 is -aryl, unsubstituted or mono-, di- or tri-substituted with halogen, hydroxy, alkoxy, lower alkyl, —CF$_3$, —OCF$_3$ or methanesulfonyl, and
R2 is lower alkyl.

5. The compound according to claim 1, wherein:
R1 is -phenyl, unsubstituted or mono-, di- or tri-substituted with halogen, hydroxy, alkoxy, lower alkyl, —CF$_3$, —OCF$_3$ or methanesulfonyl; and
R2 is lower alkyl.

6. The compound according to claim 1, wherein:
R1 is phenyl; and
R2 is methyl.

7. The compound according to claim 1, wherein:
R1 is heteroaryl, unsubstituted or mono-, di- or tri-substituted with lower alkyl or hydroxy; and
R2 is methyl.

8. The compound according to claim 1, wherein R1 is phenyl, pyrazole, thiophene, thiazoles, pyridine or pyrimidine.

9. The compound according to claim 1, wherein R2 is methyl, ethyl, propyl or butyl.

10. The compound according to claim 1, wherein said compound is:
  4-{2-(2-Carboxy-ethyl)-3-[6-(4'-fluoro-5-methanesulfonyl-biphenyl-3-yloxy)-hexyl]-phenoxy}-butyric acid,
  4-{2-(2-Carboxy-ethyl)-3-[6-(4'-chloro-5-methanesulfonyl-biphenyl-3-yl oxy)-hexyl]-phenoxy}-butyric acid,
  4-(2-(2-Carboxy-ethyl)-3-{6-[3-(4-fluoro-phenoxy)-5-methanesulfonyl-phenoxy]-hexyl}-phenoxy)-butyric acid,
  4-{2-(2-Carboxy-ethyl)-3-[6-(3-cyclopropylamino-5-methanesulfonyl-phenoxy)-hexyl]-phenoxy}-butyric acid, 4-[3-[6-(3-Benzo[1,3]dioxol-5-yl-5-methanesulfonyl-phenoxy)-hexyl]-2-(2-carboxy-ethyl)-phenoxy]-butyric acid,
4-[3-[6-(3-Benzothiazol-5-yl-5-methanesulfonyl-phenoxy)-hexyl]-2-(2-carboxy-ethyl)-phenoxy]-butyric acid,
4-(2-(2-Carboxy-ethyl)-3-{6-[3-(2,2-difluoro-benzo[1,3]dioxol-5-yl)-5-methanesulfonyl-phenoxy]-hexyl}-phenoxy)-butyric acid,
4-[2-(2-Carboxy-ethyl)-3-[6-(5-ethanesulfonyl-3',4'-difluoro-biphenyl-3-yloxy)-hexyl]-phenoxy]-butyric acid,
4-[2-(2-Carboxy-ethyl)-3-[6-(5-(propane-1-sulfonyl)-4'-fluoro-biphenyl-3-yloxy)-hexyl]-phenoxy]-butyric acid, and
4-[3-[6-(3-Benzo[1,3]dioxol-5-yl-5-(propane-2-sulfonyl)-phenoxy)-hexyl]-2-(2-carboxy-ethyl)-phenoxy]-butyric acid.

11. A pharmaceutical composition, comprising a therapeutically effective amount of a compound according to claim 1 or a pharmaceutically acceptable salt thereof and a pharmaceutically acceptable carrier.

12. A method of treating an inflammatory disease or disorder, comprising the step of administering a therapeutically effective amount of a compound according to claim 1 to a patient in need thereof.

* * * * *